US007312200B2

(12) United States Patent
Malsam et al.

(10) Patent No.: US 7,312,200 B2
(45) Date of Patent: Dec. 25, 2007

(54) 9-KETOSPINOSYN DERIVATIVES

(75) Inventors: Olga Malsam, Rösrath (DE); Peter Lösel, Leverkusen (DE); Michael E. Beck, Monheim (DE); Ulrich Ebbinghaus-Kintscher, Dortmund (DE); Robert Velten, Köln (DE); Peter Jeschke, Bergisch Gladbach (DE); Volker Möhrle, Köln (DE); Rita Fröde, Brühl (DE); Günther Eberz, Odenthal (DE)

(73) Assignee: Bayer CropScience AG, Monheim (DE)

( * ) Notice: Subject to any disclaimer, the term of this patent is extended or adjusted under 35 U.S.C. 154(b) by 203 days.

(21) Appl. No.: 10/541,442

(22) PCT Filed: Jan. 8, 2004

(86) PCT No.: PCT/EP2004/000058

§ 371 (c)(1), (2), (4) Date: Jul. 6, 2005

(87) PCT Pub. No.: WO2004/065402

PCT Pub. Date: Aug. 5, 2004

(65) Prior Publication Data

US 2006/0128642 A1 Jun. 15, 2006

(30) Foreign Application Priority Data

Jan. 17, 2003 (DE) ................................ 103 01 519

(51) Int. Cl.
*A61K 31/70* (2006.01)
*C07D 313/06* (2006.01)
*C07H 17/08* (2006.01)

(52) U.S. Cl. ........................ 514/28; 536/7.1; 536/18.1; 549/268

(58) Field of Classification Search ................. 536/7.1, 536/18.1; 514/28
See application file for complete search history.

(56) References Cited

U.S. PATENT DOCUMENTS

| | | | | |
|---|---|---|---|---|
| 4,062,950 A * | 12/1977 | Frommer et al. | 514/35 |
| 5,489,680 A | 2/1996 | Failli et al. | 540/456 |
| 5,922,732 A | 7/1999 | Urch et al. | 514/304 |
| 5,968,947 A | 10/1999 | Urch et al. | 514/299 |
| 6,001,981 A | 12/1999 | DeAmicis et al. | 536/7.1 |
| 6,093,726 A | 7/2000 | Urch et al. | 514/299 |
| 6,174,894 B1 | 1/2001 | Urch et al. | 514/299 |
| 6,177,442 B1 | 1/2001 | Urch et al. | 514/299 |
| 6,207,676 B1 | 3/2001 | Urch et al. | 514/304 |
| 6,291,474 B1 | 9/2001 | Brightwell et al. | 514/299 |
| 6,391,883 B1 | 5/2002 | Urch et al. | 514/255 |
| 6,573,275 B1 | 6/2003 | Urch et al. | 514/304 |
| 7,034,130 B2 * | 4/2006 | Jeschke et al. | 536/7.1 |
| 2002/0061913 A1 | 5/2002 | Urch et al. | 514/366 |
| 2004/0147766 A1 | 7/2004 | Stader et al. | 549/268 |
| 2004/0242858 A1 | 12/2004 | Jeschke et al. | 536/7.1 |

FOREIGN PATENT DOCUMENTS

| | | |
|---|---|---|
| CA | 2059184 | 7/1992 |
| DE | 101 21 313 | 10/2002 |
| GB | 1 331 203 | 9/1973 |
| GB | 1 343 036 | 1/1974 |
| WO | 97/00265 | 1/1997 |
| WO | 03/010155 | 1/2001 |
| WO | 01/16303 A2 | 3/2001 |

OTHER PUBLICATIONS

J. Org. Chem., 59, (month unavailable) 1994, pp. 1548-1560, Jacek G. Martynow et al, "Chemistry of A83543A Derivatives. 1. Oxidations and Reductions of A83543A Aglycon".

Org. Synth. Coll., vol. II, (month unavailable) 1994, pp. 70-71, Arthur Lachman, "Benzophenone Oxime".

Org. Synth. Coll., vol. 1, (month unavailable) 1941, pp. 318-321, Waldo L. Semon, "Hydroxylamine Hydrochloride and Acetoxime".

Houben-Weyl, Methoden der Organischen Chemie, Bd. X/4, (month unavailable) 1968, pp. 55-66, H. Metzger, "Oxime".

J. Antibiotics, vol. 51, No. 8, (month unavailable) 1998, pp. 795-800, Lawrence C. Creemer et al, "Conversion of Spinosyn A and Spinosyn D to Their Respective 9- and 17-Pseudoaglycones and Their Aglycones".

J. Econ. Entomol. 91 (6), Dec. 1998, pp. 1277-1282, Thomas C. Sparks et al, "Biological Activity of the Spinosyns, New Fermentation Derived Insect Control Agents, on Tobacco Budworm (*Lepidoptera: Noctuidae*) Larvae".

Pesticide Biochemistry and Physiology, 67, (month unavailable) 2000, pp. 187-197 Thomas C. Sparks et al, "The Application of Artificial Neural Networks to the Identification of New Spinosoids with Improved Biological Activity toward Larvae of *Heliothis virescens*".

J. Am. Chem. Soc., 120, (month unavailable) 1998, pp. 2553-2562, Leo A. Paquette et al, "Total Synthesis of Spinosyn A. 2. Degradation Studies Involving the Pure Factor and Its Complete Reconstruction".

J. Am. Chem. Soc., 115, (month unavailable) 1993, pp. 4497-4513, David A. Evans et al, "Total Synthesis of (+)-A83543A [(+)-Lepiciden A]".

Pest. Manag Sci., 57(2), (month unavailable) 2001, pp. 177-185, Gary D. Crouse et al, "Recent advances in the chemistry of spinosyns".

(Continued)

*Primary Examiner*—Elli Peselev
(74) *Attorney, Agent, or Firm*—Richard E. L. Henderson

(57) ABSTRACT

The present invention relates to derivatives of 9-keto spinosyns, which are substituted by a =N—(O, NH or $NR_x$)—$R_y$ moiety in the C-9 position, to methods for their manufacture, and to their use for controlling animal pests.

11 Claims, No Drawings

OTHER PUBLICATIONS

J. Antibiotics, 53(2), Feb. 2002, pp. 171-178, Lawrence C. Creemer et al, "Synthesis and Insecticidal Activity of Spinosyn Analogs Functionally Altered at the 2'-,3'- and 4'-Positions of the Rhamnose Moiety".

Proceedings of the Beltwide Cotton Conf., vol. 2 (month unavailable) 2000, pp. 1225-1229, Thomas C. Sparks et al, "Structure Activity Relationships of the Spinosyns".

Farmaco Ed. Sci., 42,(10), Oct. 1987, pp. 697-708, D. Favara et al, "Synthesis and Calcium Antagonistic Activity of a new Class of 1,4-Dihydropyridines Having an Alkoxyimino Group in Position 3".

J. Chem. Soc., Chem. Commun. (month unavailable) 1991, p. 435-437, Joëlle Vidal et al, "N-Amination Using N-Methoxycarbonyl-3-phenyloxaziridine. Direct Access to Chiral $N_\beta$-Protected $\alpha$-Hydrazinoacids and Carbazates".

J. Org. Chem. 58, (month unavailable) 1993, pp. 4791-7493, Joëlle Vidal et al, "Electrophilic Amination: Preparation and Use of *N*-Boc-3-(4-cyanophenyl)oxaziridine, a New Reagent That Transfers a *N*-Boc Group to N- and C-Nucleophiles".

J. Org. Chem. 66, (month unavailable) 2001, pp. 2869-2873, Nicolas Brosse et al, "A New Synthetic Route to Protected $\alpha$-Hydrazinoesters in High Optical Purity Using the Mitsunobu Protocol".

* cited by examiner

9-KETOSPINOSYN DERIVATIVES

The present patent application has been filed under 35 U.S.C. 371 as a national stage application of PCT/EP2004/000058, filed Jan. 8, 2004, which was published in German as International Patent Publication WO 2004/065402 on Aug. 5, 2004, and is entitled to the right of priority of German Patent Application 103 01 519.1, filed Jan. 17, 2003.

The present invention relates to derivatives of 9-keto spinosyns, which are substituted by a =N—(O, NH or $NR_x$)—$R_y$ moiety in the C-9 position, methods for their manufacture, and their use for controlling animal pests.

Spinosyns are known compounds; they are fermentation products, which are manufactured from the cultures of the actinomycete *Saccharopolyspora spinosa.*

Synthetic preparations for the manufacture of spinosyn derivatives were described by Martynow, J. G. and Kirst, H. A. in J. Org. Chem. 1994, 59, 1548. In this publication, both the 9,17-diketone of the spinosyn aglycone and the 17-keto derivative of the spinosyn aglycone are mentioned. The spinosyn-17-pseudoaglycone and spinosyn-9-pseudoaglycone are disclosed in WO 97/00265 and U.S. Pat. No. 6,001,981. The manufacture of additional derivatives is described in these texts, which are obtainable with semi synthetic methods starting from natural products. The spinosyn-9-pseudoaglycone derivative, which is oxidised into ketone at the C-9 position, is also known as an insecticide compound, for example, and was produced through chemical derivatisation (see. WO 97/00265 and U.S. Pat. No. 6,001,981).

The object of the present invention is to provide new derivatives of 9-keto spinosyns. An additional object of the present invention is to provide methods that are suitable for the manufacture of these derivatives.

The present invention relates to compounds according to the general formula (I)

(I)

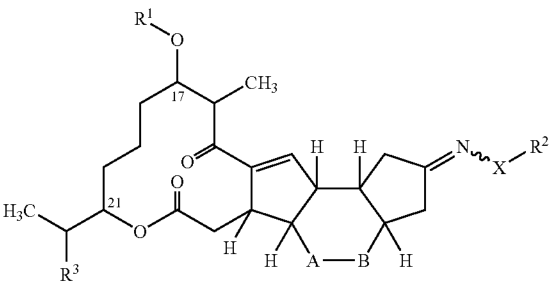

and derived salts, where

X stands for O, NH or $NR^4$, $R^1$ stands for hydrogen or an amino sugar, $R^2$ stands for hydrogen or a possibly substituted alkyl, cycloalkyl, arylalkyl, hetarylalkyl, aryl or hetaryl, or for CO—R' or CS—R' if X stands for NH or $NR^4$, where R' stands for amino, possibly substituted alkyl, alkylamino, dialkylamino, aryl, arylamino, hetarylamino, arylalkyl, hetaryl or hetarylalkyl, $R^3$ stands for hydrogen or hydroxy, $R^4$ stands for possibly substituted alkyl, or forms a 3-, 4-, 5-, 6-, 7- or 8-membered ring with $R^2$, which can be interrupted by one or more heteroatom(s) such as O, S, SO, $SO_2$, NH or $NR^5$, and is possibly substituted, $R^5$ stands for possibly substituted alkyl, cycloalkyl, arylalkyl, hetarylalkyl, aryl or hetaryl, and A-B stands for one of the following groups: —HC═CH—, —HC═C($CH_3$)—, —$H_2C$—$CH_2$— or —$H_2C$—CH($CH_3$)—.

The following sections will explain preferred substituents or regions of the moieties listed in the formulas indicated above or below.

The occurrence of possibly substituted alkyl by itself or as a component of a moiety in the general formulas designates straight-chained or branched alkyl with preferably 1 to 6, particularly 1 to 4 carbon atoms. The following are mentioned as examples: possibly substituted methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylbutyl, 1,1-dimethylpropyl, 2,2-dimethylpropyl, 1-ethoxypropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, and 2-ethylbutyl. Preferable substances are methyl, ethyl, n-propyl, isopropyl, n-butyl, isobutyl, sec-butyl and tert-butyl.

The occurrence of possibly substituted cycloalkyl by itself or as a component of a moiety in the general formulas designates mono-, bi-, and tricyclic cycloalkyl, preferably with 3 to 10, particularly with 3, 5 or 7 carbon atoms. The following are mentioned as examples: possibly substituted cyclopropyl, cyclobutyl, cyclopentyl, cyclohexyl, cycloheptyl, cyclooctyl, bicyclo[2.2.1]heptyl, bicyclo[2.2.2]octyl, and adamantyl.

The occurrence of possibly substituted arylalkyl in the general formulas preferably designates substituted arylalkyl possibly in the aryl portion and/or alkyl portion with an aryl portion defined as described below, and with preferably 1 to 4, particularly 1 or 2 carbon atoms in the alkyl portion, and the alkyl portion can be straight-chained or branched. Benyl and phenylethyl are mentioned as examples and as preferable substances.

The occurrence of possibly substituted hetarylalkyl in the general formulas preferably designates substituted hetarylalkyl possibly in the hetaryl portion and/or alkyl portion with a hetaryl portion defined as described below, and with preferably 1 to 4, particularly 1 or 2 carbon atoms in the alkyl portion, and the alkyl portion can be straight-chained or branched.

The occurrence of possibly substituted aryl by itself or as a component of a moiety in the general formulas designates, for example, a mononuclear, binuclear or polynuclear aromatic moiety such as phenyl, naphthyl, tetrahydronaphthyl, indanyl, fluorenyl, however preferably phenyl or naphthyl, and particularly phenyl.

The occurrence of possibly substituted hetaryl by itself or as a component of a moiety in the general formulas designates 5- to 7-membered rings with preferably 1 to 3, particularly 1 or 2 of the same or different heteroaromates. Oxygen, sulphur or nitrogen can be heteroatoms in the heteroaromates. The following are listed as examples, and are preferred: possibly substituted furyl, thienyl, pyrazolyl, imidazolyl, 1,2,4- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl oxepinyl, thiepinyl and 1,2,4-diazepinyl.

The possibly substituted moieties in the general formulas can carry one or more, preferably 1 to 3, particularly 1 to 2 identical or different substituents. The following are listed as examples of preferred substituents:

Alkyl with preferably 1 to 4, particularly 1 to 2 carbon atoms, such as methyl, ethyl, n-propyl, isopropyl, n-butyl, isobutyl, sec-butyl and tert-butyl; alkoxy with preferably 1 to 4, particularly 1 to 2 carbon atoms, such as methoxy, ethoxy, n-propoxy, isopropoxy, n-butoxy, isobutoxy, sec-butoxy and tert-butoxy; alkylthio with preferably 1 to 4, particularly 1 to 2 carbon atoms, such as methylthio, ethylthio, n-propylthio, isopropylthio, n-butylthio, isobutylthio, sec-butylthio and tert-butylthio; halogenalkyl with preferably 1 to 4, particularly 1 to 2 carbon atoms and preferably 1 to 4, particularly 1 to 3 halogen atoms, where the halogen atoms are identical or different and are preferably fluorine, chlorine, bromine, iodine, particularly fluorine or chlorine, such as difluoromethyl, trifluoromethyl, trichloromethyl; hydroxy, halogen, preferably fluorine, chlorine, bromine, iodine, particularly fluorine and chlorine; cyano; nitro; amino; monoalkyl- and dialkylamino with preferably 1 to 4, particularly 1 or 2 carbon atoms per alkyl group, such as methylamino, methylethylamino, dimethylamino, n-propylamino, isopropylamino, methyl-n-butylamino; alkylcarbonyl moieties such as methylcarbonyl, alkoxycarbonyl with preferably 2 to 4, particularly 2 to 3 carbon atoms, such as methoxycarbonyl and ethoxycarbonyl; alkylsulphinyl with 1 to 4, particularly 1 to 2 carbon atoms; halogensulphinyl with 1 to 4, particularly 1 to 2 carbon atoms, and 1 to 5 halogen atoms such as trifluoromethylsulphinyl; sulphonyl (—$SO_2$—OH); alkylsulphonyl with preferably 1 to 4, particularly 1 or 2 carbon atoms, such as methylsulphonyl and ethylsulphonyl or halogenalkylsulphonyl with 1 to 4, particularly 1 to 2 carbon atoms and 1 to 5 halogen atoms such as trifluoromethanesulphonyl.

Suitable cyclic amino groups can be heteroaromatic or aliphatic ring systems with one or more nitrogen atoms as a heteroatom, in which the heterocycles can be saturated or unsaturated, a ring system or several condensed ring systems, and can possibly contain additional heteroatoms such as nitrogen, oxygen, and sulphur, etc. In addition, cyclic amino groups can also designate a spiro ring or a bridged ring system. The number of atoms that form cyclic amino groups is not restricted; for example, they consist of from 3 to 8 atoms in the case of a single-ring system, and of from 7 to 11 atoms in the case of a triple-ring system.

The following are examples of cyclic amino groups: saturated and unsaturated monocyclic ring systems with one nitrogen atom as a heteroatom, such as 1-azetidinyl, pyrrolidino, 2-pyrrolin-1-yl, 1-pyrrolyl, piperidino, 1,4-dihydropyridin-1-yl, 1,2,5,6-tetrahydropyridin-1-yl and homopiperidino; examples of cyclic amino groups are saturated and unsaturated monocyclic ring systems with two or more nitrogen atoms as heteroatoms, such as 1-imidazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropyrimidin-1-yl, perhydropyrimidin-1-yl and 1,4-diazacycloheptan-1-yl; examples of cyclic amino groups are saturated and unsaturated monocyclic ring systems with one to three nitrogen atoms and one to two oxygen atoms as heteroatoms, such as oxazolin-3-yl, isoxazolin-2-yl, morpholino or 2,6-dimethylmorpholino; examples of cyclic amino groups are saturated or unsaturated monocyclic ring systems with one to three nitrogen atoms and one to two sulphur atoms as heteroatoms; examples of cyclic amino groups are saturated and unsaturated condensed ring systems such as indol-1-yl, 1,2-dihydro-benzimidazol-1-yl, perhydropyrrolo[1,2]pyrazin-2-yl; examples of cyclic amino groups are spiro-cyclic ring systems such as 2-azaspiro[4,5]-decan-2-yl; examples of cyclic amino groups are bridged heterocyclic ring systems such as 2-azabicyclo[2,2,1]heptan-7-yl.

The compounds according to the invention are generally defined by formula (I).

The preferred substituents and regions of the moieties listed in the formulas shown above and below are described in the following section.

X preferably stands for O, NH or NMe.

$R^1$ preferably stands for hydrogen or for an amino sugar shown in the formulae 1a to 1g 1a

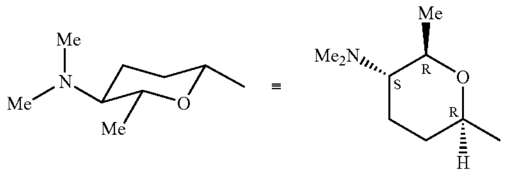

1b

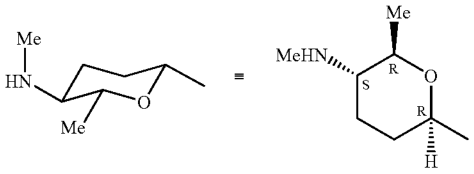

1c

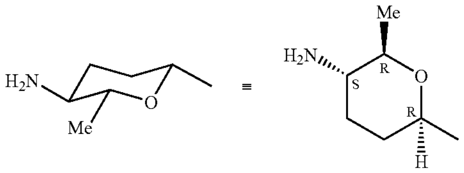

1d

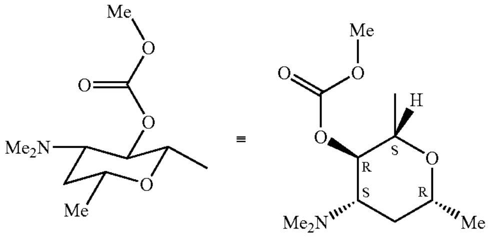

1e

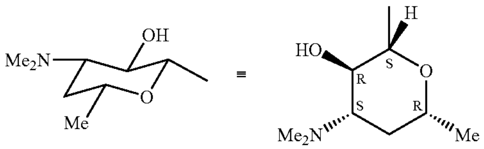

1f

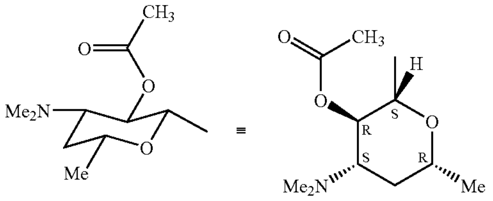

-continued

1g

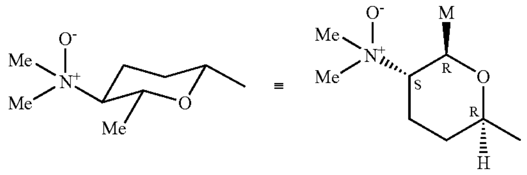

$R^2$ preferably stands for possibly substituted aryl-$C_1$-$C_3$-alkyl, particularly for benzyl, 1-phenyl-ethyl, 2-phenyl-ethyl, 3-phenyl-propyl, 2-phenyl-propyl, 2-phenyl-isopropyl, 1-methyl-2-phenyl-ethyl, hetaryl-$C_1$-$C_3$-alkyl, hetarylmethyl, 1-hetaryl-ethyl, 2-hetaryl-ethyl, 3-hetaryl-propyl, 2-hetaryl-propyl, 2-hetaryl-isopropyl, 1-methyl-2-hetaryl-ethyl, and the substituents can be selected from the group of hydrogen, straight-chained or branched alkyl with up to 4 carbon atoms, in particular methyl, ethyl, propyl, isopropyl, butyl, isobutyl, sec-butyl, tert-butyl, halogenalkyl with up to 2 carbon atoms, in particular trifluoromethyl, difluorochloromethyl, pentafluoroethyl, alkenyl with up to 3 carbon atoms, cyclic alkyl with up to 6 carbon atoms, in particular cyclopropyl, cyclobutyl, cyclopentyl, cyclohexyl, hydroxy, halogen, particularly bromine, chlorine, fluorine or iodine, alkoxy, particularly methoxy, ethoxy, propoxy, isopropoxy, butoxy, isobutoxy, sec-butoxy, tert-butoxy, cycloalkoxy, particularly cyclopropyloxy, alkenyloxy, in particular allyloxy, dioxoalkylene, particularly dioxomethylene, halogenalkoxy, in particular trifluoromethoxy, alkylthio, particularly methylthio, halogenalkylthio, particularly trifluoromethylthio, alkylsulphonyl, particularly methylsulphonyl, halogenalkylsulphonyl, in particular trifluoromethylsulphonyl, hetarylsulphonyl, particularly N-morpholinosulphonyl or N-pyrazolylsulphonyl, nitro, amino, a suitable cyclic amino group, particularly N-pyrrolidino, N-piperidino, N-morpholino, N-(2,6-dimethylmorpholino), N-methyl-piperazino, N-thiomorpholino or N-dioxothiomorpholino, alkylamino, particularly methylamino, ethylamino, propylamino, isopropylamino, butylamino, sec-butylamino, isobutylamino, tert-butylamino, alkyleneamino, in particular propyleneamino, dialkylamino, particularly dimethylamino, diethylamino, carboxyl, carbamoyl, cyano, alkoxycarbonyl, particularly methoxycarbonyl, ethoxycarbonyl, propyloxycarbonyl, isopropyloxycarbonyl, butyloxycarbonyl, sec-butyloxycarbonyl, isobutyloxycarbonyl, tert-butyloxycarbonyl, alkyleneoxycarbonyl, particularly propyleneoxycarbonyl, N-alkoxycarbonyl-amino, particularly N-methoxycarbonylamino, N-ethoxycarbonylamino, N-propyloxycarbonylamino, N-isopropyloxycarbonyl-amino, N-butyloxycarbonyl-amino, N-sec-butyloxycarbonylamino, N-isobutyloxycarbonylamino, N-tert-butyloxycarbonylamino, cyanoalkylenecar-bonylamino, particularly cyanomethylene-carbonylamino, cyanoethylene-carbonylamino, N-alkyleneoxycarbonylamino, in particular N-propyleneoxycarbonylamino, N-alkylsulphonylamino, particularly N-methylsulphonylamino, N-ethylsulphonylamino, N-propylsulphonylamino, N-isopropylsulphonylamino, N-butylsulphonylamino, N-sec-butylsulphonylamino, N-isobutylsulphonyl-amino, N-tert-butylsulphonylamino, N-alkylenesulphonylamino, in particular N-propylenesulphonylamino, possibly substituted arylsulphonylamino, particularly 4-trifluoromethylphenylsulphonylamino, N-alkoxycarbonyl-N-alkylamino, particularly N-methoxycarbonyl-N-methylamino, N-methoxy-carbonyl-N-ethyl-amino, N-ethoxycarbonyl-N-methyl-amino, N-ethoxycarbonyl-N-ethyl-amino, N-propyloxycarbonyl-N-methyl-amino, N-propyloxycarbonyl-N-ethyl-amino, N-isopropyloxycarbonyl-N-methyl-amino, N-isopropyloxycarbonyl-N-ethyl-amino, N-butyloxycarbonyl-N-methyl-amino, N-butyloxy-carbonyl-N-ethyl-amino, N-sec-butyloxycarbonyl-N-methyl-amino, N-sec-butyloxycarbonyl-N-ethyl-amino, N-isobutyloxy-carbonyl-N-methyl-amino, N-isobutyloxycarbonyl-N-ethyl-amino, N-tert-butyloxycarbonyl-N-methyl-amino, N-tert-butyloxycarbonyl-N-methyl-amino, N-alkyleneoxycarbonyl-N-alkyl-amino, particularly N-propyleneoxycarbonyl-N-methylamino, N-propyleneoxycarbonyl-N-methyl-amino, N-alkylcarbonyl-N-alkylamino, in particular N-methylcarbonyl-N-methyl-amino, N-methyl-carbonyl-N-ethyl-amino, N-ethyl-carbonyl-N-methyl-amino, N-ethylcarbonyl-N-ethyl-amino, N-cycloalkylcarbonylamino, particularly N-cyclopropyl-carbonylamino, N-1-methylcycloprop-1-yl-carbonyl-N-amino, N-cyclobutyl-amino, N-alkoxy-carbonyl-N-alkylsulphonyl-amino, particularly N-methoxy-carbonyl-N-methylsulphonyl-amino, N-methoxycarbonyl-N-ethyl-sulphonylamino, N-ethoxy-carbonyl-N-methylsulphonyl-amino, N-ethoxy-carbonyl-N-ethyl-sulphonylamino, N-propyloxycarbonyl-N-methyl-sulphonyl-amino, N-propyloxy-carbonyl-N-ethylsulphonyl-amino, N-isopropyloxycarbonyl-N-methylsulphonyl-amino, N-isopropyloxycarbonyl-N-ethylsulphonylamino, N-butyloxycarbonyl-N-methylsulphonyl-amino, N-butyloxycarbonyl-N-ethyl-sulphonylamino, N-sec-butyloxycarbonyl-N-methylsulphonyl-amino, N-sec-butyloxycarbonyl-N-ethyl-sulphonyl-amino, N-isobutyloxycarbonyl-N-methyl-sulphonyl-amino, N-isobutyloxycarbonyl-N-ethylsulphonylamino, N-tert-butyloxy-carbonyl-N-methyl-sulphonylamino, N-tert-butyloxycarbonyl-N-methylsulphonyl-amino, N-alkyleneoxycarbonyl-N-alkylsulphonyl-amino, in particular N-propyleneoxycarbonyl-N-methylsulphonyl-amino, N-propyleneoxycarbonyl-N-methylsulphonyl-amino, N-alkylcarbonyl-N-alkylsulphonyl-amino, particularly N-methylcarbonyl-N-methylsulphonyl-amino, N-methyl-carbonyl-N-ethylsulphonyl-amino, N-ethyl-carbonyl-N-methylsulphonyl-amino, N-ethylcarbonyl-N-ethyl-sulphonylamino, N-cycloalkylcarbonyl-N-alkylsulphonyl-amino, particularly N-cyclopropyl-carbonyl-N-methylsulphonyl-amino, N-1-methylcycloprop-1-yl-carbonyl-N-methylsulphonylamino, N-cyclobutyl-N-methylsulphonylamino, alkylaminocarbonylamino, in particular N-methylaminocarbonylamino, N-ethylaminocarbonylamino, N,N-dialkylaminocarbonylamino, particularly N,N-dimethylaminocarbonylamino, N-alkylaminosulphonylamino, in particular N-methylaminosulphonylamino, N,N-dialkylaminosulphonylamino, particularly N,N-dimethylaminosulphonylamino.

If X stands for NH or NMe, then $R^2$ continues to preferably stand for CO—R' or CS—R', where R' stands for amino, possibly substituted $C_1$-$C_4$-alkyl, $C_1$-$C_4$-alkylamino, Di-$C_1$-$C_4$-alkylamino, aryl, arylamino, hetarylamino, aryl-$C_1$-$C_3$-alkyl, hetaryl or hetaryl-$C_1$-$C_3$-alkyl.

$R^4$ preferably stands for possibly substituted $C_1$-$C_4$-alkyl or forms a 6-membered ring with $R^2$, which can be interrupted by O, S or $NR^5$, and which is substituted if necessary.

$R^5$ preferably stands for possibly substituted $C_1$-$C_4$-alkyl.

X particularly preferably stands for O or NH.

$R^1$ particularly preferably stands for hydrogen or for an amino sugar shown in the formulae 1a, 1d or 1e 1a

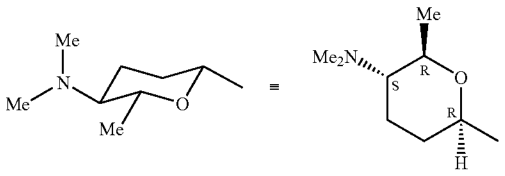

1d

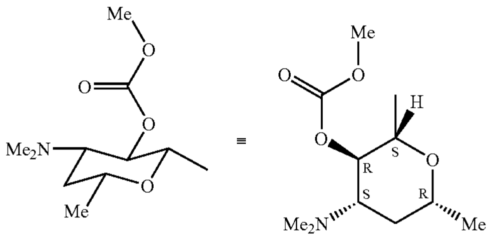

1e

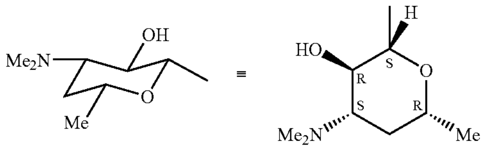

$R^2$ particularly preferably stands for aryl-$C_1$-$C_3$-alkyl, in particular for benzyl, 1-phenyl-ethyl, hetaryl-$C_1$-$C_3$-alkyl, hetarylmethyl, particularly pyridylmethyl, pyrimidylmethyl, pyridazinylmethyl, pyrazylmethyl, furylmethyl, thiazolylmethyl, pyrazolylmethyl, oxazolylmethyl, isoxazolylmethyl, thiazolylmethyl, imidazolylmethyl, triazolylmethyl, tetrazolylmethyl, dihydro-dioxazinylmethyl, 1-hetaryl-ethyl, in particular 1-pyridylethyl, 1-pyrimidylethyl, 1-pyridazinylethyl, 1-pyrazylethyl, 1-furylethyl, 1-thiazolylethyl, 1-pyrazolylethyl, 1-oxazolylethyl, 1-isoxazolylethyl, 1-thiazolylethyl, 1-imidazolylethyl, 1-triazolylethyl, 1-tetrazolylethyl, 1-dihydro-dioxazinylethyl, which can each be substituted by moieties from the group of hydrogen, straight-chained or branched alkyl with up to 4 carbon atoms, in particular methyl, ethyl, propyl, tert-butyl, halogenalkyl, in particular trifluoromethyl, hydroxy, halogen, particularly bromine, chlorine, fluorine or iodine, alkoxy, particularly methoxy, ethoxy, tert-butoxy, halogenalkoxy, in particular trifluoromethoxy, alkylthio, particularly methylthio, halogenalkylthio, particularly trifluoromethylthio, alkylsulphonyl, particularly methylsulphonyl, halogenalkylsulphonyl, in particular trifluoromethylsulphonyl, nitro, amino, alkylamino, in particular methylamino, ethylamino, N-alkoxycarbonylamino, particularly N-methoxycarbonylamino, N-ethoxycarbonylamino, N-propyloxycarbonylamino, N-isopropyloxycarbonyl-amino, N-butyloxycarbonylamino, N-sec-butyloxycarbonylamino, N-isobutyloxycarbonylamino, N-tert-butyloxycarbonylamino, N-alkyleneoxycarbonyl-amino, in particular N-propyleneoxycarbonylamino, N-alkylsulphonylamino, particularly N-methylsulphonylamino, N-ethylsulphonylamino, N-propylsulphonylamino, N-isopropylsulphonylamino, N-butylsulphonylamino, N-sec-butylsulphonylamino, N-isobutylsulphonyl-amino, N-tert-butylsulphonylamino, N-N-alkoxycarbonyl-N-alkyl-amino, particularly N-methoxycarbonyl-N-methyl-amino, N-methoxy-carbonyl-N-ethyl-amino, N-ethoxycarbonyl-N-methyl-amino, N-ethoxycarbonyl-N-ethyl-amino, N-propyloxycarbonyl-N-methyl-amino, N-propyloxycarbonyl-N-ethyl-amino, N-isopropyloxycarbonyl-N-methyl-amino, N-isopropyloxycarbonyl-N-ethyl-amino, N-butyloxy-carbonyl-N-methyl-amino, N-butyloxy-carbonyl-N-ethyl-amino, N-sec-butyloxycarbonyl-N-methyl-amino, N-sec-butyloxycarbonyl-N-ethyl-amino, N-isobutyloxy-carbonyl-N-methyl-amino, N-isobutyloxycarbonyl-N-ethyl-amino, N-tert-butyloxycarbonyl-N-methyl-amino, N-tert-butyloxycarbonyl-N-methyl-amino, N-alkyleneoxycarbonyl-N-alkyl-amino, particularly N-propyleneoxycarbonyl-N-methylamino, N-propyleneoxycarbonyl-N-methyl-amino, N-alkylcarbonyl-N-alkylamino, particularly N-methylcarbonyl-N-methyl-amino, N-methylcarbonyl-N-ethyl-amino, N-ethyl-carbonyl-N-methyl-amino, N-ethylcarbonyl-N-ethyl-amino, N-cycloalkylcarbonylamino, in particular N-cyclopropylcarbonylamino, N-1-methylcycloprop-1-yl-carbonyl-N-amino, N-cyclobutylamino, N-alkoxy-carbonyl-N-alkylsulphonyl-amino, particularly N-methoxycarbonyl-N-methylsulphonyl-amino, N-methoxycarbonyl-N-ethyl-sulphonylamino, N-ethoxycarbonyl-N-methylsulphonyl-amino, N-ethoxy-carbonyl-N-ethylsulphonyl-amino, N-propyloxycarbonyl-N-methyl-sulphonyl-amino, N-propyloxycarbonyl-N-ethylsulphonyl-amino, N-isopropyloxycarbonyl-N-methyl-sulphonyl-amino, N-isopropyloxycarbonyl-N-ethylsulphonyl-amino, N-butyloxycarbonyl-N-methylsulphonylamino, N-butyloxycarbonyl-N-ethylsulphonylamino, N-sec-butyloxy-carbonyl-N-methylsulphonyl-amino, N-sec-butyloxycarbonyl-N-ethylsulphonyl-amino, N-isobutyloxycarbonyl-N-methylsulphonyl-amino, N-isobutyloxy-carbonyl-N-ethylsulphonyl-amino, N-tert-butyloxy-carbonyl-N-methylsulphonyl-amino, N-tert-butyloxycarbonyl-N-methylsulphonyl-amino, N-alkyleneoxycarbonyl-N-alkylsulphonyl-amino, particularly N-propyleneoxycarbonyl-N-methylsulphonyl-amino, N-propyleneoxycarbonyl-N-methylsulphonyl-amino, N-alkylcarbonyl-N-alkylsulphonyl-amino, particularly N-methylcarbonyl-N-methylsulphonyl-amino, N-methylcarbonyl-N-ethylsulphonyl-amino, N-ethyl-carbonyl-N-methylsulphonyl-amino, N-ethylcarbonyl-N-ethylsulphonyl-amino, N-cycloalkylcarbonyl-N-alkylsulphonyl-amino, in particular N-cyclopropylcarbonyl-N-methylsulphonyl-amino, N-1-methylcycloprop-1-yl-carbonyl-N-methylsulphonylamino, N-cyclobutyl-N-methylsulphonylamino, alkylamino-carbonylamino, particularly N-methylaminocarbonylamino, N-ethyl-aminocarbonylamino, N,N-dialkylaminocarbonylamino, particularly N,N-dimethylaminocarbonylamino, N-alkylaminosulphonylamino, in particular N-methylaminosulphonylamino, N,N-dialkylaminosulphonylamino, in particular N,N-dimethylaminosulphonylamino.

If X stands for NH or Nme, then $R^2$ particularly preferably continues to stand for CO—R' or CS—R', where R' stands for amino, arylamino, particularly trifluoromethoxyphenylamino, trifluoromethylphenylamino, chlorophenylamino, hetarylamino, particularly bromopyridylamino or trifluoromethylpyridylamino.

X particularly preferably stands for O.

$R^1$ quite particularly preferably stands for hydrogen or for an amino sugar as shown in the formulae 1a and 1e 1a

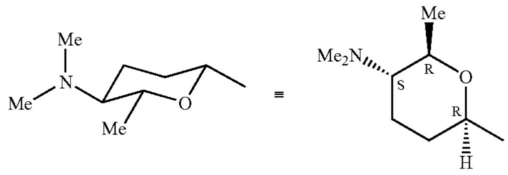

1e

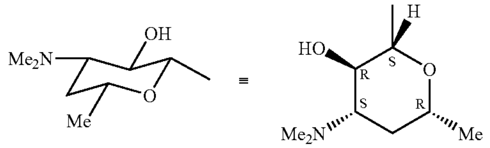

$R^2$ quite particularly preferably stands for benzyl, 1-phenylethyl, hetarylmethyl, particularly pyridylmethyl, pyridazinylmethyl, thiazolylmethyl, pyrazolylmethyl, isoxazolylmethyl, imidazolylmethyl, dihydro-dioxazinylmethyl, 1-pyridylethyl, 1-thiazolylethyl, 1-dihydro-dioxazinylethyl, which can be possibly substituted by moieties from the group consisting of hydrogen, methyl, tert-butyl, trifluoromethyl, bromine, chlorine, fluorine, methoxy, trifluoromethoxy, nitro, amino, methylamino, ethylamino, N-methoxycarbonylamino, N-ethoxycarbonylamino, N-propyloxycarbonyl-amino, N-isopropyloxycarbonyl-amino, N-tert-butyloxycarbonylamino, N-propyleneoxy-carbonylamino, N-methylsulphonylamino, N-ethylsulphonyl-amino, N-methoxycarbonyl-N-methyl-amino, N-ethoxycarbonyl-N-methyl-amino, N-isopropyloxycarbonyl-N-methyl-amino, N-tert-butyloxycarbonyl-N-methyl-amino, N-propyleneoxy-carbonyl-N-methylamino, N-cyclopropyl-carbonylamino, N-1-methylcycloprop-1-yl-carbonyl-N-amino, N-methoxy-carbonyl-N-methylsulphonyl-amino, N-methoxycarbonyl-N-ethyl-sulphonylamino, N-isobutyloxycarbonyl-N-methyl-sulphonyl-amino, N-tert-butyloxycarbonyl-N-methylsulphonyl-amino, N-tert-butyloxycarbonyl-N-methylsulphonyl-amino, N-propyleneoxycarbonyl-N-methylsulphonyl-amino, N-cyclopropylcarbonyl-N-methyl-sulphonyl-amino, N-1-methylcycloprop-1-yl-carbonyl-N-methyl-sulphonyl-amino, N,N-dialkylaminocarbonyl-amino, N-methylaminosulphonyl-amino and N,N-dialkylamino-sulphonyl-amino.

A-B preferably stands for one of the following groups: $-HC{=}CH-$ or $-H_2C-CH_2-$.

According to the invention, the compounds according to formula (I) are preferred, in which a combination of the previously listed preferred substances occur.

According to the invention, the compounds according to formula (I) are particularly preferred, in which a combination of the previously listed particularly preferred substances occur.

According to the invention, the compounds according to formula (I) are quite particularly preferred, in which a combination of the previously listed quite particularly preferred substances occur.

The 9-keto spinosyn derivatives according to the invention and their acid addition salts and metal complexes according to the general formula (I) possess strongly pronounced biological properties and are suitable first and foremost for controlling animal pests, in particular insects, arachnids and nematodes, which occur in the agricultural industry, forests, the areas of material and stock protection and in the hygiene sector.

The general definitions of moieties above and the preferred definitions of moieties or explanations apply to the end products, and to the initial and intermediate products, respectively. These moieties can be combined with each other in any manner, i.e. among the respective preferred substances.

The 9-keto spinosyn derivatives according to the invention according to the general formula (I) and their salts can exist in stereoisomer forms, which either behave as an object and a mirror image of that object (enantiomers), or not as an object and a mirror image of that object (diastereomers). The enantiomers and the diastereomers, and their corresponding mixtures are all subjects of the present invention. The racemic forms can be separated into stereomers with uniform components according to a known method, as can the diastereomers. If necessary, the isomers can be converted into one another using methods known in their own right.

However, the optically active, stereoisomer forms of the compounds according to the general formula (I) and their salts are preferably formed and utilised, according to the invention.

The invention therefore relates to both the pure enantiomers and diastereomers, and their mixtures for use as plant protection agents.

The compounds according to the invention, in which $R^1$ stands for an amino sugar shown in the formulae 1a to 1f, and/or $R^3$ stands for a basic moiety, can form salts. Suitable salts of the 9-keto spinosyn derivatives according to the general formula (I) can be customary non-toxic salts, i.e. salts with various bases, and salts with additional acids. Examples of preferable salts are those with inorganic bases, such as alkali metal salts, for example sodium, potassium, or caesium salts, earth alkali metal salts, for example calcium or magnesium salts, ammonium salts, salts with organic bases as well as with inorganic amines, for example triethylammonium, dicyclohexylammonium, N,N'-dibenzylethylenediammonium, pyridinium, picolinium or ethanol ammonium salts, salts with inorganic acids, for example hydrochlorides, hydrobromides, dihydrosulphates, trihydrosulphates, or phosphates, salts with organic carboxylic acids or organic sulphonic acids, for example formiates, acetates, trifluoroacetates, maleates, tartrates, methanesulphonates, benzolsulphonates or para-toluene sulphonates, salts with basic amino acids, for example arginates, aspartates or glutamates, and similar salts.

Salts are formed according to the standard method for salt production. For example, the compounds according to the invention are neutralised with corresponding acids, in order to form acid addition salts. Representative usable acid addition salts are salts, which are formed, for example, through reaction with other inorganic acids, such as, for example, sulphuric acid, hydrochloric acid, hydrobromic acid, phosphoric acid, or organic carboxylic acids such as acetic acid, trifluoroacetic acid, citric acid, succinic acid, lactic acid, formic acid, maleic acid, camphoric acid, phthalic acid, glycolic acid, glutaric acid, stearic acid, salicylic acid, sorbinic acid, cinnamic acid, picric acid, benzoic acid, or organic sulphonic acids such as methane sulphonic acids and para-toluene sulphonic acids, or with basic amino acids such as asparagine acid, glutaminic acid, arginine or similar acids.

Examples of the new 9-keto spinosyn derivatives according to the invention according to the general formula (I) are listed below in Groups 1 to 94:

Group 1

(I)

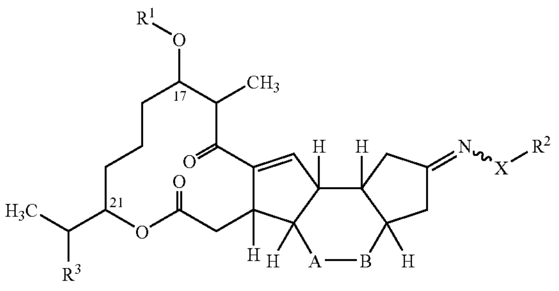

and derived salts,

Compounds of Group 1 correspond to the general formula (I), in which A-B stands for the group —HC═CH—, $R^1$ and $R^3$ stand for hydrogen, X stands for O and $R^2$ stands for a moiety listed in Table 1 as follows:

TABLE 1

| Comp. No. | $R^2$ |
|---|---|
| 1 | 4-$NH_2$-phenyl-$CH_2$—$CH_2$— |
| 2 | 4-Cpr-CO—NH-phenyl-$CH_2$—$CH_2$— |
| 3 | 4-Cpr-CO—NMe-phenyl-$CH_2$—$CH_2$— |
| 4 | 4-Cpr-CO—NEt-phenyl-$CH_2$—$CH_2$— |
| 5 | 3-$NH_2$-phenyl-$CH_2$—$CH_2$— |
| 6 | 3-Cpr-CO—NH-phenyl-$CH_2$—$CH_2$— |
| 7 | 3-Cpr-CO—NMe-phenyl-$CH_2$—$CH_2$— |
| 8 | 3-Cpr-CO—NEt-phenyl-$CH_2$—$CH_2$— |
| 9 | 4-MCpr-CO—NH-phenyl-$CH_2$—$CH_2$— |
| 10 | 4-MCpr-CO—NMe-phenyl-$CH_2$—$CH_2$— |
| 11 | 4-MCpr-CO—NEt-phenyl-$CH_2$—$CH_2$— |
| 12 | 4-Ph-O-phenyl-$CH_2$—$CH_2$— |
| 13 | 4-$MeSO_2$—NH-phenyl-$CH_2$—$CH_2$— |
| 14 | 3-$MeSO_2$—NH-phenyl-$CH_2$—$CH_2$— |
| 15 | 2-chloro-pyrid-5-yl-$CH_2$— |
| 16 | 2-chloro-pyrid-5-yl-$CH_2$—$CH_2$— |
| 17 | 4-$EtSO_2$—N(COOMe)-phenyl-$CH_2$—$CH_2$— |
| 18 | 4-$MeSO_2$—N(COOtBu)-phenyl-$CH_2$—$CH_2$— |
| 19 | 4-$Me_2$NCO—NH-phenyl-$CH_2$—$CH_2$— |
| 20 | 4-$H_2$C═CHOCO—NMe-phenyl-$CH_2$—$CH_2$— |
| 21 | 4-NC—$CH_2$—CS—NH-phenyl-$CH_2$—$CH_2$— |
| 22 | 4-NC—$CH_2$—CO—NMe-phenyl-$CH_2$—$CH_2$— |
| 23 | 4-Cbu-CO—NH-phenyl-$CH_2$—$CH_2$— |
| 24 | 4-MeNHCO—NH-phenyl-$CH_2$—$CH_2$— |
| 25 | 4-NC—$CH_2$—$CH_2$—O—CO—NEt—phenyl-$CH_2$—$CH_2$— |
| 26 | 3-Br-pyrid-5-yl-$CH_2$— |
| 27 | 2-Cl-thiazol-5-yl-$CH_2$— |

TABLE 1-continued

| Comp. No. | $R^2$ |
|---|---|
| 28 | 4-Cbu-CO—N($SO_2$Me)-phenyl-$CH_2$—$CH_2$— |
| 29 | 4-Cbu-CO—N($SO_2$Me)-phenyl-$CH_2$—$CH_2$— |
| 30 | 4-iPrCO—N($SO_2$Me)-phenyl-$CH_2$—$CH_2$— |
| 31 | 4-sec-BuCO—NH-phenyl-$CH_2$—$CH_2$— |
| 32 | 4-MCpr-CO—N($SO_2$Me)-phenyl-$CH_2$—$CH_2$— |
| 33 | 4-MCpr-CO—N(COOMe)-phenyl-$CH_2$—$CH_2$— |
| 34 | 4-MCpr-CO—N(COOiPr)-phenyl-$CH_2$—$CH_2$— |
| 35 | 2-$NH_2$-pyrid-5-yl-$CH_2$— |
| 36 | 4-Boc-NH-phenyl-$CH_2$—$CH_2$— |
| 37 | 4-Boc-NMe-phenyl-$CH_2$—$CH_2$— |
| 38 | 3-Boc-NH-phenyl-$CH_2$—$CH_2$— |
| 39 | 3-Boc-NMe-phenyl-$CH_2$—$CH_2$— |
| 40 | 4-iPrCO—NH-phenyl-$CH_2$—$CH_2$— |
| 41 | 4-iPrCO—NMe-phenyl-$CH_2$—$CH_2$— |
| 42 | 2-iPrCO—NH-phenyl-$CH_2$—$CH_2$— |
| 43 | 2-iPrCO—NMe-phenyl-$CH_2$—$CH_2$— |
| 44 | 4-MeOOC—NH-phenyl-$CH_2$—$CH_2$— |
| 45 | 4-MeOOC—NMe-phenyl-$CH_2$—$CH_2$— |
| 46 | 4-$EtSO_2$—NH-phenyl-$CH_2$—$CH_2$— |
| 47 | 3-$EtSO_2$—NH-phenyl-$CH_2$—$CH_2$— |
| 48 | 4-$NH_2$-phenyl-CH(Me)— |
| 49 | 3-$NH_2$-phenyl-CH(Me)— |
| 50 | 4-$NH_2$-phenyl-CH(Me)—$CH_2$— |
| 51 | 3-$NH_2$-phenyl-CH(Me)—$CH_2$— |
| 52 | 4-$EtSO_2$—N(COOEt)-phenyl-$CH_2$—$CH_2$— |
| 53 | 4-$MeSO_2$—N(COOiPr)-phenyl-$CH_2$—$CH_2$— |
| 54 | 4-$Me_2$NCO—NH-phenyl-$CH_2$— |
| 55 | 4-$H_2$C═CHOCO—NH-phenyl-$CH_2$—$CH_2$— |
| 56 | 4-NC—$CH_2$—CO—NH-phenyl-$CH_2$—$CH_2$— |
| 57 | 4-NC—$CH_2$—$CH_2$—CO—NMe-phenyl-$CH_2$—$CH_2$— |
| 58 | 4-Cbu-CO—NMe-phenyl-$CH_2$—$CH_2$— |
| 59 | 4-MeNHCS—NH-phenyl-$CH_2$—$CH_2$— |
| 60 | 4-NC—$CH_2$—$CH_2$—O—CO—NEt—phenyl-$CH_2$—$CH_2$— |
| 61 | 3-Br-pyrid-5-yl-$CH_2$—$CH_2$— |
| 62 | 2-Cl-thiazol-5-yl-CHMe— |
| 63 | 4-Cbu-CO—N($SO_2$Et)-phenyl-$CH_2$—$CH_2$— |
| 64 | 4-ChxNHCO—NH-phenyl-$CH_2$—$CH_2$— |
| 65 | 4-iPrCO—N($SO_2$Et)-phenyl-$CH_2$—$CH_2$— |
| 66 | 4-sec-BuCO—NMe-phenyl-$CH_2$—$CH_2$— |
| 67 | 4-MCpr-CO—N($SO_2$Et)-phenyl-$CH_2$—$CH_2$— |
| 68 | 4-MCpr-CO—N($SO_2$iPr)-phenyl-$CH_2$—$CH_2$— |
| 69 | 4-MCpr-CO—N(COOPr)-phenyl-$CH_2$—$CH_2$— |
| 70 | 2-CprNH-pyrid-5-yl-$CH_2$— |

Boc = tert-Butyloxycarbonyl,
Cpr = Cyclopropyl,
Cbu = Cyclobutyl,
Chx = Cyclohexyl,
MCpr = 1-methyl-cycloprop-1-yl,
Ph = Phenyl Group 2

Compounds of Group 2 correspond to the general formula (I), in which A-B stands for the group $—HC{=}C(CH_3)—$, $R^1$ and $R^3$ stand for hydrogen, X stands for O and $R^2$ has one of the meanings listed Table 1.

Group 3

Compounds of Group 3 correspond to the general formula (I), in which A-B stands for the group $—H_2—CH_2—$, $R^1$ and $R^3$ stand for hydrogen, X stands for O and $R^2$ has one of the meanings listed in Table 1.

Group 4

Compounds of Group 4 correspond to the general formula (I), in which A-B stands for the group $—H_2C—CH(CH_3)—$, $R^1$ and $R^3$ stand for hydrogen, X stands for O and $R^2$ has one of the meanings listed in Table 1.

Group 5

Compounds of Group 5 correspond to the general formula (I), in which A-B stands for the group $—HC{=}CH—$, $R^1$ stands for hydrogen, $R^3$ stands for hydroxy, X stands for O and $R^2$ has one of the meanings listed in Table 1.

Group 6

Compounds of Group 6 correspond to the general formula (I), in which A-B stands for the group $—HC{=}C(CH_3)—$, $R^1$ stands for hydrogen, $R^3$ stands for hydroxy, X stands for O and $R^2$ has one of the meanings listed in Table 1.

Group 7

Compounds of Group 7 correspond to the general formula (I), in which A-B stands for the group $—H_2C—CH_2—$, $R^1$ stands for hydrogen, $R^3$ stands for hydroxy, X stands for O and $R^2$ has one of the meanings listed in Table 1.

Group 8

Compounds of Group 8 correspond to the general formula (I), in which A-B stands for the group $—H_2C—CH(CH_3)—$, $R^1$ stands for hydrogen, $R^3$ stands for hydroxy, X stands for O and $R^2$ is one the compounds listed in Table 1.

Group 9

Compounds of Group 9 correspond to the general formula (I), in which A-B stands for the group $—HC{=}CH—$, $R^1$ stands for an amino sugar shown in formula 1a 1a

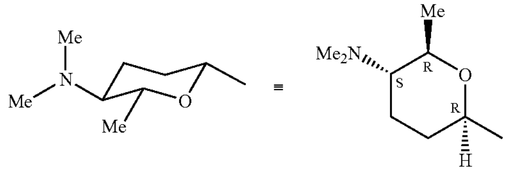

$R^3$ stands for hydrogen, X stands for O and $R^2$ has one of the meanings listed in Table 1.

Group 10

Compounds of Group 10 correspond to the general formula (I), in which A-B stands for the group $—HC{=}C(CH_3)—$, $R^1$ stands for an amino sugar shown in formula 1a 1a

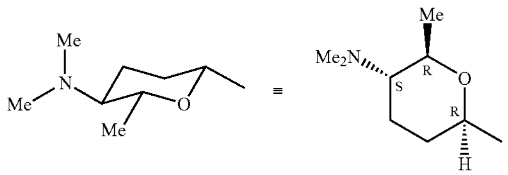

$R^3$ stands for hydrogen, X stands for O and $R^2$ has one of the meanings listed in Table 1.

Group 11

Compounds of Group 11 correspond to the general formula (I), in which A-B stands for the group $—H_2C—CH_2—$, $R^1$ stands for an amino sugar shown in formula 1a 1a

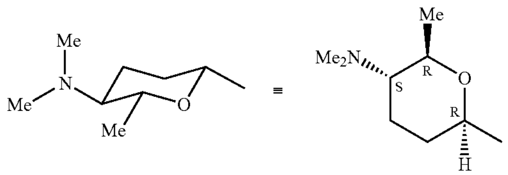

$R^3$ stands for hydrogen, X stands for O and $R^2$ has one of the meanings listed in Table 1.

Group 12

Compounds of Group 12 correspond to the general formula (I), in which A-B stands for the group $—H_2C—CH(CH_3)—$, $R^1$ stands for an amino sugar shown in formula 1a 1a

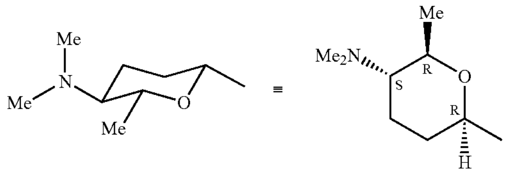

$R^3$ stands for hydrogen, X stands for O and $R^2$ has one of the meanings listed in Table 1.

Group 13

Compounds of Group 13 correspond to the general formula (I), in which A-B stands for the group $—HC{=}CH—$, $R^1$ stands for an amino sugar shown in formula 1b 1b

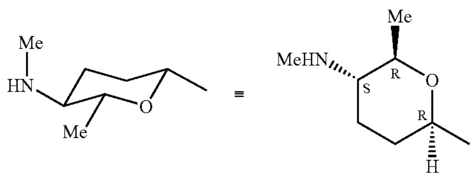

$R^3$ stands for hydrogen, X stands for O and $R^2$ has one of the meanings listed in Table 1.

Group 14

Compounds of Group 14 correspond to the general formula (I), in which A-B stands for the group —HC═C($CH_3$)—, $R^1$ stands for an amino sugar shown in formula 1b 1b

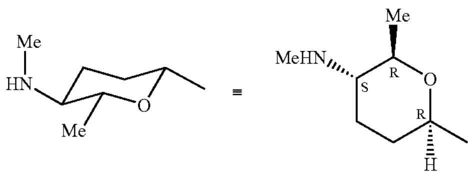

$R^3$ stands for hydrogen, X stands for O and $R^2$ has one of the meanings listed in Table 1.

Group 15

Compounds of Group 15 correspond to the general formula (I), in which A-B stands for the group —$H_2C$—$CH_2$—, $R^1$ stands for an amino sugar shown in formula 1b 1b

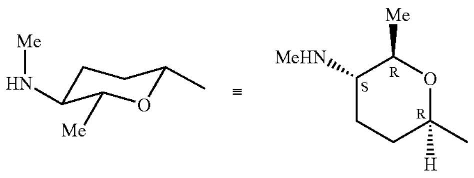

$R^3$ stands for hydrogen, X stands for O and $R^2$ has one of the meanings listed in Table 1.

Group 16

Compounds of Group 16 correspond to the general formula (I), in which A-B stands for the group —$H_2C$—CH($CH_3$)—, $R^1$ stands for an amino sugar shown in formula 1b 1b

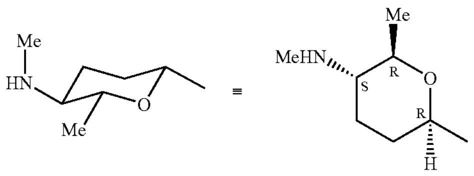

$R^3$ stands for hydrogen, X stands for O and $R^2$ has one of the meanings listed in Table 1.

Group 17

Compounds of Group 17 correspond to the general formula (I), in which A-B stands for the group —HC═CH—, $R^1$ stands for an amino sugar shown in formula 1c 1c

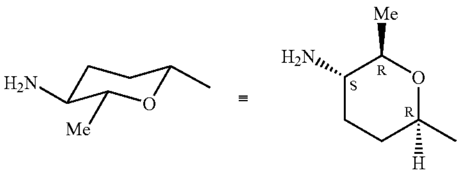

$R^3$ stands for hydrogen, X stands for O and $R^2$ has one of the meanings shown in Table 1.

Group 18

Compounds of Group 18 correspond to the general formula (I), in which A-B stands for the group —$H_2C$—CH($CH_3$)—, $R^1$ stands for an amino sugar shown in formula 1c 1c

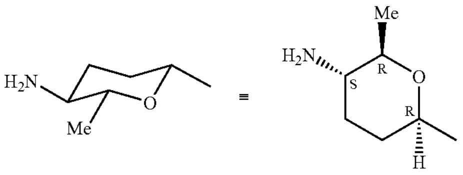

$R^3$ stands for hydrogen, X stands for O and $R^2$ has one of the meanings listed in Table 1.

Group 19

Compounds of Group 19 correspond to the general formula (I), in which A-B stands for the group —$H_2C$—$CH_2$—, $R^1$ stands for an amino sugar shown in formula 1c 1c

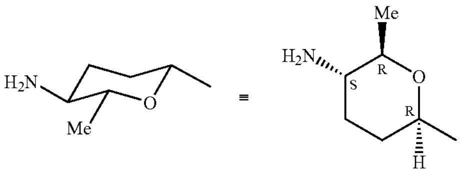

$R^3$ stands for hydrogen, X stands O and $R^2$ has one of the meanings listed in Table 1.

Group 20

Compounds of Group 20 correspond to the general formula (I), in which A-B stands for the group —$H_2C$—CH($CH_3$)—, $R^1$ stands for an amino sugar shown in formula 1c 1c

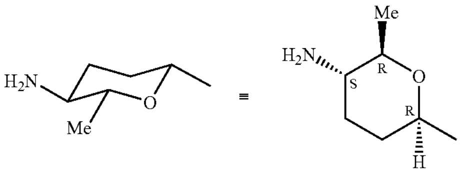

$R^3$ stands for hydrogen, X stands O and $R^2$ has one of the meanings listed in Table 1.

Group 21

Compounds of Group 21corresponds to the general formula (I), in which A-B stands for a group —HC═CH—, $R^1$ stands for an amino sugar shown in formula 1d 1d

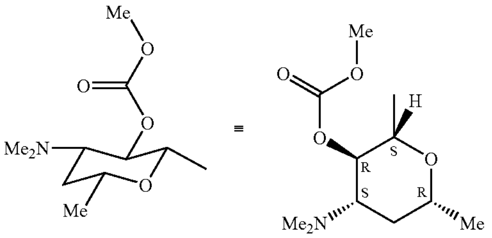

$R^3$ stands for hydrogen, X stands O and $R^2$ has one of the meanings listed in Table 1.

Group 22

Compounds of Group 22 correspond to the general formula (I), in which A-B stands for the group —HC═C($CH_3$)—, $R^1$ stands for an amino sugar shown in formula 1d 1d

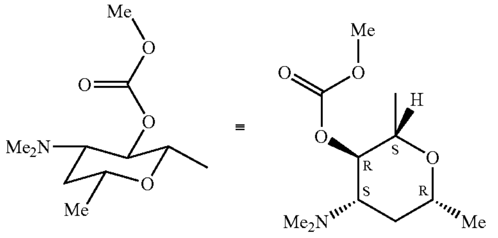

$R^3$ stands for hydrogen, X stands O and $R^2$ has one of the meanings listed in Table 1.

Group 23

Compounds of Group 23 correspond to the general formula (I), in which A-B stands for the group —$H_2C$—$CH_2$—, $R^1$ stands for an amino sugar shown in formula 1d 1d

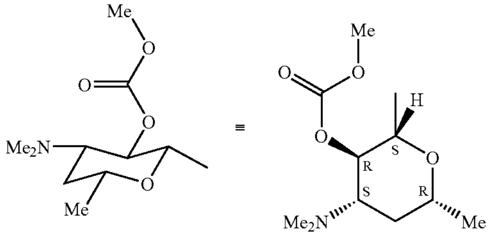

$R^3$ stands for hydrogen, X stands O and $R^2$ has one of the meanings listed in Table 1.

Group 24

Compounds of Group 24 correspond to the general formula (I), in which A-B stands for the group —$H_2C$—CH($CH_3$)—, $R^1$ stands for an amino sugar shown in formula 1d 1d

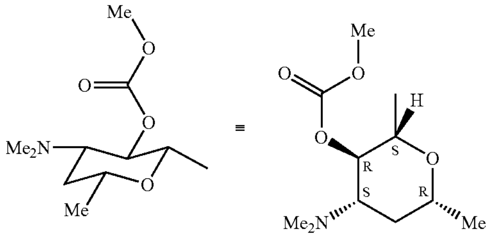

$R^3$ stands for hydrogen, X stands O and $R^2$ has one of the meanings listed in Table 1.

Group 25

Compounds of Group 25 correspond to the general formula (I), in which A-B stands for the group —HC═CH—, $R^1$ stands for an amino sugar shown in formula 1e 1e

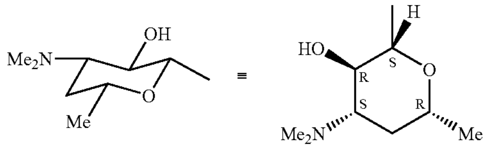

$R^3$ stands for hydrogen, X stands O and $R^2$ has one of the meanings listed in Table 1.

Group 26

Compounds of Group 26 correspond to the general formula (I), in which A-B stands for the group —HC═C($CH_3$)—, $R^1$ stands for an amino sugar shown in formula 1e 1e

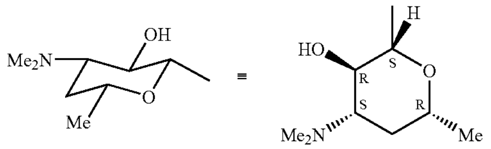

$R^3$ stands for hydrogen, X stands O and $R^2$ has one of the meanings listed in Table 1.

Group 27

Compounds of Group 27 correspond to the general formula (I), in which A-B stands for the group —$H_2C$—$CH_2$—, $R^1$ stands for an amino sugar shown in formula 1e 1e

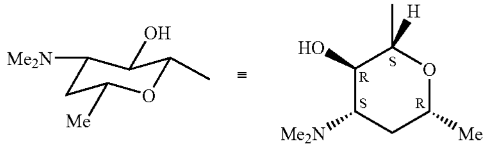

$R^3$ stands for hydrogen, X stands O and $R^2$ has one of the meanings listed in Table 1.

Group 28

Compounds of Group 28 correspond to the general formula (I), in which A-B stands for the group —$H_2C$—CH($CH_3$)—, $R^1$ stands for an amino sugar shown in formula 1e 1e

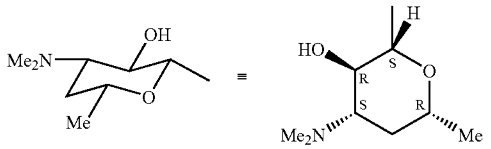

$R^3$ stands for hydrogen, X stands O and $R^2$ has one of the meanings listed in Table 1.

Group 29

Compounds of Group 29 correspond to the general formula (I), in which A-B stands for the group —HC═CH—, $R^1$ stands for an amino sugar shown in formula 1f 1f

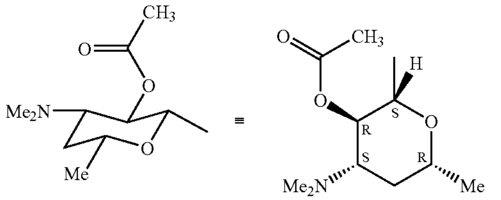

$R^3$ stands for hydrogen, X stands O and $R^2$ has one of the meanings listed in Table 1.

Group 30

Compounds of Group 30 correspond to the general formula (I), in which A-B stands for the group —HC═C($CH_3$)—, $R^1$ stands for an amino sugar shown in formula 1f 1f

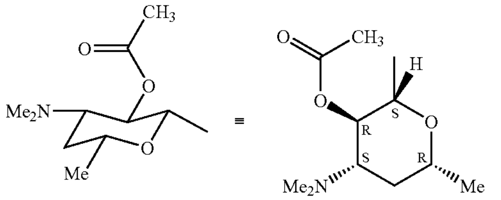

$R^3$ stands for hydrogen, X stands O and $R^2$ has one of the meanings listed in Table 1.

Group 31

Compounds of Group 31 correspond to the general formula (I), in which A-B stands for the group —$H_2C$—$CH_2$—, $R^1$ stands for an amino sugar shown in formula 1f 1f

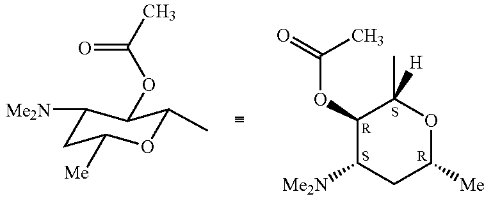

$R^3$ stands for hydrogen, X stands O and $R^2$ has one of the meanings listed in Table 1.

Group 32

Compounds of Group 32 correspond to the general formula (I), in which A-B stands for the group —$H_2C$—CH($CH_3$)—, $R^1$ stands for an amino sugar shown in formula 1f 1f

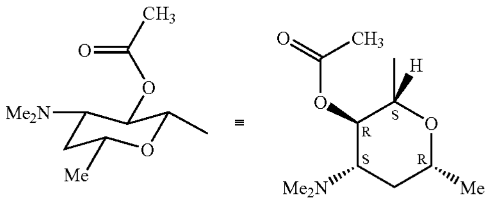

$R^3$ stands for hydrogen, X stands O and $R^2$ has one of the meanings listed in Table 1.

Group 33

Compounds of Group 33 correspond to the general formula (I), in which A-B stands for the group —HC═CH—, $R^1$ stands for an amino sugar shown in formula 1g 1g

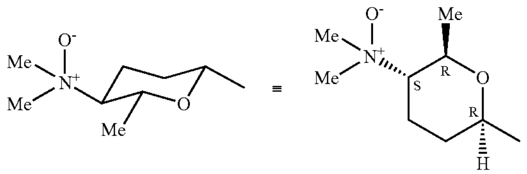

$R^3$ stands for hydrogen, X stands O and $R^2$ has one of the meanings listed in Table 1.

Group 34

Compounds of Group 34 correspond to the general formula (I), in which A-B stands for the group —HC═C($CH_3$)—, $R^1$ stands for an amino sugar shown in formula 1g 1g

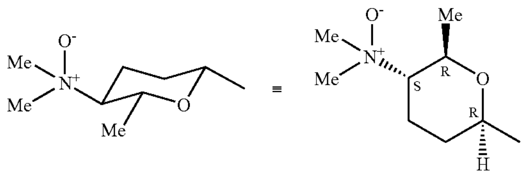

$R^3$ stands for hydrogen, X stands O and $R^2$ has one of the meanings listed in Table 1.

Group 35

Compounds of Group 35 correspond to the general formula (I), in which A-B stands for the group —$H_2C$—$CH_2$—, $R^1$ stands for an amino sugar shown in formula 1g 1g

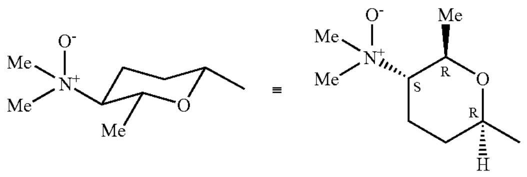

$R^3$ stands for hydrogen, X stands O and $R^2$ has one of the meanings listed in Table 1.

Group 36

Compounds of Group 36 correspond to the general formula (I), in which A-B stands for the group —$H_2C$—CH($CH_3$)—, $R^1$ stands for an amino sugar shown in formula 1g 1g

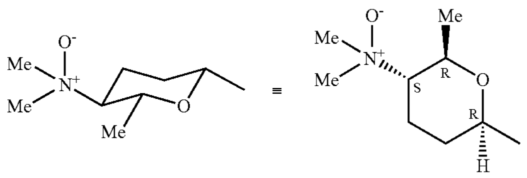

$R^3$ stands for hydrogen, X stands O and $R^2$ has one of the meanings listed in Table 1.

Group 37

(I)

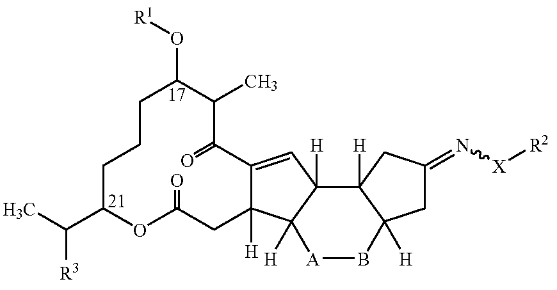

and derived salts,

Compounds of Group 37 correspond to the general formula (I), in which A-B stands for the group —HC═CH—, $R^1$ and $R^3$ stand for hydrogen, X stands for NH and $R^2$ stands for a moiety as listed in Table 2 below:

TABLE 2

| Comp. No. | $R^2$ |
|---|---|
| 1 | 4-$NH_2$-phenyl-$CH_2$—$CH_2$— |
| 2 | 4-Cpr-CO—NH-phenyl-$CH_2$—$CH_2$— |
| 3 | 4-Cpr-CO—NMe-phenyl-$CH_2$—$CH_2$— |
| 4 | 4-Cpr-CO—NEt-phenyl-$CH_2$—$CH_2$— |
| 5 | 3-$NH_2$-phenyl-$CH_2$—$CH_2$— |
| 6 | 3-Cpr-CO—NH-phenyl-$CH_2$—$CH_2$— |
| 7 | 4-Cbu-CO—NMe-phenyl-$CH_2$—$CH_2$— |
| 8 | 3-Cpr-CO—NEt-phenyl-$CH_2$—$CH_2$— |
| 9 | 4-MCpr-CO—NH-phenyl-$CH_2$—$CH_2$— |
| 10 | 4-MCpr-CO—NMe-phenyl-$CH_2$—$CH_2$— |
| 11 | 4-MCpr-CO—NEt-phenyl-$CH_2$—$CH_2$— |
| 12 | 4-Ph-O-phenyl-$CH_2$—$CH_2$— |
| 13 | 4-$MeSO_2$—NH-phenyl-$CH_2$—$CH_2$— |
| 14 | 3-$MeSO_2$—NH-phenyl-$CH_2$—$CH_2$— |
| 15 | 2-chloro-pyrid-5-yl-$CH_2$— |
| 16 | 2-chloro-pyrid-5-yl-$CH_2$—$CH_2$— |
| 17 | $H_2N$—CS |
| 18 | Me—HN—CS |
| 19 | 4-$CF_3O$-phenyl-NH—CO— |
| 20 | 4-$CF_3$-phenyl-NH—CO— |
| 21 | 4-Cl-phenyl-NH—CO— |
| 22 | 3-$CF_3O$-phenyl-NH—CO— |
| 23 | 3-$CF_3$-phenyl-NH—CO— |
| 24 | 2-chloro-pyrid-5-yl-CHMe— |
| 25 | 4-Boc-NH-phenyl-$CH_2$—$CH_2$— |
| 26 | 4-Boc-NMe-phenyl-$CH_2$—$CH_2$— |
| 27 | 3-Boc-NH-phenyl-$CH_2$—$CH_2$— |
| 28 | 3-Boc-NMe-phenyl-$CH_2$—$CH_2$— |
| 29 | 4-iPrCO—NH-phenyl-$CH_2$—$CH_2$— |
| 30 | 4-iPrCO—NMe-phenyl-$CH_2$—$CH_2$— |
| 31 | 4-iPrCO—NH-phenyl-$CH_2$— |
| 33 | 4-iPrCO—NMe-phenyl-$CH_2$— |

Boc = tert-Butyloxycarbonyl,
Cpr = Cyclopropyl,
Cbu = Cyclobutyl,
MCpr = 1-methyl-cyclopropl-yl,
Ph = Phenyl Group 38

Compounds of Group 38 correspond to the general formula (I), in which A-B stands for the group —HC═C($CH_3$)—, $R^1$ and $R^3$ stand for hydrogen, X stands for NH and $R^2$ has one of the meanings listed in Table 2.

Group 39

Compounds of Group 39 correspond to the general formula (I), in which A-B stands for the group —$H_2C$—$CH_2$—, $R^1$ and $R^3$ stand for hydrogen, X stands for NH and $R^2$ has one of the meanings listed in Table 2.

Group 40

Compounds of Group 40 correspond to the general formula (I), in which A-B stands for the group —$H_2C$—CH($CH_3$)—, $R^1$ and $R^3$ stand for hydrogen, X stands for NH and $R^2$ has one of the meanings listed in Table 2.

Group 41

Compounds of Group 41 correspond to the general formula (I), in which A-B stands for the group —HC═CH—, $R^1$ and $R^3$ stand for hydrogen, X stands for NEt and $R^2$ has one of the meanings listed in Table 2.

Group 42

Compounds of Group 42 correspond to the general formula (I), in which A-B stands for the group —HC═C($CH_3$)—, $R^1$ and $R^3$ stand for hydrogen, X stands for NEt and $R^2$ has one of the meanings listed in Table 2.

Group 43

Compounds of Group 43 correspond to the general formula (I), in which A-B stands for the group —$H_2C$—$CH_2$—, $R^1$ and $R^3$ stand for hydrogen, X stands for NEt and $R^2$ has one of the meanings listed in Table 2.

Group 44

Compounds of Group 44 correspond to the general formula (I), in which A-B stands for the group —$H_2C$—CH($CH_3$)—, $R^1$ stands for hydrogen, $R^3$ stands for hydroxy, X stands for NEt and $R^2$ has one of the meanings listed in Table 2.

Group 45

Compounds of Group 45 correspond to the general formula (I), in which A-B stands for the group —HC═CH—, $R^1$ stands for an amino sugar shown in formula 1a 1a

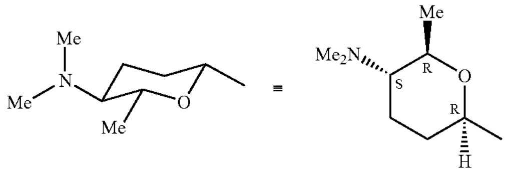

$R^3$ stands for hydrogen, X stands for NH and $R^2$ has one of the meanings listed in Table 2.

Group 46

Compounds of Group 46 correspond to the general formula (I), in which A-B stands for the group —HC═C($CH_3$)—, $R^1$ stands for an amino sugar shown in formula 1a 1a

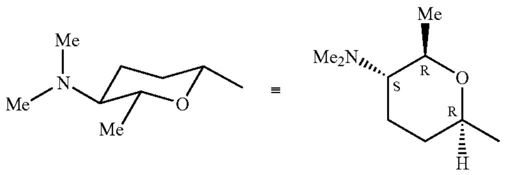

$R^3$ stands for hydrogen, X stands for NH and $R^2$ has one of the meanings listed in Table 2.

Group 47

Compounds of Group 47 correspond to the general formula (I), in which A-B stands for the group —$H_2C$—$CH_2$—, $R^1$ stands for an amino sugar shown in formula 1a 1a

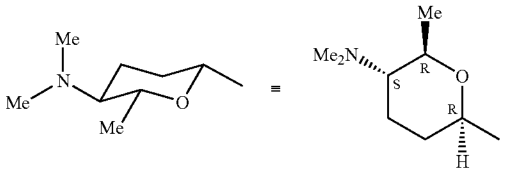

$R^3$ stands for hydrogen, X stands for NH and $R^2$ has one of the meanings listed in Table 2.

Group 48

Compounds of Group 48 correspond to the general formula (I), in which A-B stands for the group —$H_2C$—CH($CH_3$)—, $R^1$ stands for an amino sugar shown in formula 1a 1a

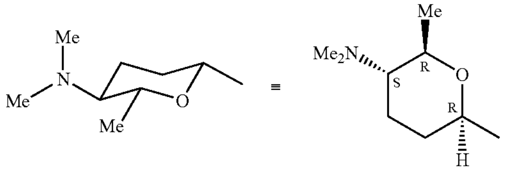

$R^3$ stands for hydrogen, X stands for NH and $R^2$ has one of the meanings listed in Table 2.

Group 49

Compounds of Group 49 correspond to the general formula (I), in which A-B stands for the group —HC═CH—, $R^1$ stands for an amino sugar shown in formula 1b 1b

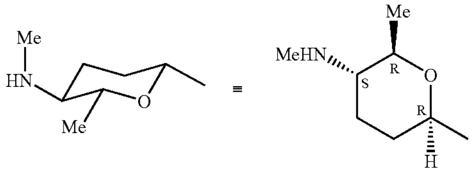

$R^3$ stands for hydrogen, X stands for NH and $R^2$ has one of the meanings listed in Table 2.

Group 50

Compounds of Group 50 correspond to the general formula (I), in which A-B stands for the group —HC═C($CH_3$)—, $R^1$ stands for an amino sugar shown in formula 1b 1b

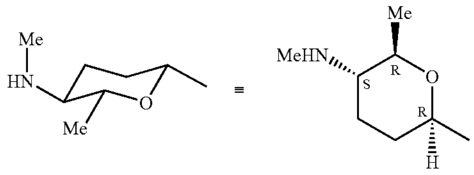

$R^3$ stands for hydrogen, X stands for NH and $R^2$ has one of the meanings listed in Table 2.

Group 51

Compounds of Group 51correspond to the general formula (I), in which A-B stands for the group —$H_2C$—$CH_2$—, $R^1$ stands for an amino sugar shown in formula 1b 1b

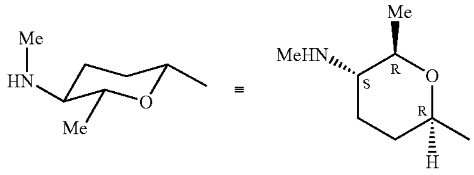

$R^3$ stands for hydrogen, X stands for NH and $R^2$ has one of the meanings listed in Table 2.

Group 52

Compounds of Group 52 correspond to the general formula (I), in which A-B stands for the group —$H_2C$—CH($CH_3$)—, $R^1$ stands for an amino sugar shown in formula 1b 1b

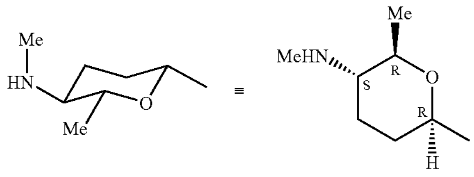

$R^3$ stands for hydrogen, X stands for NH and $R^2$ has one of the meanings listed in Table 2.

Group 53

Compounds of Group 53 correspond to the general formula (I), in which A-B stands for the group —HC═CH—, $R^1$ stands for an amino sugar shown in formula 1c 1c

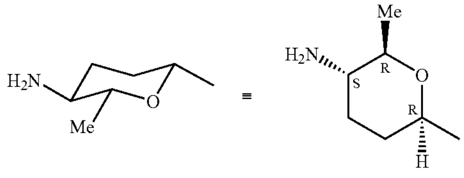

$R^3$ stands for hydrogen, X stands for NH and $R^2$ has one of the meanings listed in Table 2.

Group 54

Compounds of Group 54 correspond to the general formula (I), in which A-B stands for the group —$H_2C$—CH ($CH_3$)—, $R^1$ stands for an amino sugar shown in formula 1c

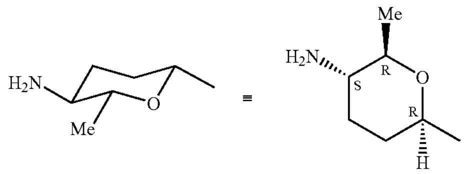

1c $R^3$ stands for hydrogen, X stands for NH and $R^2$ has one of the meanings listed in Table 2.

Group 55

Compounds of Group 55 correspond to the general formula (I), in which A-B stands for the group —HC═CH—, $R^1$ stands for an amino sugar shown in formula 1d

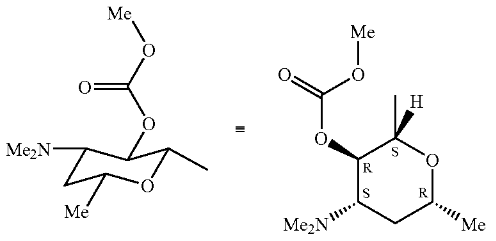

1d $R^3$ stands for hydrogen, X stands for NH and $R^2$ has one of the meanings listed in Table 2.

Group 56

Compounds of Group 56 correspond to the general formula (I), in which A-B stands for the group —HC═C ($CH_3$)—, $R^1$ stands for an amino sugar shown in formula 1d

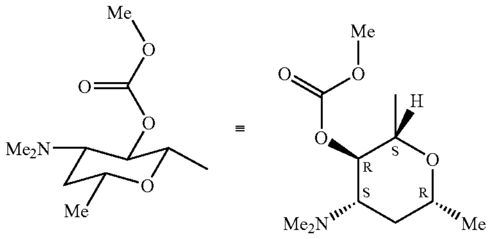

1d $R^3$ stands for hydrogen, X stands for NH and $R^2$ has one of the meanings listed in Table 2.

Group 57

Compounds of Group 57 correspond to the general formula (I), in which A-B stands for the group —$H_2C$—$CH_2$—, $R^1$ stands for an amino sugar shown in formula 1d

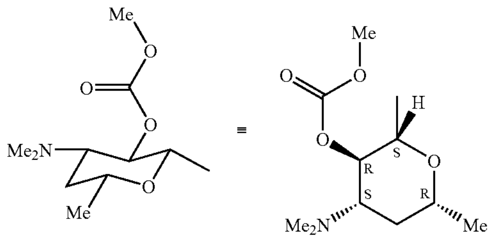

1d $R^3$ stands for hydrogen, X stands for NH and $R^2$ has one of the meanings listed in Table 2.

Group 58

Compounds of Group 58 correspond to the general formula (I), in which A-B stands for the group —$H_2C$—CH ($CH_3$)—, $R^1$ stands for an amino sugar shown in formula 1d

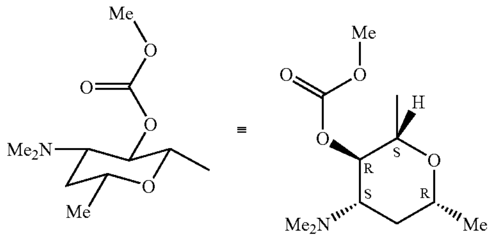

1d $R^3$ stands for hydrogen, X stands for NH and $R^2$ has one of the meanings listed in Table 2.

Group 59

Compounds of Group 59 correspond to the general formula (I), in which A-B stands for the group —HC═CH—, $R^1$ stands for an amino sugar shown in formula 1e

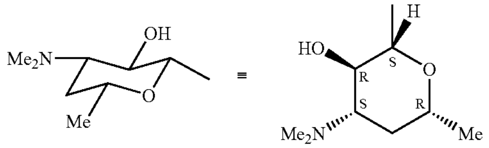

1e $R^3$ stands for hydrogen, X stands for NH and $R^2$ has one of the meanings listed in Table 2.

Group 60

Compounds of Group 60 correspond to the general formula (I), in which A-B stands for the group —HC═C ($CH_3$)—, $R^1$ stands for an amino sugar shown in formula 1e

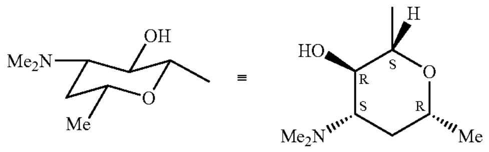

1e $R^3$ stands for hydrogen, X stands for NH and $R^2$ has one of the meanings listed in Table 2.

Group 61

Compounds of Group 61 correspond to the general formula (I), in which A-B stands for the group —$H_2C$—$CH_2$—, $R^1$ stands for an amino sugar shown in formula 1e 1e

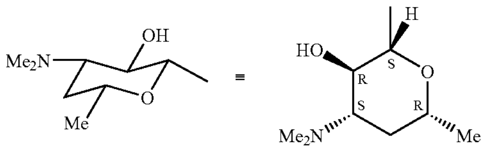

$R^3$ stands for hydrogen, X stands for NH and $R^2$ has one of the meanings listed in Table 2.

Group 62

Compounds of Group 62 correspond to the general formula (I), in which A-B stands for the group —$H_2C$—CH($CH_3$)—, $R^1$ stands for an amino sugar shown in formula 1e 1e

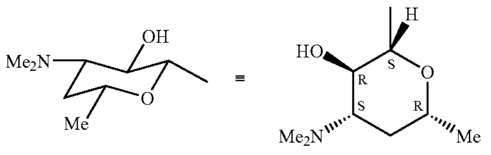

$R^3$ stands for hydrogen, X stands for NH and $R^2$ has one of the meanings listed in Table 2.

Group 63

Compounds of Group 63 correspond to the general formula (I), in which A-B stands for the group —HC═CH—, $R^1$ stands for an amino sugar shown in formula 1f 1f

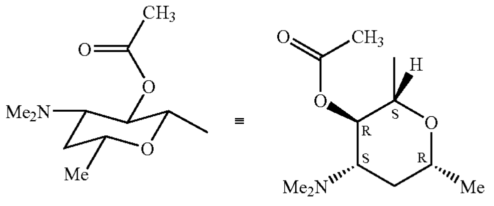

$R^3$ stands for hydrogen, X stands for NH and $R^2$ has one of the meanings listed in Table 2.

Group 64

Compounds of Group 64 correspond to the general formula (I), in which A-B stands for the group —HC═C($CH_3$)—, $R^1$ stands for an amino sugar shown in formula 1f 1f

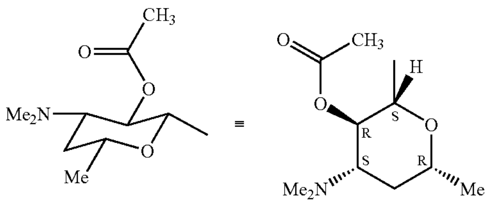

$R^3$ stands for hydrogen, X stands for NH and $R^2$ has one of the meanings listed in Table 2.

Group 65

Compounds of Group 65 correspond to the general formula (I), in which A-B stands for the group —HC═CH—, $R^1$ stands for an amino sugar shown in formula 1g 1g

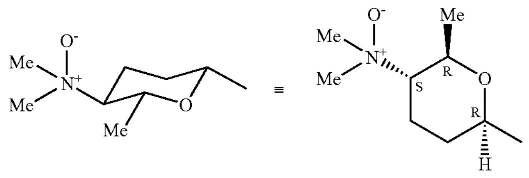

$R^3$ stands for hydrogen, X stands for NH and $R^2$ has one of the meanings listed in Table 2.

Group 66

Compounds of Group 66 correspond to the general formula (I), in which A-B stands for the group —HC═CH—, $R^1$ and $R^3$ stand for hydrogen, X stands for NMe and $R^2$ has one of the meanings listed in Table 2.

Group 67

Compounds of Group 67 correspond to the general formula (I), in which A-B stands for the group —HC═C($CH_3$)—, $R^1$ and $R^3$ stand for hydrogen, X stands for NMe and $R^2$ has one of the meanings listed in Table 2.

Group 68

Compounds of Group 68 correspond to the general formula (D), in which A-B stands for the group —$H_2C$—$CH_2$—, $R^1$ and $R^3$ stand for hydrogen, X stands for NMe and $R^2$ has one of the meanings listed in Table 2.

Group 69

Compounds of Group 69 correspond to the general formula (I), in which A-B stands for the group —$H_2C$—CH($CH_3$)—, $R^1$ and $R^3$ stand for hydrogen, X stands for NMe and $R^2$ has one of the meanings listed in Table 2.

Group 70

Compounds of Group 70 correspond to the general formula (I), in which A-B stands for the group —HC═CH—, $R^1$ stands for hydrogen, $R^3$ stands for hydroxy, X stands for NMe and $R^2$ has one of the meanings listed in Table 2.

Group 71

Compounds of Group 70 correspond to the general formula (I), in which A-B stands for the group —HC═C($CH_3$)—, $R^1$ stands for hydrogen, $R^3$ stands for hydroxy, X stands for NMe and $R^2$ has one of the meanings listed in Table 2.

Group 72

Compounds of Group 72 correspond to the general formula (I), in which A-B stands for the group —$H_2C$—$CH_2$—, $R^1$ stands for hydrogen, $R^3$ stands for hydroxy, X stands for NMe and $R^2$ has one of the meanings listed in Table 2.

Group 73

Compounds of Group 73 correspond to the general formula (I), in which A-B stands for the group —$H_2C$—CH($CH_3$)—, $R^1$ stands for hydrogen, $R^3$ stands for hydroxy, X stands for NMe and $R^2$ has one of the meanings listed in Table 2.

Group 74

Compounds of Group 74 correspond to the general formula (I), in which A-B stands for the group —HC═CH—, $R^1$ stands for an amino sugar shown in formula 1a 1a

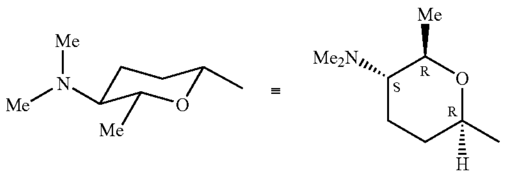

$R^3$ stands for hydrogen, X stands for NMe and $R^2$ has one of the meanings listed in Table 2.

Group 75

Compounds of Group 75 correspond to the general formula (I), in which A-B stands for the group —HC═C(CH$_3$)—, $R^1$ stands for an amino sugar shown in formula 1a 1a

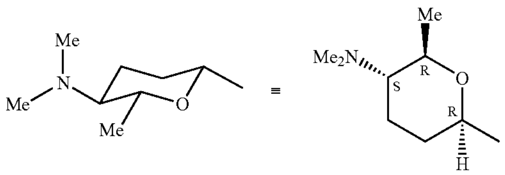

$R^3$ stands for hydrogen, X stands for NMe and $R^2$ has one of the meanings listed in Table 2.

Group 76

Compounds of Group 76 correspond to the general formula (I), in which A-B stands for the group —$H_2C$—$CH_2$—, $R^1$ stands for an amino sugar shown in formula 1a 1a

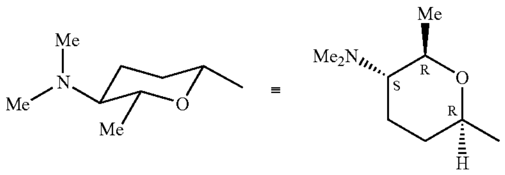

$R^3$ stands for hydrogen, X stands for NMe and $R^2$ has one of the meanings listed in Table 2.

Group 77

Compounds of Group 74 correspond to the general formula (I), in which A-B stands for the group —$H_2C$—CH(CH$_3$)—, $R^1$ stands for an amino sugar shown in formula 1a 1a

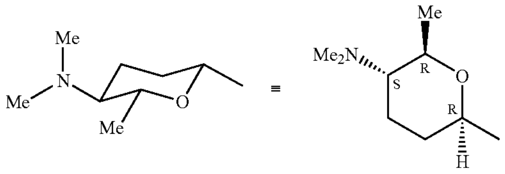

$R^3$ stands for hydrogen, X stands for NMe and $R^2$ has one of the meanings listed in Table 2.

Group 78

Compounds of Group 78 correspond to the general formula (I), in which A-B stands for the group —HC═CH—, $R^1$ stands for an amino sugar shown in formula 1b 1b

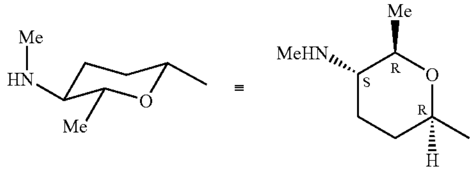

$R^3$ stands for hydrogen, X stands for NMe and $R^2$ has one of the meanings listed in Table 2.

Group 79

Compounds of Group 79 correspond to the general formula (I), in which A-B stands for the group —HC═C(CH$_3$)—, $R^1$ stands for an amino sugar shown in formula 1b 1b

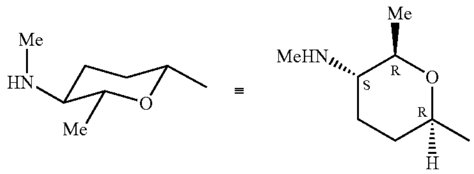

$R^3$ stands for hydrogen, X stands for NMe and $R^2$ has one of the meanings listed in Table 2.

Group 80

Compounds of Group 80 correspond to the general formula (I), in which A-B stands for the group —$H_2C$—$CH_2$—, $R^1$ stands for an amino sugar shown in formula 1b 1b

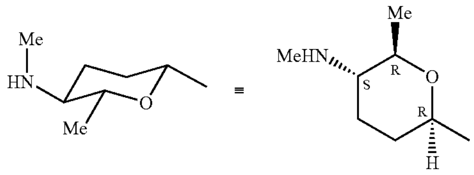

$R^3$ stands for hydrogen, X stands for NMe and $R^2$ has one of the meanings listed in Table 2.

Group 81

Compounds of Group 81correspond to the general formula (I), in which A-B stands for the group —$H_2C$—CH(CH$_3$)—, $R^1$ stands for an amino sugar shown in formula 1b 1b

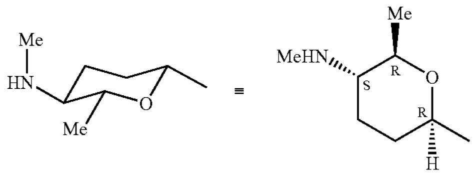

$R^3$ stands for hydrogen, X stands for NMe and $R^2$ has one of the meanings listed in Table 2.

Group 82

Compounds of Group 82 correspond to the general formula (I), in which A-B stands for the group —HC═CH—, $R^1$ stands for an amino sugar shown in formula 1c 1c

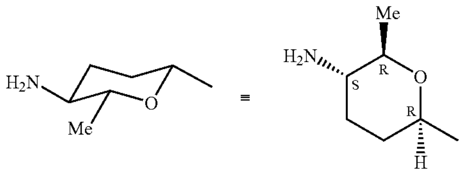

$R^3$ stands for hydrogen, X stands for NMe and $R^2$ has one of the meanings listed in Table 2.

Group 83

Compounds of Group 83 correspond to the general formula (I), in which A-B stands for the group —$H_2C$—CH ($CH_3$)—, $R^1$ stands for an amino sugar shown in formula 1c 1c

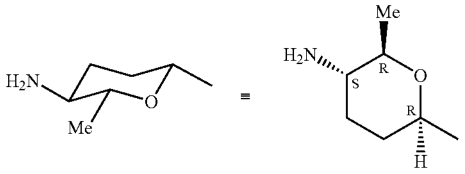

$R^3$ stands for hydrogen, X stands for NMe and $R^2$ has one of the meanings listed in Table 2.

Group 84

Compounds of Group 84 correspond to the general formula (I), in which A-B stands for the group —HC═CH—, $R^1$ stands for an amino sugar shown in formula 1d 1d

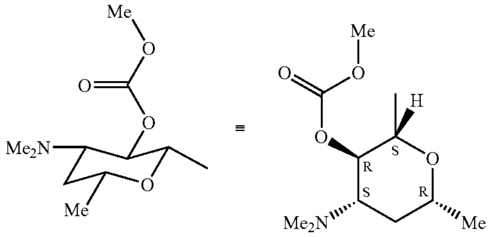

$R^3$ stands for hydrogen, X stands for NMe and $R^2$ has one of the meanings listed in Table 2.

Group 85

Compounds of Group 85 correspond to the general formula (I), in which A-B stands for the group —HC═C ($CH_3$)—, $R^1$ stands for an amino sugar shown in formula 1d 1d

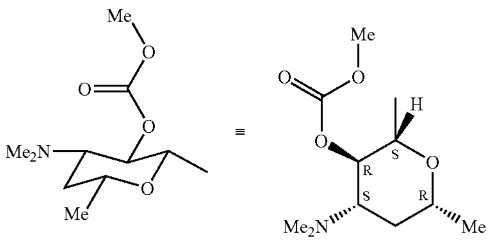

$R^3$ stands for hydrogen, X stands for NMe and $R^2$ has one of the meanings listed in Table 2.

Group 86

Compounds of Group 86 correspond to the general formula (I), in which A-B stands for the group —$H_2C$—$CH_2$—, $R^1$ stands for an amino sugar shown in formula 1d 1d

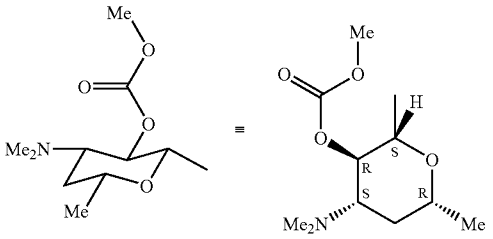

$R^3$ stands for hydrogen, X stands for NMe and $R^2$ has one of the meanings listed in Table 2.

Group 87

Compounds of Group 87 correspond to the general formula (I), in which A-B stands for the group —$H_2C$—CH ($CH_3$)—, $R^1$ stands for an amino sugar shown in formula 1d 1d

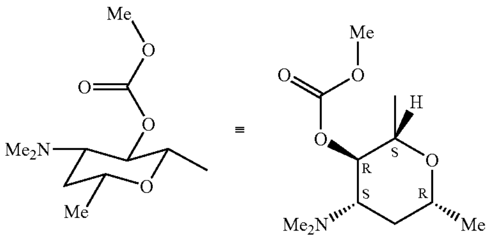

$R^3$ stands for hydrogen, X stands for NMe and $R^2$ has one of the meanings listed in Table 2.

Group 88

Compounds of Group 88 correspond to the general formula (I), in which A-B stands for the group —HC═CH—, $R^1$ stands for an amino sugar shown in formula 1e 1e

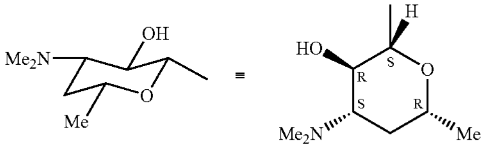

$R^3$ stands for hydrogen, X stands for NMe and $R^2$ has one of the meanings listed in Table 2.

Group 89

Compounds of Group 89 correspond to the general formula (I), in which A-B stands for the group —HC═C ($CH_3$)—, $R^1$ stands for an amino sugar shown in formula 1e 1e

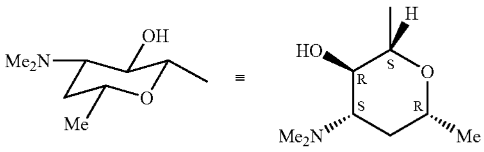

$R^3$ stands for hydrogen, X stands for NMe and $R^2$ has one of the meanings listed in Table 2.

Group 90

Compounds of Group 90 correspond to the general formula (I), in which A-B stands for the group —$H_2C$—$CH_2$—, $R^1$ stands for an amino sugar shown in formula 1e 1e

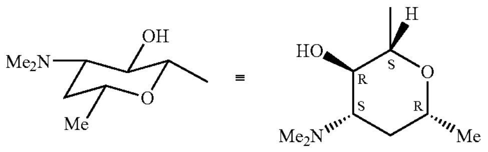

$R^3$ stands for hydrogen, X stands for NMe and $R^2$ has one of the meanings listed in Table 2.

Group 91

Compounds of Group 91 correspond to the general formula (I), in which A-B stands for the group —$H_2C$—CH($CH_3$)—, $R^1$ stands for an amino sugar shown in formula 1e 1e

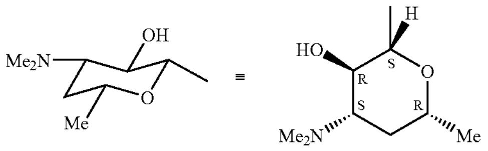

$R^3$ stands for hydrogen, X stands for NMe and $R^2$ has one of the meanings listed in Table 2.

Group 92

Compounds of Group 92 correspond to the general formula (I), in which A-B stands for the group —HC═CH—, $R^1$ stands for an amino sugar shown in formula 1f 1f

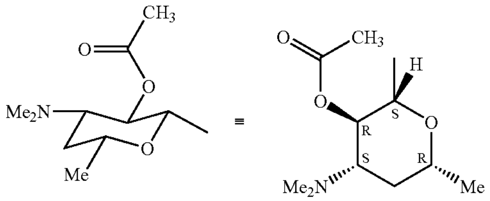

$R^3$ stands for hydrogen, X stands for NMe and $R^2$ has one of the meanings listed in Table 2.

Group 93

Compounds of Group 93 correspond to the general formula (I), in which A-B stands for the group —HC═C($CH_3$)—, $R^1$ stands for an amino sugar shown in formula 1f 1f

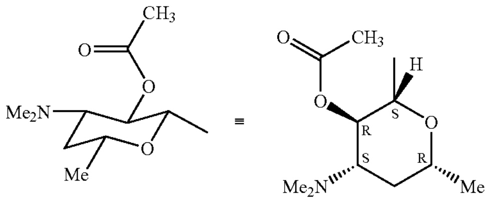

$R^3$ stands for hydrogen, X stands for NMe and $R^2$ has one of the meanings listed in Table 2.

Group 94

Compounds of Group 94 correspond to the general formula (I), in which A-B stands for the group —HC═CH—, $R^1$ stands for an amino sugar shown in formula 1g 1g

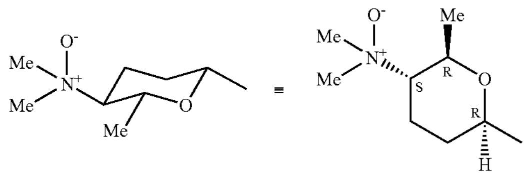

$R^3$ stands for hydrogen, X stands for NMe and $R^2$ has one of the meanings listed in Table 2.

Another subject of the present invention is a method for the manufacture of the new 9-keto spinosyn derivatives according to the general formula (I), (I)

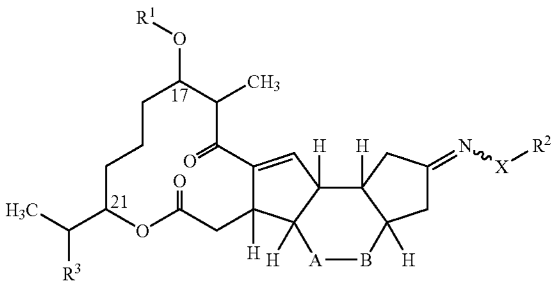

and derived salts, where $R^1$, $R^2$, $R^3$, X and A-B have the meanings indicated previously, in which the 9-keto spinosyn derivatives according to the general formula (II)

(II)

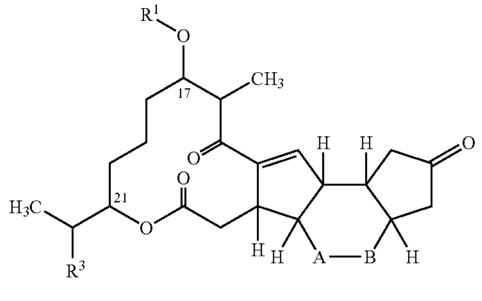

where $R^1$, $R^3$ and A-B have the meanings indicated previously, are reacted with amino compounds according to the general formula (III)

$$H_2N—X—R^2 \quad (III)$$

where $R^2$ and X have the meanings indicated previously, in the presence of a basic additive and possibly in the presence of a diluent.

Methods for the introduction of possibly substituted imino functions are sufficiently known from literature (see A. Lachman, Org. Synth., Coll. Vol. II, 1943, p. 70; W. L. Semon, Org. Synth., Coll. Vol. 1, 1941, p. 318; Houben-Weyl, Methoden der Organischen Chemie (Methods of Organic Chemistry), Bd. X/4, G. Thieme Verlag, Stuttgart New York, p. 55).

to the general formula (II) and O-(4-phenoxy-benzyl)-hydroxylamine (X═O, $R^2$: —$CH_2$—$C_6H_4$—O—$C_6H_5$) is utilised as a compound according to the general formula (III) for the manufacture of the new 9-keto spinosyn derivatives according to the general formula (I) according to the invention-related method, the method can be shown by the following reaction diagram in FIG. 1:

FIG. 1

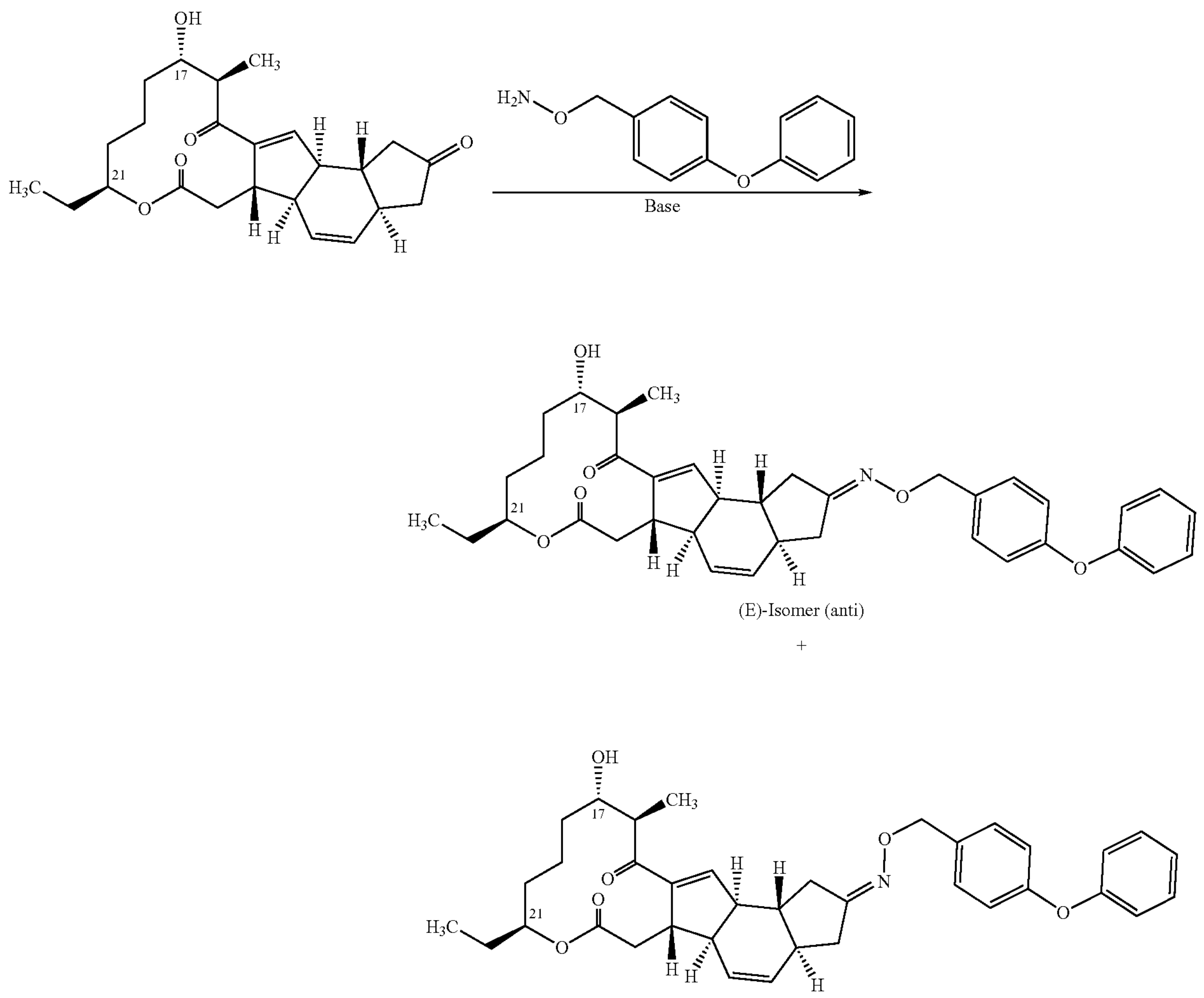

(E)-Isomer (anti)

+

(Z)-Isomer (syn)

It was then surprisingly found that the new 9-keto spinosyn derivatives according the the invention according to the general formula (I) could also be obtained via carbonyl reaction from corresponding 9-keto spinosyn derivatives with amino compounds according to the general formula (II).

In the following section, the method according to the invention will be explained on the basis of selected examples (also see Examples of Manufacture).

If 9-keto spinosyn A-aglycone ($R^1$═—H, $R^3$═—H, A-B═—HC═CH—) is utilised as a compound according If 17-β-desosaminyl-9-keto spinosyn A-aglycone ($R^1$=D-desosaminyl, $R^3$═—H, A-B═—HC═CH—) is utilised as a compound according to the general formula (II) and O-(4-amino-benzyl)-hydroxylamine (X═O, $R^2$: —$CH_2$—$C_6H_4$—$NH_2$) is utilised as a compound according to the general formula (III) in another embodiment of the method according to the invention for the manufacture of the new 9-keto spinosyn derivatives according to the general formula (I), the method can be shown by the following reaction diagram in FIG. 2:

FIG. 2

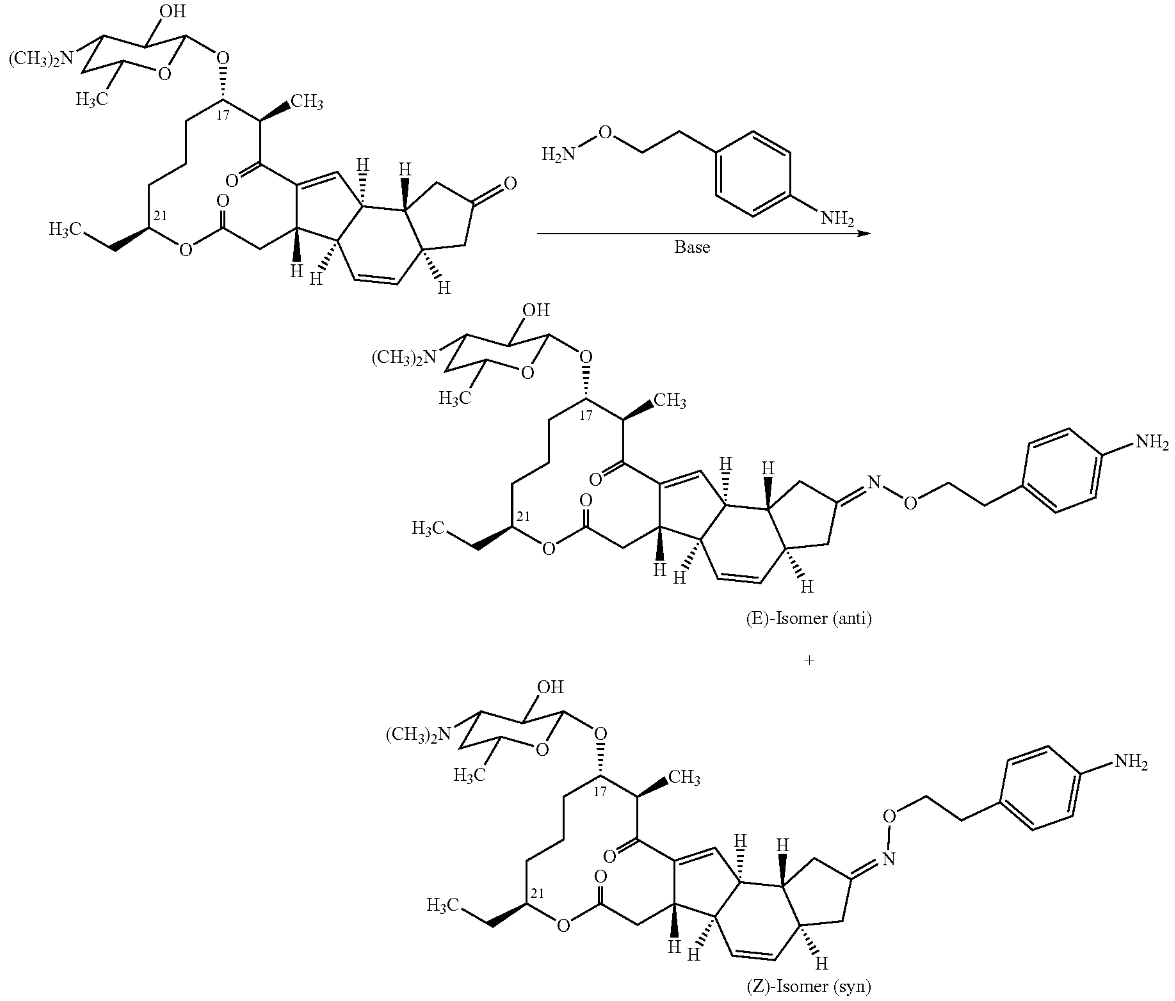

With the use of the amino compounds according to the general formula (III) in the method according to the invention, the compounds according to the general formula (Ia) can occur as a mixture of the (E)-isomer (anti form) and (Z)-isomer (syn form).

If 9-keto spinosyn A-aglycone ($R^1$=—H, $R^3$=—H, A-B=—HC=CH—) is utilised as a compound according to the general formula (II) and N-(4-trifluoromethoxy-phenyl-semicarbazide (X=NH, $R^2$=—CO—NH—$C_6H_4$—$OCF_3$) is utilised as a compound according to the general formula (III) in another embodiment of the method according to the invention for the manufacture of the new 9-keto spinosyn derivatives according to the general formula (I), the method can be shown by the following reaction diagram in FIG. 3:

FIG. 3

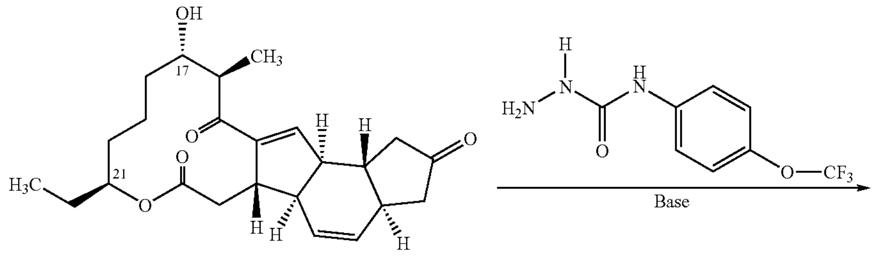

-continued

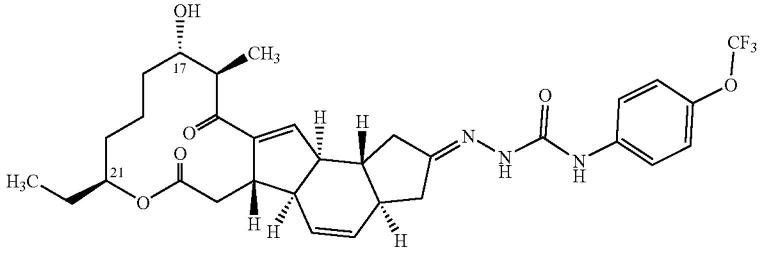

(E)-Isomer (anti)

+

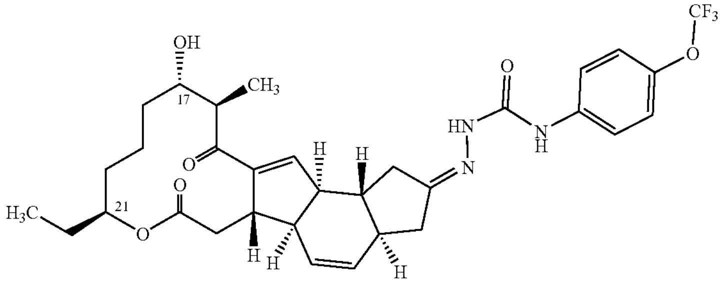

(Z)-Isomer (syn)

With the use of the amino compounds according to the general formula (III) in the method according to the invention, the compounds according to the general formula (Ia) can occur as a mixture of the (E)-isomer (anti form) and (Z)-isomer (syn form).

The 9-keto spinosyn derivatives required as initial substances for performing the method according to the invention are generally defined by formula (II).

In formula (II), $R^1$ and A-B preferably stand for the moieties, which were already mentioned, in conjunction with the description of the compounds according to the invention according to the general formula (I), as being preferred for this substituent or the group.

The 9-keto spinosyn derivatives according to the general formula (II) used as initial substances, where $R^3$ stands for hydrogen, are known from a previous patent, and can be respectively obtained via selective oxidation using chemical and biochemical methods (see WO 02/079184).

The 9-keto spinosyn derivatives according to the general formula (II) used as initial substances, in which $R^3$ stands for hydroxy, can be obtained via selective and/or stereospecific hydroxylation, for example, i.e. by way of bioconversion using suitable microorganisms or their enzymes.

In particular, compounds according to the general formula (IIa)

(IIa)

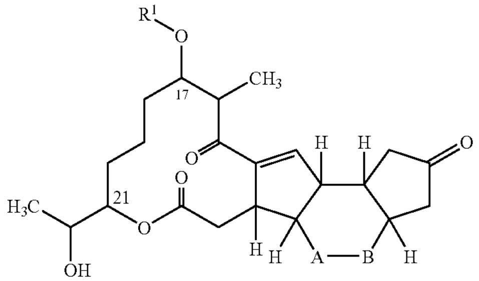

where

A-B and $R^1$ have the meanings indicated above, can be obtained by bringing compounds according to the general formula (IIb)

(IIb)

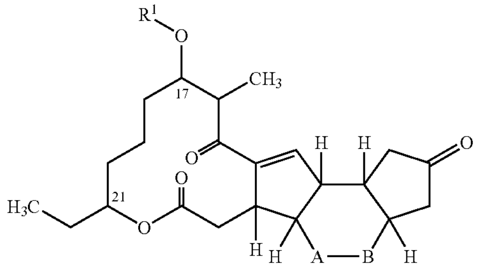

where

A-B and $R^1$ have the meanings indicated above, into contact with a microorganism in an aqueous culture medium under aerobic conditions.

The compounds according to the general formula (IIb) are known (see Creemer L. C. et al., 1998, J. Antibiotics 51 (8): 795-800; Sparks T. C. et al., 1998, J. Econ. Entomol. 91 (6): 1277-1283; Sparks T. C. et al., 2000, Pestic. Biochem. Physiol. 67 (3): 187-197; Paquette L. A. et al., 1998, J. Am. Chem. Soc. 120 (11): 2553-2563; Evans D. A. et al., 1993, J. Am. Chem. Soc. 115 (11): 4497-4513; Crouse G. D. et al., 2001, Pest. Manag. Sci. 57 (2): 177-185; Creemer L. C. et al., 2000, J. Antibiotics 53 (2): 171-178; Sparks T. C. et al., 2000, Proc.-Beltwide Cotton Conf. Vol. 2: 1225-1229) or can be produced according to the method described in WO 01/16303. In a similar manner, the initial compounds to be used in the method described above can be obtained on the basis of the corresponding natural spinosyns (see PCT/EP02/07572).

For example, one of the following strains can be used for this method, which are on deposit at the Deutsche Sammlung von Mikroorganismen und Zellkulturen GmbH (DSMZ) (German Collection of Microorgansims and Cell Cultures), Mascheroder Weg 1b, D-38124 Braunschweig, Germany, in accordance with the requirements of the Budapest Treaty:

| Name | Deposit Number |
|---|---|
| *Streptomyces djakartensis* | DSM 14327 |
| *Streptomyces griseofuscus* | DSM 14330 |
| *Streptomyces caelestis* | DSM 14328 |
| *Streptomyces antibioticus* | DSM 14329 |
| *Streptomyces griseus* | DSM 14331 |
| *Streptomyces aureofaciens* | DSM 14332 |

The aqueous culture medium typically contains an assimilable carbon source and an assimilable nitrogen source.

The compounds according to formula (IIa) are produced, for example, when one of the following strains are fermented in an aqueous culture medium under aerobic conditions in the presence of compounds according to formula (IIb): *Streptomyces djakartensis, S. griseofuscus, S. caelestis, S. antibioticus, S. griseus* or *S. aureofaciens*. The microorganisms are typically fermented in a culture medium, which contains a carbon source and possibly a protein-like material. Preferred carbon sources include glucose, brown sugar, saccharose, glycerine, starch, cornstarch, lactose, dextrin, molasses, etc. Preferred nitrogen sources include cottonseed flour, yeast, autolysed bakers yeast, solid milk components, soybean flour, maize flour, pancreatic or papain digested decomposition products from casein, solid distillation components, stocks from animal peptone, pieces of meat and pieces of bone, etc. Preferably combinations of these carbon sources and nitrogen sources are used. Trace elements, e.g. zinc, magnesium, manganese, cobalt, iron, etc., do not have to be added to the cultivation medium, as long as tap water and unpurified components are used as components in the medium.

The production of the compounds according to the general formula (IIa) can be induced at any temperature that guarantees sufficient growth of the microorganisms. The temperature is preferably between 21° C. and 32° C., particularly preferably approximately 28° C. In general, optimal production of the compounds according to formula (IIa) is obtained from 2 to 4 days after the compounds according to formula (IIb) are added to the culture. The production of the compounds according to the invention can take place both in shake flasks and in stirred fermentors.

Various methods can be used in order to isolate the compounds from the fermentation broth and to purify them, e.g. preparative gel chromatography, reversed phase preparative chromatography or preparative absorption chromatography. Detection can occur using UV-absorption or mass spectrometry, for example.

Compounds according to the general formula (II), in which $R^1$ stands for an amino sugar shown in formula 1d or 1e, and $R^3$ and A-B have the meanings indicated above, are novel and are a subject of the present invention.

Compounds according to the general formula (II), in which $R^1$ stands for an amino sugar shown in formula 1a, $R^3$ stands for hydrogen or hydroxy, and A-B stands for one of the following groups: $—HC{=}C(CH_3)—$, $—H_2C—CH_2—$ or $—H_2C—CH(CH_3)—$, are novel and are a subject of the present invention.

The additional initial substances of the amino compounds used for carrying out the method according to the invention are defined by the general formula (III).

In formula (III), X and $R^2$ have the meanings that were already mentioned, in conjunction with the description of the compounds according to the invention according to the general formula (I), as being preferred for this substituent.

The amino compounds according to formula (III) are partially commercially available, some of them are known, and can they be obtained according to known methods (e.g. see hetaryl-methoxamine: U.S. Pat. No. 5,489,680; DE-A 21 19 012, alkoxyamine: EP-A 495 750; DE-A 22 06 890; D. Favara et al., Farmaco, Ed. Sci. 42 (10), 1987, p. 697).

A general method for the manufacture of aminoxy compounds ($R^2—X—$, where X=O) according to formula (III), for example, consists in reacting a hydroxylamine derivative, which exhibits a protective group on the nitrogen (e.g. R' and R" together: phthaloyl group, isopropylidene group, α-hydroxy-benzylidene group), with a compound $R^2$-E (O-alkylation) in a diluent, and the protective group is subsequently separated. In the $R^2$-E compound, $R^2$ has the same meaning as indicated previously, and E stands for a nucleofuge leaving group, for example aliphatically or aromatically substituted sulphonyloxy, e.g. methanesulphonyloxy, salts of the sulphonic acid, p-toluene-sulphonyloxy (tosyloxy), and also halogen, for example, particularly bromine, chlorine or iodine (see O-alkylation). In FIG. 4 below, the production of amino compounds according to formula (III) is shown ($R^2—X$, where X=O):

FIG. 4

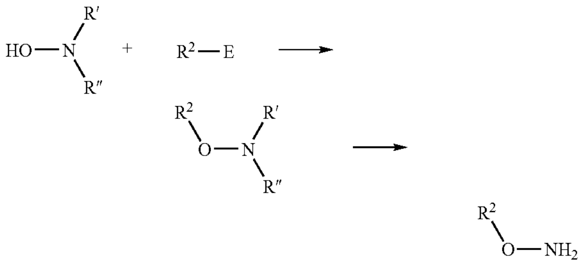

(III)

Alternatively, an intermolecular dehydration reaction can be performed by using a hydroxy compound, ($R^2—OH$, in FIG. 4, E=OH) for example. In particular, a variant of the Mitsunobu reaction comes under consideration (see Synthesis 1976, p. 682), in which the hydroxy compounds are reacted with N-protected hydroxylamine derivatives, such as N-hydroxyphthalimide, N-hydroxy-5-norbornene-2,3-dicarboxylic acid imide or acethydroxamic acid ethyl ester, as well as triphenylphosphine and N,N'-azodicarboxylic acid diethyl ester, for example.

The compounds according to formula (III) can be purposefully released in the following manner: the hydrazinolysis can preferably take place in a diluent, for example alcohol, at boiling temperature. Hydrolysis can preferably be carried out in an aqueous, aqueous-alcohol or alcohol solution by heating it for several hours. If R' and R" together designate an isopropylidene group, acidic hydrolysis can be used, and if R' and R" together designate an a-hydroxybenzylidene group or if R" designates a carbethoxy group, both alkaline and acidic hydrolysis can be used (see DE-A 21 19 012; D. Favara et al., Farmaco, Ed. Sci. 42 (10), (1987) p. 697).

For the production of the salts, inorganic acids, such as hydrochloric acid or sulphuric acid in ethanolic or isopropanolic solution are preferably used.

According to the invention, a possibly substituted aryl moiety or arylalkyl moiety can stand for the $R^2$ moiety, if necessary. If $R^2$ stands for an amino-substituted aryl moiety or arylalkyl moiety, the aromatic $NH_2$ group can be modified according to generally known methods. It can be advantageous for the acylation reactions, alkylation reactions or sulphonylation reactions to already take place in the protected intermediate R'R"N—O—$R^2$ in the presence of basic reaction additives and in the presence of a suitable diluent. The compounds according to the general formula (IIIa) can be released according to the methods described above (also see FIG. 5):

FIG. 5

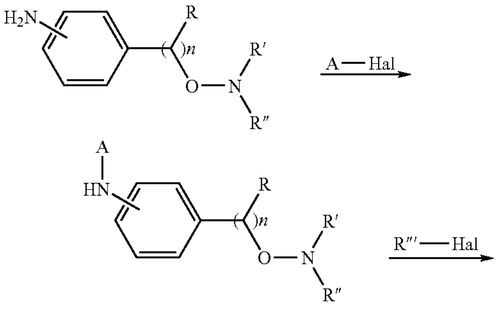

-continued

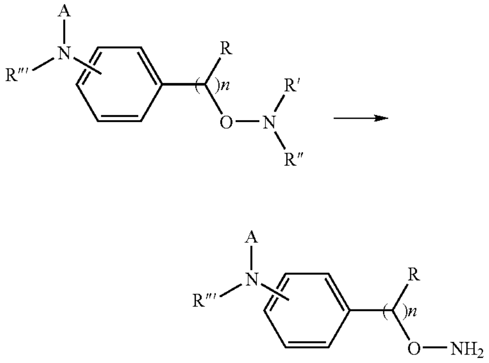

(IIIa)

A = $SO_2$—$R^1$ (z.B. $R^1$ = Halalkyl, Alkyl, Aryl, Arylalkyl)
CO—$R^1$, CO—O—$R^1$
R = H, Methyl
R''' = Halalkyl, Alkyl, Arylalkyl, Acyl
n = 1, 2

A general method for the manufacture of aminoxy compounds ($R^2$—X—, where X=NH, $NR^4$) according to formula (Ill) consists in, for example, reacting a suitable primary or secondary amino compound with an N-tert-butyloxycarbonyl (Boc) transfer reagent, e.g. the commercially available N-Boc-3-(4-cyanophenyl)oxaziridine (BCPO), according to known methods (J. Vidal et al., J. Chem. Soc., Chem. Commun. 1991, 435-437; J. Org. Chem. 1993, 58, 4791-4793). Alternatively, the commercially available N-(Boc-amino)phthalimide or N-(benzyloxycarbonyl-amino)phthalimide can be used as suitable initial components (N. Brosse et al., J. Org. Chem. 2001, 66, 2869). The $R^2$ moiety can be introduced via a Mitsunobu reaction or N-alkylation. After separating the protective groups (Boc, benzyloxycarbonyl), the hydrazines can be utilised for the reaction according to the invention (also see FIG. 6).

FIG. 6

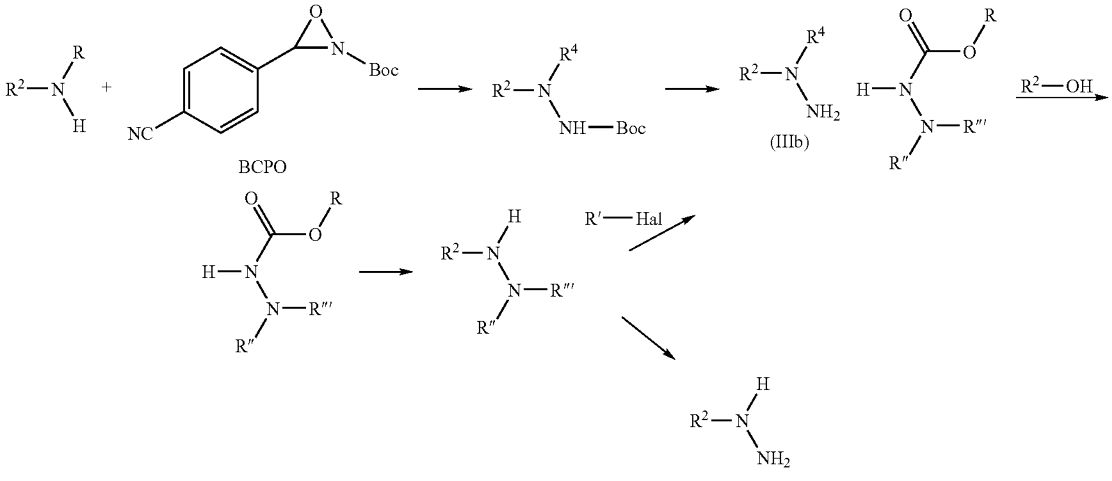

BCPO
(IIIb)

(IIIc)

The reaction of the 9-keto spinosyn derivatives according to the general formula (II), with the amino compounds according to the general formula (III), are preferably carried out in the presence of a basic reaction additive while using diluents.

All suitable acid binders can be used as basic reaction additives for performing the method according to the invention, such as amines, particularly tertiary amines, alkaline and alkaline earth compounds.

As examples, the following are given: hydroxides, oxides and carbonates of lithium, sodium, potassium, magnesium, calcium and barium, additional basic compounds such as amidine bases or guanidine bases like 7-methyl-1,5,7-triazabicyclo(4.4.0)dec-5-ene (MTBD); diazabicyclo(4.3.0)nonene (DBN), diazabicyclo(2.2.2)-octane (DABCO), 1,8-diazabicyclo(5.4.0)undecene (DBU), cyclohexyltetrabutylguanidine (CyTBG), cyclohexyltetramethylguanidine (CyTMG), N,N,N,N-tetramethyl-1,8-naphthalinediamine, pentamethylpiperidine, tertiary amines such as triethylamine, trimethylamine, tribenzylamine, triisopropylamine, tributylamine, tribenzylamine, tricyclohexylamine, triamylamine, trihexylamine, N,N-dimethyl-aniline, N,N-dimethyl-toluidine, N,N-dimethyl-p-aminopyridine, N-methyl-pyrrolidine, N-methyl-piperidine, N-methyl-imidazole, N-methyl-pyrrole, N-methyl-morpholine, N-methyl-hexamethylenimine, pyridine, 4-pyrrolidinopyridine, 4-dimethylamino-pyridine, quinoline, α-picoline, β-picoline, isoquinoline, pyrimidine, acridine, N,N,N',N'-tetramethylenediamine, N,N',N'-tetraethylenediamine, quinoxaline, N-propyl-diisopropylamine, N-ethyl-diisopropylamine, N,N'-dimethylcyclo-hexylamine, 2,6-lutidine, 2,4-lutidine or triethylenediamine.

Aromatic amines, particularly pyridine, or tertiary amines, particularly trialkylamines such as triethylamine, N,N-diisopropyl-ethylamine, N-propyl-diisopropylamine, N,N'-dimethylcyclohexylamine or N-methylmorpholine, are used preferably.

In general it is beneficial to perform the method according to the invention in the presence of diluents. It is best if diluents are used in such a quantity that the reaction mixture can be easily stirred during the entire process. All inert organic solvents can be used as diluents for carrying out the method according to the invention.

The following are given as examples: halogenated hydrocarbons, particularly chlorohydrocarbons such as tetrachloroethylene, tetrachloroethane, dichloropropane, methylenechloride, dichlorobutane, chloroform, tetrachlorocarbon, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol; ethers such as ethylpropylether, methyl-tert-butylether, n-butylether, anisole, phenetol, cyclohexylmethylether, dimethylether, diethylether, dipropylether, diisopropylether, di-n-butylether, diisobutylether, diisoamylether, ethyleneglycole-dimethylether, tetrahydrofuran, dioxane, dichlorodiethylether and polyethers of ethyleneoxide and/or propyleneoxide: amines such as trimethyl-, triethyl-, tripropyl-, tributylamine, N-methyl-morpholine, pyridine and tetramethylenediamine, nitrohydrocarbons such as nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile, as well as compounds such as tetrahydrothiophenedioxide and dimethylsulphoxide, tetramethylenesulphoxide, dipropylsulphoxide, benzylmethylsulphoxide, diisobutylsulphoxide, dibutylsulphoxide, diisoamylsulphoxide; sulphones such as dimethyl-, diethyl-, dipropyl-, dibutyl-, diphenyl-, dihexyl-, methylethyl-, ethylpropyl-, ethylisobutyl- and pentamethylenesulphone; aliphatic, cycloaliphatic or aromatic hydrocarbons such as pentane, hexane, heptane, octane, nonane and technical hydrocarbons, for example so-called white spirits with components that have boiling points in the range of 40° C. to 250° C., for example, cymene, petroleum fractions within a boiling point range of 70° C. to 190° C., cyclohexane, methylcyclohexane, petroleum ether, Ligroin, octane, benzene, toluene, chlorobenzene, bromobenzene, nitrobenzene, xylene; esters such as methyl-, ethyl-, butyl-, isobutylacetate, as well as dimethyl-, dibutyl-, ethylenecarbonate; amides such as hexamethylene-phosphortriamide, formamide, N-methyl-formamide, N,N-dimethyl-formamide, N,N-dipropylformamide, N,N-dibutylformamide, N-methyl-pyrrolidine, N-methyl-caprolactam, 1,3-dimethyl-3,4,5,6-tetrahydro-2(1H)-pyrimidine, octylpyrrolidone, octylcaprolactam, 1,3-dimethyl-2-imidazolindione, N-formylpiperidine, N,N'-1,4-diformylpiperazine; ketones such as acetone, acetophenone, methylethylketone, methylbutylketone.

Of course mixtures of the indicated solvents and diluents can be used in the method according to the invention.

Preferred diluents for performing the method according to the invention, however, are amines such as trimethyl-, triethyl-, tripropyl-, tributylamine, N-methyl-morpholine and pyridin, amides such as N,N-dimethylformamide, N,N-dipropylformamide, N,N-dibutylformamide or N-methylpyrrolidine.

Reactions of the amino compounds according to the general formula (III) can be carried out by reacting 17-β-desosaminyl-9-keto spinosyn and the 9-keto spinosyn-aglycone derivatives according to the general formula (II) in the presence of an amino compound according to the general formula (III) and in the presence of one of the basic reaction additives indicated, and possibly in one of the diluents indicated The reaction time preferably amounts to between 10 minutes and 48 hours. The reaction preferably occurs at temperatures between −10° C. and +200° C., more preferably between +10° C. and +180° C., most preferably at room temperature. It is basically possible to perform the work at normal pressure. The work is preferably done at normal pressure or at pressures up to 15 bar, and possible in a protective gas atmosphere (nitrogen or helium).

In order to carry out the process according to the invention, generally 0.5 to 7.0 mol, preferably 1.0 to 5.0 mol, particularly preferably 1.5 to 2.5 mol of amino compound according to the general formula (III) is employed for the oxime formation in the general formula (II).

After completing the reaction, the entire reaction compound is concentrated in a vacuum and purified in the customary manner using column chromatography (also see the Examples of Manufacture).

The active substances exhibit good plant tolerability, favourable endothermic toxicity, good environmental tolerability, and are suitable for protecting plants and plant organs, increasing harvest yields, improving the quality of the harvest product and controlling animal pests, in particular insects, arachnids and nematodes, which occur in the agricultural industry, forests, gardens and recreational equipment, as well as in the areas of inventory and product protection and the hygiene sector. They are preferably used as plant protective agents. They are effective against regularly sensitive and resistant types, as well as against all or certain stages of development. The following pests are included in those mentioned above:

From the order of Isopoda, for example, *Oniscus asellus, Armadillidium vulgare, Porcellio scaber.*

From the order of Diplopoda, for example, *Blaniulus guttulatus.*

From the order of Chilopoda, for example, *Geophilus carpophagus, Scutigera* spp.

From the order of Symphyla, for example, *Scutigerella immaculata.*

From the order of Thysanura, for example, *Lepisma saccharina.*

From the order of Collembola, for example, *Onychiurus armatus.*

From the order of Orthoptera, for example, *Acheta domesticus, Gryllotalpa* spp., *Locusta migratoria migratorioides, Melanoplus* spp., *Schistocerca gregaria.*

From the order of Blattaria, for example, *Blatta orientalis, Periplaneta americana, Leucophaea maderae, Blattella germanica.*

From the order of Dermaptera, for example, *Forficula auricularia.*

From the order of Isoptera, for example, *Reticulitermes* spp.

From the order of Phthiraptera, for example, *Pediculus humanus corporis, Haematopinus* spp., *Linognathus* spp., *Trichodectes* spp., *Damalinia* spp.

From the order of Thysanoptera, for example, *Hercinothrips femoralis, Thrips tabaci, Thrips palmi, Frankliniella accidentalis.*

From the order of Heteroptera, for example, *Eurygaster* spp., *Dysdercus intermedius, Piesma quadrata, Cimex lectularius, Rhodnius prolixus, Triatoma* spp.

From the order of Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of Hymenoptera, for example, *Diprion* spp., *Hoplocampa* spp., *Lasius* spp., *Monomorium pharaonis, Vespa* spp.

From the order of Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of Siphonaptera, for example, *Xenopsylla cheopis, Ceratophyllus* spp.

From the class of Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The following belong to the group of plant-parasitic nematodes, for example: *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The substances according to the invention exhibit strong microbicidal efficacy and can be used for controlling undesired microorganisms, such as fungi and bacteria, in the areas of plant and material protection.

Fungicides can be used in the area of plant protection for controlling plasmodiophoromycetes, oomycetes, chytridiomycetes, zygomycetes, ascomycetes, basidiomycetes and deuteromycetes.

Bactericides can be used in the area of plant protection for controlling *Pseudomonadaceae, Rhizobiaceae, Enterobacteriaceae, Corynebacteriaceae* and *Streptomycetaceae.*

The following is a non all-inclusive list of some pathogens from fungal and bacterial infections, which fall under the abovementioned general headings:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea*

(Conidial form: *Drechslera*, syn: *Helminthosporium*);

*Cochliobolus* species, such as, for example, *Cochliobolus sativus*

(Conidial form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae*; and

*Pseudocercosporella* species, such as, for example, *Pseudocercosporella herpotrichoides.*

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances, which are capable of stimulating the defence system of plants such that, when the treated plants are subsequently innoculated with undesirable microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of aboveground parts of plants, of propagation stock and seeds, and of the soil.

The active compounds according to the invention can be used to treat all plants and parts of plants. By plants are understood here all plants and plant populations such as desired and undesired wild plants or crop plants (including naturally occurring crop plants). Crop plants can be plants which can be obtained by conventional breeding and optimisation methods or by biotechnological and genetic engineering methods or combinations of these methods, including the transgenic plants and including the plant varieties which can or cannot be protected by varietal property rights. Parts of plants are to be understood as meaning all aboveground and below-ground parts and organs of plants, such as the shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds. Parts of plants also include harvested plants and vegetative and generative propagation material, for example seedlings, tubers, rhizomes, cuttings and seeds.

Particularly preferably, plants of the plant cultivated plants, which are in each case commercially available or in use, are treated according to the invention. Plant cultivated plants are to be understood as meaning plants having new properties ("traits") and which have been obtained by conventional breeding, by mutagenesis or by recombinant DNA techniques. They can be cultivated plants, varieties, bio- or genotypes.

Depending on the plant species or plant cultivated plants, their location and growth conditions (soils, climate, vegetation period, nutrition), the treatment according to the invention may also result in super-additive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible, which exceed the effects which were actually to be expected.

The transgenic plants or plant cultivated plants (i.e. those obtained by genetic engineering), which are preferably treated according to the invention, include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasised are in particular increased defence of the plants against insects by toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c Cry2Ab, Cry3Bb and CryIF and also combinations thereof) (hereinafter referred to as "Bt plants"). Traits that are also particularly emphasised are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosates or phosphinotricin (for example the "PAT" gene). The genes, which impart the desired traits in question, can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties, which are sold under the trade names Roundup Ready® (tolerance to glyphosates, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance), which may be mentioned, include the varieties sold under the name Clearfield® (for example maize). Of course, these statements also apply to plant cultivated plants having these genetic traits or genetic traits still to be developed, which will be developed and/or marketed in the future.

The plants listed can be treated according to the invention in a particularly advantageous manner with the compounds according to the general formula (I) or the active substance mixtures according to the invention. The preferred ranges stated above for the active compounds and mixtures also apply to the treatment of these plants. Particular emphasis is given to the treatment of plants with the compounds or mixture specifically mentioned in the present text.

The treatment of the plants and the parts of plants with the active compounds according to the invention is carried out directly or by action on their surroundings, habitat or storage space, according to customary treatment methods, for example by dipping, spraying, evaporating, atomising, strewing, spreading and, in the case of propagation material, in particular in the case of seeds, further with single or multi-layer coating.

In the protection of materials, the compounds according to the invention can be employed for protecting industrial materials against infection with, and destruction by, undesired microorganisms.

Industrial materials in the present context are understood as meaning non-living materials that have been prepared for use in industry. For example, industrial materials, which are intended to be protected by active compounds according to the invention from microbial change or destruction, can be adhesives, glues, paper and cardboard, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials, which may be mentioned within the scope of the present invention, are preferably adhesives, glues, paper and cardboard, leather, wood, paints, cooling lubricants and heat-transfer liquids, particularly preferably wood.

Microorganisms capable of degrading or changing the industrial materials are, for example, bacteria, fungi, yeasts, algae and slime organisms. The active compounds according to the invention preferably act against fungi, in particular moulds, wood-discolouring and wood-destroying fungi (*Basidiomycetes*), and against slime organisms and algae.

Microorganisms of the following genera may be mentioned as examples:

*Alternaria*, such as *Alternaria tenuis;*
*Aspergillus*, such as *Aspergillus niger;*
*Chaetomium*, such as *Chaetomium globosum;*
*Coniophora*, such as *Coniophora puetana;*
*Lentinus*, such as *Lentinus tigrinus;*
*Penicillium*, such as *Penicillium glaucum;*
*Polyporus*, such as *Polyporus versicolor;*
*Aureobasidium*, such as *Aureobasidium pullulans;*
*Sclerophoma*, such as *Sclerophoma pityophila;*
*Trichoderma*, such as *Trichoderma viride;*
*Escherichia*, such as *Escherichia coli;*
*Pseudomonas*, such as *Pseudomonas aeruginosa;*
*Staphylococcus*, such as *Staphylococcus aureus.*

Depending on their particular physical and/or chemical properties, the active compounds can be converted to the customary formulations, such as solutions, emulsions, suspensions, powders, foams, pastes, granules, aerosols and micro-encapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foaming agents. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, as well as water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example, ground natural minerals such as kaolins, clays, talc, chalk, quartz, attapulgite, montmorillonite or diatomaceous earth, and ground synthetic minerals such as highly disperse silicic acid, aluminium oxide and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foaming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example, lignosulphite waste liquors and methylcellulose.

Bonding agents such as carboxymethylcellulose and natural and synthetic polymers in the form of powders, granules or latex-forming polymers, such as Gum Arabic, polyvinyl alcohol and polyvinyl acetate, as well as natural phospholipids such as cephalins and lecithins and synthetic phospholipids can be used in the formulations. Other possible additives are mineral and vegetable oils.

It is possible to use colourants such as inorganic pigments, for example iron oxide, titanium oxide and cyan blue, and organic dyes such as alizarin dyes, azo dyes and metal phthalocyanine dyes, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacryl-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvon; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos;. epoxiconazole; ethaboxam; ethirimol; etridiazole; famoxadon; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide; flutolanil; flutriafol; folpet; fosetyl-aluminium; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris albesilate; iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulphocarb; methfuroxam; metiram; metominostrobin; metsulphovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxin; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulphur; tebuconazole; tecloftalam; tecnazene; tetcyclasis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-2-[(methylsulphonyl)amino]-butanamide; 1-(1-naphthalenyl)-1H-pyrrol-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazole-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decan-3-amine; sodium tetrathiocarbonate;

as well as copper salts and preparations, such as Bordeaux mixture; copper hydroxide; copper naphthenate; copper oxychloride; copper sulphate; cufraneb; copper oxide; mancopper; and oxine-copper.

Bactericides:

Bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

Abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R isomers, alphacypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, *Baculo viruses, Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl isomer, bioethanomethrin, biopermethrin, bioresmethrin, bistrifluron, BPMC, brofenprox, bromophos-ethyl, bromopropylate, bromfenvinfos(-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulphan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos(-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R trans-isomer), cyromazine, DDT, deltamethrin, demeton-S-methyl, demeton-S-methylsulphon, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulphoton, docusat-sodium, dofenapyn, DOWCO439, eflusilanate, emamectin, emamectin-benzoate, empenthrin (1R isomer), endosulphan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulphothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granuloseviruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedral viruses, kinoprene, lambda-cyhalothrin, lindane, lufenuron, malathion, mecarbam, mesulphenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, ometboate, oxamyl, oxydemetonmethyl,

*Paecilomyces fumosoroseus*, parathion-methyl, parathion (-ethyl), permethrin(cis-, trans-), petroleum, PH-6045, phenothrin (1R trans-isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulphluramid, sulphotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*,

WL-108477, WL-40027,

YI-5201, YI-5301, YI-5302,

XMC, xylylcarb,

ZA-3274, zeta-cypermethrin, zolaprofos, ZXI-8901, the compound 3-methyl-phenyl-propylcarbamate (Tsumacide Z), the compound 3-(5-Chlor-3-pyridinyl)-8-(2,2,2-trifluoroethyl)-8-azabicyclo[3.2.1]octane-3-carbonitrile (CAS-7Reg.-No. 185982-80-3) and the corresponding 3-endo-isomers (CAS-Reg.-No. 185984-60-5) (see WO-96/37494, WO-98/25923), as well as other preparations, which contain plant extracts effective as insecticides, nematodes, fungi or viruses.

A mixture with other known active compounds, such as herbicides, or with fertilizers and growth regulators, safeners or semiochemicals is also possible.

In addition, the compounds of the formula (I) according to the invention also have very good antimycotic activity. They have a very broad antimycotic activity spectrum in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and audouinii. The list of these fungi by no means covers the entire extent of the mycotic spectrum covered, but is only for illustration.

When the active substances according to the invention are used as fungicides, the application rate can be varied within a large range depending on the type of application. When treating plant parts, the application rates of the active substance are generally between 0.1 and 10,000 g/ha, preferably between 10 and 1,000 g/ha. When treating seeds, the application rates of the active substance are generally between 0.001 and 50 g per kilogram of seeds, preferably between 0.01 and 10 g per kilogram of seeds. When treating soil, the application rates of the active substance are generally between 0.1 and 10,000 g/ha, preferably between 1 and 5,000 g/ha.

When used as insecticides, the active substances according to the invention can furthermore be present in their commercial formulations and in the forms of use prepared from these formulations, in mixtures with synergists. Synergists are compounds which increase the activity of the active compounds, without it being necessary for the added synergist to be active itself.

When used as insecticides, the active substances according to the invention can furthermore be present in their commercial formulations and in the forms of use prepared from these formulations, in mixtures with inhibitors, which reduce decomposition of the active substance after application in the vicinity of the plant, on the surface of plant parts or in plant tissue.

The application is carried out in a manner that is adapted to the form of use.

When used against hygiene pests and stored product pests, the active substance is distinguished by excellent residual activity on wood and clay, and by good alkaline stability on limed substrates.

The active substances according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of Anoplurida, for example, *Haematopinus* spp., *Linognathus* spp., *Pediculus* spp., *Phtirus* spp., *Solenopotes* spp.

From the order of Mallophagida and the suborders of Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of Diptera and the suborders of Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of Siphonapterida, for example, *Pulex* spp., *Ctenocephalides* spp., *Xenopsylla* spp., *Ceratophyllus* spp.

From the order of Heteropterida, for example, *Cimex* spp., *Triatoma* spp., *Rhodnius* spp., *Panstrongylus* spp.

From the order of Blattarida, for example, *Blatta orientalis*, *Periplaneta americana*, *Blattela germanica*, *Supella* spp.

From the subclass of Acaria (Acarida) and the orders of Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The Active substances according to the invention according to formula (I) are also suitable for controlling arthropods which attack agricultural livestock such as, for example, cattle, sheep, goats, horses, pigs, donkeys, camels, buffalo, rabbits, chickens, turkeys, ducks, geese, honey bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible with the use of the active compounds according to the invention The active substances according to the invention are used in the veterinary sector in a known manner via enteral administration in the form of, for example, tablets, capsules, potions, drenches, granules, pastes, boli, the feed-through method, suppositories, via parenteral administration such as, for example, by injections (intramuscularly, subcutaneously, intravenously, intraperitoneally and the like), by implants, by nasal administration, by dermal administration in the form of, for example, immersing or dipping, spraying, pouring-on, spotting-on, washing, dusting, and with the aid of moulded articles containing active substances such as collars, ear tags, tail tags, limb bands, halters, marking devices and the like.

When used for cattle, poultry, domestic animals and the like, the active substances according to formula (I) can be applied as formulations (for example powders, emulsions, flowing agents), which contain the active substances in an amount of 1 to 80% by weight, either directly or after 100- to 10,000-fold dilution, or they may be used as a chemical bath.

Moreover, it has been found that the active substances according to the invention exhibit potent insecticidal action against insects that destroy industrial materials.

The following insects may be mentioned as an example and with preference, but not as a limitation:

Beetles, such as, for example, *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*;

Dermapterans such as, for example, *Sirex juvencus*, *Urocerus gigas*, *Urocerus gigas taignus*, *Urocerus augur*;

Termites, such as, for example, *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptoternes formosanus*;

Bristletails, such as, for example, *Lepisma saccharina*;

Industrial materials in the present context are understood as meaning non-living materials such as, preferably, plastics, adhesives, glues, paper and cardboard, leather, wood, timber products and paints.

The materials, which are to be protected from insect attack, are especially preferably wood and timber products.

Wood and timber products, which can be protected by the substance according to the invention, or mixtures containing the substance, are to be understood as meaning, for example:

Construction timber, wooden beams, railway sleepers, bridge components, jetties, wooden vehicles, boxes, pallets, containers, telephone poles, wood lagging, wooden windows and doors, plywood, clipboard, joinery, or timber products which quite generally are used in house construction or building joinery.

The insecticidal compounds or concentrates used for protecting wood and timber products contain the active substance according to the invention in a concentration of 0.0001 to 95% by weight, in particular 0.001 to 60% by weight.

The amount of compound or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight of the active substance, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wettening agent.

Organochemical solvents, which are preferably, employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils, which are preferably used, are those with a boiling range of 170 to 220° C., white spirit with a boiling range of 170 to 220° C., spindle oil with a boiling range of 250 to 350° C., petroleum and aromatics with a boiling range of 160 to 280° C., turpentine oil, and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably $\alpha$.-monochloronaphthalene are used.

The organic oily or oil-type solvents of low volatility and with an evaporation number of above 35 and a flash point of above 30° C., preferably above 45° C., can be replaced in part by organochemical solvents of high or medium volatility, provided that the solvent mixture also has an evaporation number of above 35 and a flash point of above 30° C., preferably above 45° C., and that the insecticide/fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents that contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellents, odour-masking agents, and inhibitors or anticorrosive agents and the like, all of which are known in their own right, can be employed.

In accordance with the invention, the compound or the concentrate preferably comprises, as organochemical binders, at least one alkyl resin or modified alkyl resin and/or a drying vegetable oil. Alkyd resins, which are preferably used in accordance with the invention, are those with an oil content of over 45% by weight, preferably 50 to 68% by weight.

Some or all of the abovementioned binders can be replaced by a fixative (mixture) or plasticiser (mixture). These additives are intended to prevent volatilisation of the active substances, as well as crystallisation or precipitation. They preferably replace 0.01 to 30% of the binder (based on 100% of binder employed).

The plasticisers are from the chemical classes of phthalic acid esters, such as dibutyl phthalate, dioctyl phthalate or benzyl butyl phthalate, phosphoric acid esters such as tributyl phosphate, adipic acid esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, also water, if appropriate as a mixture with one or more of the abovementioned organochemical solvents or diluents, emulsifiers and dispersants.

Particularly effective timber protection is achieved by industrial-scale impregnation processes, for example vacuum, double-vacuum or pressure processes.

The ready-to-use compositions can also comprise other insecticides, if appropriate, and also one or more fungicides, if appropriate.

Preferable additives are the insecticides and fungicides mentioned in WO 94/29268. The compounds mentioned in this document are an explicit component of the present patent application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide, triflumuron, clothianidine, spinosad and tefluthirn, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can also be employed for protecting objects from fouling which come into contact with saltwater or brackish water, such as ships' hulls, screens, nets, buildings, moorings and signalling systems.

Fouling by sessile Oligochaeta, such as *Serpulidae*, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally owing to frequent residence in the dry dock.

Apart from fouling by algae, for example *Ectocarpus* sp. and *Ceramium* sp., fouling by sessile Entomostraka groups, which come under the generic term *Cirripedia* (cirriped crustaceans), is of particular importance.

Surprisingly, it has now been found that the active compounds according to the invention have an outstanding antifouling action, either alone or in combination with other active substances.

By using the compounds according to the invention by themselves or in combination with other active substances, one can avoid the use of, or significantly reduce the concentration of compounds containing, heavy metals, such as, for example, in bis(trialkyltin)sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylene-bisdithiocarbamate, copper thiocyanate, copper naphthenate and tributyltin halides.

If appropriate, the ready-to-use antifouling paints can additionally comprise other active substances, preferably algicides, fungicides, herbicides, molluscicides, or other antifouling active substances.

Preferably, substances to be used in combination with the antifouling compounds according to the invention are:

Algicides, such as 2-tert.-butylamino-4-cyclopropylamino-6-methylthio-1,3,5-triazine, dichlorophen, diuron, endothal, fentine acetate, isoproturon, methabenzthiazuron, oxyfluorfen, quinoclamine and terbutryn;

Fungicides, such as benzo[b]thiophenecarboxylic acid cyclohexylamide S,S-dioxide, dichlofluanid, fluor-folpet, 3-iodo-2-propinyl butylcarbamate, tolylfluanid and azoles such as azaconazole, cyproconazole, epoxyconazole, hexaconazole, metconazole, propiconazole and tebuconazole;

Molluscicides, such as fentin acetate, metaldehyde, methiocarb, niclosamide, thiodicarb and trimethacarb;

*Ferrous chelates,* or conventional antifouling active substances, such as 4,5-dichloro-2-octyl-4-isothiazolin-3-one, diiodomethylparatryl sulphone, 2-(N,N-di-methylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleinimide.

The antifouling compounds used comprise the active compound combinations according to the invention in a concentration of 0.001 to 50% by weight, in particular 0.01 to 20% by weight.

Moreover, the antifouling compounds according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active substances and insecticidal active substances according to the invention, antifouling paints contain, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also contain inorganic pigments, organic pigments or colourants, which are preferably insoluble in salt water. Paints may furthermore contain materials such as colophonium to allow controlled release of the active substances. Furthermore, the paints may comprise plasticisers, which are modifiers that affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed alone or in combination with other active substances and additives in domestic insecticide products for controlling these pests. They are active against sensitive and resistant species and against all developmental stages. These pests include:

From the order of Scorpionidea, for example, *Buthus occitanus.*

From the order of Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of Araneae, for example, *Aviculariidae, Araneidae.*

From the order of Opiliones, for example, *Pseudoscorpiones chelifer, Pseudoscorpiones cheiridium, Opiliones phalangium.*

From the order of Isopoda, for example, *Oniscus asellus, Porcellio scaber.*

From the order of Diplopoda, for example, *Blaniulus guttulatus, Polydesmus* spp.

From the order of Chilopoda, for example, *Geophilus* spp.

From the order of Zygentoma, for example, *Ctenolepisma* spp., *Lepisma saccharina, Lepismodes inquilinus.*

From the order of Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of Saltatoria, for example, *Acheta domesticus*.

From the order of Dermaptera, for example, *Forficula auricularia*.

From the order of Isoptera, for example, *Kalotermes* spp., *Reticulitermes* spp.

From the order of Psocoptera, for example, *Lepinatus* spp., *Liposcelis* spp.

From the order of Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of Lepidoptera, for example, *Achroia grisella, Galleria mellonella, Plodia interpunctella, Tinea cloacella, Tinea pellionella, Tineola bisselliella*.

From the order of Siphonaptera e.g. *Ctenocephalides canis, Ctenocephalides felis, Pulex irritans, Tunga penetrans, Xenopsylla cheopis*.

From the order of Hymenoptera, for example, *Camponotus herculeanus, Lasius fuliginosus, Lasius niger, Lasius umbratus, Monomorium pharaonis, Paravespula* spp., *Tetramorium caespitum*.

From the order of Anoplura, for example, *Pediculus humanus capitis, Pediculus humanus corporis, Phthirus pubis*.

From the order of Heteroptera, for example, *Cimex hemipterus, Cimex lectularius, Rhodinus prolixus, Triatoma infestans*.

Use in the area of domestic insecticides occurs alone or in combination with other suitable active substances, such as phosphoric acid esters, carbamates, pyrethroids, neonicotinoids, growth regulators or active substances from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth paper, moth bags and moth gels, as granules or dusts, in baits for spreading or in bait stations.

EXAMPLES OF USE

Example A

Meloidogyne Test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amount of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. Galls form on the roots.

After the desired length of time, the nematicidal activity is determined by the gall formation in %. 100% means that no galls have been found; 0% means that the number of galls on the treated plants corresponds to that of the untreated control. In this test, for example, the compounds I-66, I-72, I-76, I-99, I-135, I-144, I-150 and I-155 of the Preparation Examples exhibit good efficacy.

Example B

Myzus Test (Spray Treatment)

| | |
|---|---|
| Solvent: | 78 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with water containing emulsifier to the desired concentration.

Chinese cabbage leaves (*Brassica pekinensis*), which are afflicted with all stages of the green peach aphid (*Myzus persicae*), are sprayed with a preparation of the active compound at the desired concentration.

After the desired amount of time, the effect is rated in %. A figure of 100% denotes that all aphids were destroyed, and 0% denotes that no aphids were destroyed.

In this test, for example, the compounds I-91, I-126 and I-140 of the Preparation Examples exhibit good efficacy.

Example C

Phaedon Test (Spray Treatment)

| | |
|---|---|
| Solvent: | 78 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with water containing emulsifier to the desired concentration.

Chinese cabbage leaves (*Brassica pekinensis*) are sprayed with a preparation of the active compound, and after the spray has dried, they are infested with mustard beetle larvae (*Phaedon cochleariae*).

After the desired amount of time, the effect is rated in %. A figure of 100% denotes that all of the beetle larvae were destroyed, and 0% denotes that no beetle larvae were destroyed.

In this test, for example, the compound I-105 of the Preparation Examples exhibits good efficacy.

Example D

*Spodoptera frugiperda* Test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amount of solvent and emulsifier, and the concentrate is diluted with water containing emulsifier to the desired concentration.

Cabbage leaves (*Brassica oleracea*) are treated by dipping them in the preparation of active compound at the desired concentration, and they are infested with caterpillars of the fall armyworm (*Spodoptera frugiperda*) while the leaves are still damp.

After the desired amount of time, destruction is rated in %. A figure of 100% denotes that all of the caterpillars were destroyed; 0% denotes that no caterpillars were destroyed.

In this test, for example, the compound I-70 of the Preparation Examples exhibits good efficacy.

Example E

*Spodoptera frugiperda* Test/Artificial Feed

| | |
|---|---|
| Solvent: | 31 parts by weight of acetone |
| Emulsifier: | 1 part by weight of alkylaryl polyglycol ether |

To produce a suitable preparation of active compound, 1 part by weight of active compound is mixed with the stated amount of solvent and emulsifier, and the concentrate is diluted with water containing emulsifier to the desired concentration.

A specified amount of the active compound preparation at the desired concentration is added to a standardised quantity of artificial feed using a pipette. A larva (L3) of the fall armyworm (*Spodoptera frugiperda*) is then added to the feed, six separate times.

After the desired amount of time, destruction is rated in %. A figure of 100% denotes that all of the animals were destroyed; 0% denotes that no animals were destroyed.

In this test, for example, the compound I-22 of the Preparation Examples exhibits good efficacy.

Example F

Tetranychus Test (OP-Resistant/Spray Treatment)

| | |
|---|---|
| Solvent: | 78 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with water containing emulsifier to the desired concentration.

Common bean leaves (*Phaseolus vulgaris*), which are afflicted with all stages of the two-spotted spider mite (*Tetranychus urticae*), are sprayed with a preparation of the active compound at the desired concentration.

After the desired amount of time, the effect is rated in %. A figure of 100% denotes that all of the spider mites were destroyed; 0% denotes that no spider mites were destroyed.

In this test, for example, the compounds I-90 and I-95 of the Preparation Examples exhibit good efficacy.

Example G

Tetranychus Test (OP-Resistant/Immersion Treatment)

| | |
|---|---|
| Solvent: | 7 parts by weight of dimethylformamide |
| Emulsifier: | 2 parts by weight alkylaryl polyglycol ether |

To produce a suitable preparation of active compound, 1 part by weight of active compound is mixed with the stated amount of solvent and emulsifier, and the concentrate is diluted with water containing emulsifier to the desired concentration.

Common bean plants (*Phaseolus vulgaris*), which are severely afflicted with all stages of the two-spotted spider mite (*Tetranychus urticae*), are immersed in a preparation of the active compound at the desired concentration.

After the desired amount of time, the effect is rated in %. A figure of 100% denotes that all of the spider mites were destroyed; 0% denotes that no spider mites were destroyed.

In this test, for example, the compound I-22 of the Preparation Examples exhibit good efficacy.

Preparation Examples

Example (I-1)

(E/Z)-9-(3,4-dichlorobenzyloxyimino)-spinosyn A-aglycone

The 9-keto spinosyn A-aglycone [compound according to the general formula (II), where $R^1$ stands for hydrogen and A-B stands for the group —HC═CH—] can be produced according to WO 02/079184.

50.0 mg (0.125 mmol) of 9-keto spinosyn A-aglycone is stirred in 2 ml abs. pyridine and mixed with 143.1 g (0.625 mmol) O-(3,4-dichlorobenzyl)-hydroxylamine. After stirring for 24 hours at 25° C., the entire reaction preparation is concentrated in vacuum. Column chromatography on silica gel is then performed (silica gel 60-Merck, grain size: 0.04 to 0.063 mm) using cyclohexane/acetic acid ethyl ester (4:1) as mobile phases, and the (E/Z)-isomer mixture is separated. The reaction yields 46.8 mg (65.2% of the theoretical yield) of (Z)-9-(3,4-dichlorobenzyloxyimino)-spinosyn A-aglycone and 27.1 mg (37.7% of the theoretical yield) of (E)-9-(3,4-dichlorobenzyloxyimino)-spinosyn A-aglycone.

(Z)-9-(3,4-dichlorobenzyloxyimino)-spinosyn A-aglycone $C_{31}H_{37}Cl_2NO_5$ (574.5) LC-MS: m/z (%)=574 ($M^+$, 100); $R_t$=8.50 min.

(E)-9-(3,4-dichlorobenzyloxyimino)-spinosyn A-aglycone $^{13}C$-NMR: DMF-$d_7$, δ=9.5, 16.2 ($CH_3$); 22.5, 28.9, 30.5, 34.3; 35.6 (5×$CH_2$); 33.1 (c-8); 35.1 (C-10); 41.8; 41.9, 46.3, 48.7, 48.8, 49.5, (CH); 72.1 (CH—OH); 74.0 (O—$CH_2$); 76.7 (CH—O—); 129.8, 129.6 (—HC═CH—); 128.6, 130.3, 131.2, 141.1 (4×Ar—C); 131.1, 132.0 (2×Ar—C—Cl); 145.0, 147.9 (—HC═C—) 162.9 (C═N—); 172.7, 203.9 (C═O) ppm. $C_{31}H_{37}Cl_2NO_5$ (574.5) LC-MS: m/z (%)=574 ($M^+$); $R_t$=8.74 min.

Example (I-2)

(E/Z)-17-β-desosaminyl-9-[2-chloro-pyrid-5-yl-methoximino)-spinosyn A

The 17-β-desosaminyl-9-keto spinosyn A 9-pseudoaglycone [compound according to the general formula (II), where $R^1$ stands for the desosaminyl moiety and A-B stands for the group —HC═CH—] can be produced according to WO 02/079184.

287.5 mg (0.515 mmol) of 17-β-desosaminyl-9-keto spinosyn A 9-pseudoaglycone is stirred in 25 ml absolute pyridine and mixed with 327.0 g (2.06 mmol) O-(2-chloro-pyrid-5-yl-methy)-hydroxylamine. After stirring for 24 hours at 25° C., the entire reaction preparation is concentrated in vacuum. Column chromatography on silica gel is then performed (silica gel 60-Merck, grain size: 0.04 to 0.063 mm) using dichloromethane/methanol (10:1) as mobile phases, and the (E/Z)-isomer mixture is separated. The reaction yields 128 mg (35.5% of the theoretical yield) of (Z)-17-β-desosaminyl-9-[2-chloro-pyrid-5-yl-methoximino)-spinosyn A and 68.9 mg (19.1% of the theoretical yield) of (E)-17-β-desosaminyl-9-[2-chloro-pyrid-5-yl-methoximino)-spinosyn A.

(Z)-17-β-desosaminyl-9-[2-chloro-pyrid-5-yl-methoximino)-spinosyn A $^{13}C$-NMR: DMF-$d_7$, δ=32.5 (C-10); 35.5 (C-8) ppm. $C_{38}H_{52}ClN_3O_7$ (698.3) LC-MS: m/z (%)=698 ($M^+$); $R_t$=5.98 min.

(E)-17-β-desosaminyl-9-[2-chloro-pyrid-5-yl-methoximino)-spinosyn A $^{13}C$-NMR: DMF-$d_7$, δ=35.3 (C-10); 33.3 (C-8) ppm. $C_{38}H_{52}ClN_3O_7$ (698.3) LC-MS: m/z (%)=698 ($M^+$); $R_t$=5.68 min.

Example (I-3)

(E/Z)-9-[N-(4-trifluoromethoxy-phenyl-aminocarbonyl)-hydrazono)-spinosyn A-aglycone The 9-keto spinosyn A-aglycone [compound according to the general formula (II), where $R^1$ stands for hydrogen and A-B stands for the group —HC═CH—] can be produced according to WO 02/079184.

150.0 mg (0.375 mmol) of 9-keto spinosyn A-aglycone is stirred in 20 ml abs. pyridine and mixed with 353.3 mg (1.49 mmol) 4-(trifluoromethoxy-phenyl)-semicarbazide. After stirring for 24 hours at 25° C., the entire reaction preparation is concentrated in vacuum. Next, an initial purification procedure is performed using column chromatography on silica gel (silica gel 60-Merck, grain size: 0.04 to 0.063 mm) using cyclohexane/acetone (2:1) as mobile phases, and then column chromatography is performed a second time using cyclohexane: acetone (3:1) as mobile phases. The (E/Z)-isomer mixture is then separated using preparative HPLC. The reaction yields 56.2 mg (24.3% of the theoretical yield) of (Z)-9-[N-(4-trifluoromethoxy-phenyl-aminocarbonyl)-hydrazono)-spinosyn A-aglycone and 92.0 mg (39.7% of the theoretical yield) of (E)-9-[N-(4-trifluoromethoxy-phenyl-aminocarbonyl)-hydrazono)-spinosyn A-aglycone.

(Z)-9-[N-(4-trifluoromethoxy-phenyl-aminocarbonyl)-hydrazono)-spinosyn A-aglycone $^{13}C$-NMR (DMF-$d_7$, δ)=32.9 (C-10); 38.0 (C-8) ppm. $C_{32}H_{38}F3N_3O_6$ (617.6) LC-MS: m/z (%)=618 ($MH^+$); $R_t$=7.69 min.

(E)-9-[N-(4-trifluoromethoxy-phenyl-aminocarbonyl)-hydrazono)-spinosyn A-aglycone $C_{32}H_{38}F3N_3O_6$ (617.6) LC-MS: m/z (%)=618 ($MH^+$); $R_t$=7.59 min.

In a similar manner to the previous examples I-1 to I-3, the spinosyn derivatives listed below in Table 3 can be produced according to the general formula (I).

TABLE 3
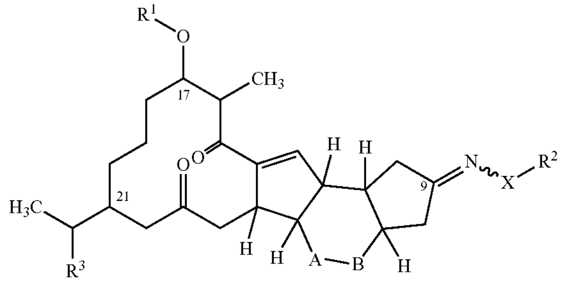
(I)
| Ex. No. | Isomer[a] | $R^1$ | X | $R^2$ | A-B | $R^3$ | Physical Data[b] |
|---|---|---|---|---|---|---|---|
| I-4 | Z | H | O | -Me | —HC═CH— | H | 32.3 (C-10); 35.8 (C-8) ($CD_3CN$). 430 ($MH^+$, 100); 6.36 min $C_{25}H_{35}NO_3$ (429.5) |
| I-5 | E | H | O | -Me | —HC═CH— | H | 35.2 (C-10); 32.9 (C-8) ($CD_3CN$). 430 ($MH^+$, 100); 6.51 min $C_{25}H_{35}NO_3$ (429.5) |
| I-6 | Z | H | O | $—CH_2—O—CH_2—CH_2—O—Me$ | —HC═CH— | H | 32.7 (C-10); 35.8 (C-8) ($CD_3CN$). 504 ($MH^+$, 100); 6.14 min $C_{28}H_{41}NO_7$ (503.6) |
| I-7 | E | H | O | $—CH_2—O—CH_2—CH_2—O—Me$ | —HC═CH— | H | 504 ($MH^+$, 100); 6.29 min $C_{28}H_{41}NO_7$ (503.6) |
| I-8 | Z | H | O | 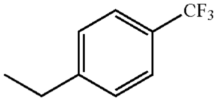 | —HC═CH— | H | 574 ($MH^+$, 100); 8.19 min $C_{32}H_{38}F_3NO_5$ (57.,6) |
| I-9 | E | H | O | 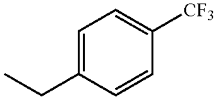 | —HC═CH— | H | 35.3 (C-10); 33.3 (C-8) ($CD_3CN$). 574 ($MH^+$, 100); 8.36 min $C_{32}H_{38}F_3NO_5$ (573.6) |
| I-10 | Z | H | O | 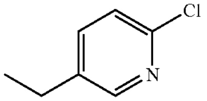 | —HC═CH— | H | 32.5 (C-10); 35.5 (C-8) (DMF-$d_7$). 541 ($M^+$, 100); 7.12 min $C_{30}H_{37}ClN_2O_5$ (541.0) |

TABLE 3-continued
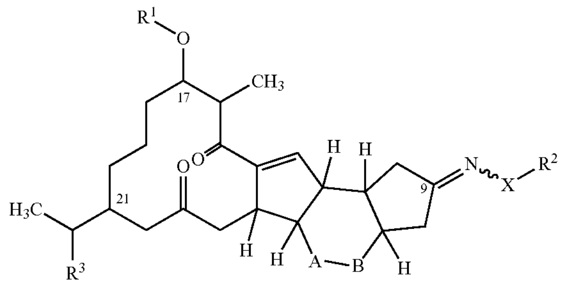
(I)
| Ex. No. | Isomer[a] | $R^1$ | X | $R^2$ | A-B | $R^3$ | Physical Data[b] |
|---|---|---|---|---|---|---|---|
| I-11 | E | H | O | 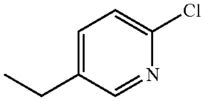 | —HC=CH— | H | 35.3 (C-10); 33.3 (C-8) (DMF-$d_7$). 541 ($M^+$, 100); 7.24 min $C_{30}H_{38}ClN_2O_5$ (541.0) |
| I-12 | Z | H | O | 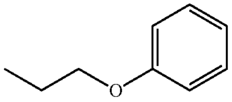 | —HC=CH— | H | 32.6 (C-10); 35.8 (C-8) ($CD_3CN$). 536 ($MH^+$, 100); 7.62 min $C_{32}H_{41}NO_6$ (535.7) |
| I-13 | E | H | O | 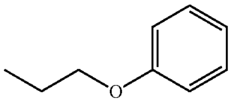 | —HC=CH— | H | 536 ($MH^+$, 100); 7.72 min $C_{32}H_{41}NO_6$ (535.7) |
| I-14 | Z | H | O | —H | —HC=CH— | H | 31.6 (C-10); 35.5 (C-8) (DMF-$d_7$). 416 ($MH^+$, 100); 5.22 min $C_{24}H_{33}NO_5$ (415.5) |
| I-15 | E | H | O | —H | —HC=CH— | H | 35.1 (C-10); 32.3 (C-8) (DMF-$d_7$). 416 ($MH^+$, 100); 5.34 min $C_{24}H_{33}NO_5$ (415.5) |
| I-16 | Z | H | O | 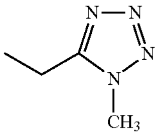 | —HC=CH— | H | 32.5 (C-10); 35.8 (C-8) ($CD_3CN$). 512 ($MH^+$, 100); 5.88 min $C_{27}H_{37}N_5O_5$ (511.6) |

TABLE 3-continued
(I)
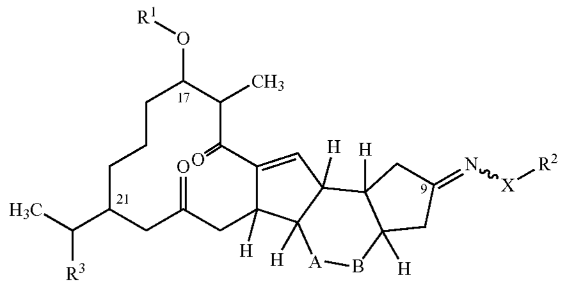
| Ex. No. | Isomer[a] | R[1] | X | R[2] | A-B | R[3] | Physical Data[b] |
|---|---|---|---|---|---|---|---|
| I-17 | Z | H | O | 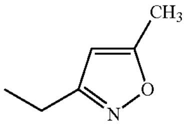 | —HC═CH— | H | 32.6 (C-10); 35.8 (C-8) ($CD_3CN$). 511 ($MH^+$, 100); 6.73 min $C_{29}H_{38}N_2O_6$ (510.6) |
| I-18 | E | H | O | 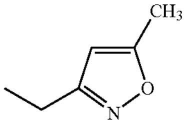 | —HC═CH— | H | 511 ($MH^+$, 100); 6.79 min $C_{29}H_{38}N_2O_6$ (510.6) |
| I-19 | Z | H | NH | 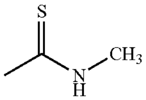 | —HC═CH— | H | 32.8 (C-10); 38.2 (C-8) ($CD_3CN$). 488 ($MH^+$, 100); 5.98 min $C_{26}H_{37}N_3O_4S$ (487.6) |
| I-20 | E | H | NH | 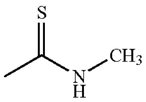 | —HC═CH— | H | 37.8 (C-10); 33.5 (C-8) ($CD_3CN$). 488 ($MH^+$, 100); 5.98 min $C_{26}H_{37}N_3O_4S$ (487.6) |
| I-21 | Z | H | O | 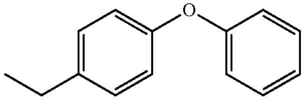 | —HC═CH— | H | 598 ($MH^+$, 100); 8.53 min $C_{37}H_{43}NO_6$ (597.7) |

TABLE 3-continued
(I)
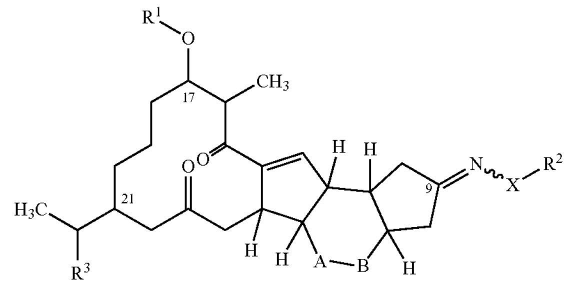
| Ex. No. | Isomer[a] | $R^1$ | X | $R^2$ | A-B | $R^3$ | Physical Data[b] |
|---|---|---|---|---|---|---|---|
| I-22 | E | H | O | 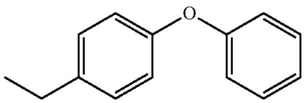 | —HC=CH— | H | 35.0 (C-10); 33.0 (C-8) (DMF-$d_7$). 598 ($MH^+$, 100), 8.67 min $C_{37}H_{43}NO_6$ (597.7) |
| I-23 | Z | H | O | 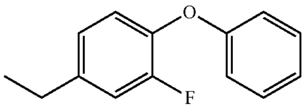 | —HC=CH— | H | 32.7 (C-10); 35.8 (C-8) ($CD_3CN$). 616 ($MH^+$, 100); 8.43 min $C_{37}H_{42}FNO_6$ (615.7) |
| I-24 | E | H | O | 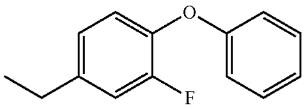 | —HC=CH— | H | 616 ($MH^+$, 100); 8.56 min $C_{37}H_{42}FNO_6$ (615.7) |
| I-25 | Z | H | O | 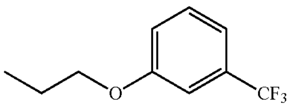 | —HC=CH— | H | 32.6 (C-10); 35.8 (C-8) ($CD_3CN$). 604 ($MH^+$, 100); 8.20 min $C_{33}H_{40}F_3NO_6$ (603.6) |
| I-26 | E | H | O | 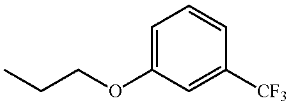 | —HC=CH= | H | 604 ($MH^+$, 100); 8.31 min $C_{33}H_{40}F_3NO_6$ (603.6) |

TABLE 3-continued
(I)
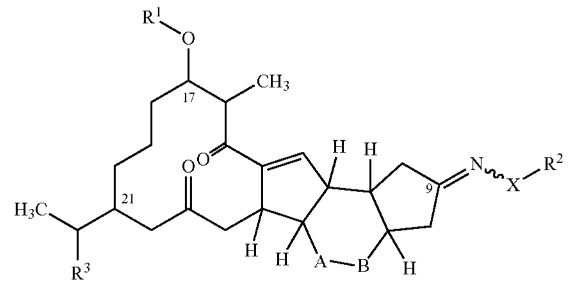
| Ex. No. | Isomer[a] | $R^1$ | X | $R^2$ | A-B 	| $R^3$ | Physical Data[b] |
|---|---|---|---|---|---|---|---|
| I-27 | Z | H | O | 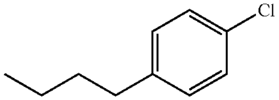 | —HC═CH— | H | 32.3 (C-10); 36.0 (C-8) (DMF-$d_7$). 568 ($M^+$, 100); 8.59 min $C_{33}H_{42}ClNO_5$ (568.1) |
| I-28 | E | H | O | 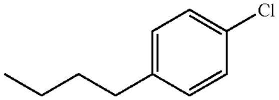 | —HC═CH— | H | 568 ($M^+$, 100); 8.85 min $C_{33}H_{42}ClNO_5$ (568.1) |
| I-29 | Z | H | O | 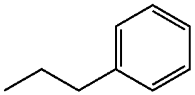 | —HC═CH— | H | 32.6 (C-10); 35.8 (C-8) ($CD_3CN$). 520 ($MH^+$, 100); 7.92 min $C_{32}H_{41}NO_5$ (519.7) |
| I-30 | E | H | O | 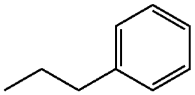 | —HC═CH— | H | 520 ($MH^+$, 100); 8.08 min $C_{32}H_{41}NO_5$ (519.7) |
| I-31 | Z | H | O | 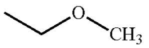 | —HC═CH— | H | 32.6 (C-10); 35.8 (C-8) ($CD_3CN$). 460 ($MH^+$, 100); 6.22 min $C_{26}H_{37}NO_6$ (459.5) |
| I-32 | Z | H | O | 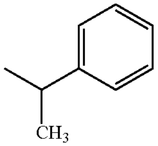 | —HC═CH— | H | 520 ($MH^+$, 100); 7.86 min $C_{32}H_{41}NO_5$ (519.6) |

TABLE 3-continued
(I)
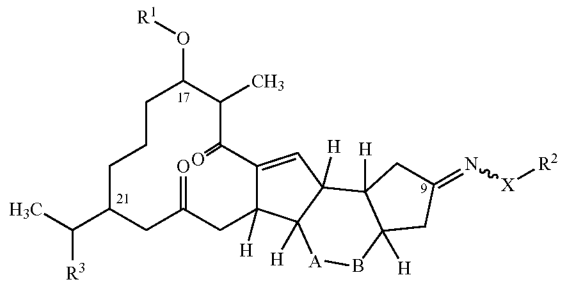
| Ex. No. | Isomer[a] | $R^1$ | X | $R^2$ | A-B | $R^3$ | Physical Data[b] |
|---|---|---|---|---|---|---|---|
| I-33 | E | H | O | 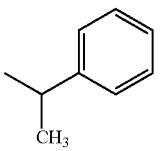 | —HC═CH— | H | 32.7 (C-10); 35.8 (C-8) ($CD_3CN$). 520 ($MH^+$, 100); 8.17 min $C_{32}H_{41}NO_5$ (519.6) |
| I-34 | Z | H | O | 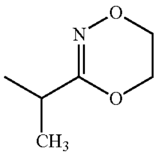 | —HC═CH— | H | 32.7 (C-10); 35.8 (C-8) ($CD_3CN$). 529 ($MH^+$, 100); 6.18 min $C_{29}H_{40}N_2O_7$ (528.6) |
| I-35 | E | H | O | 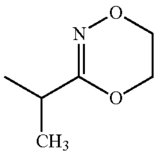 | —HC═CH— | H | 35.3 (C-10); 33.2 (C-8) ($CD_3CN$). 529 ($MH^+$, 100); 6.40 min $C_{29}H_{40}N_2O_7$ (528.6) |
| I-36 | Z | H | O | 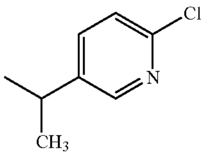 | —HC═CH— | H | 32.7 (C-10); 35.8 (C-8) ($CD_3CN$). 555 ($M^+$, 100); 7.38 min $C_{31}H_{39}N_2O_5$ (555.1) |

TABLE 3-continued
(I)
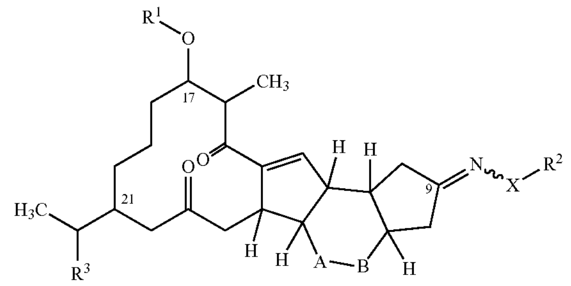
| Ex. No. | Isomer[a] | $R^1$ | X | $R^2$ | A-B 	| $R^3$ | Physical Data[b] |
|---|---|---|---|---|---|---|---|
| I-37 | E | H | O | 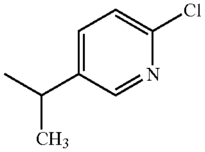 | —HC═CH— | H | 555 ($M^+$, 100); 7.60 min<br>$C_{31}H_{39}N_2O_5$ (555.1) |
| I-38 | Z | H | O | 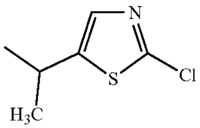 | —HC═CH— | H | 561 ($M^+$, 100); 7.81 min<br>$C_{29}H_{37}ClN_2O_5O$ (561.1) |
| I-39 | E | H | O | 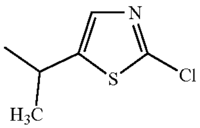 | —HC═CH— | H | 35.4 (C-10); 33.4 (C-8) ($CD_3CN$).<br>561 ($M^+$, 100); 8.02 min<br>$C_{29}H_{37}ClN_2O_5S$ (561.1) |
| I-40 | Z | H | O | 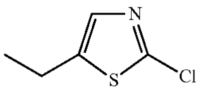 | —HC═CH— | H | 32.5 (C-10); 35.5 (C-8) (DMF-$d_7$).<br>547 ($M^+$, 100); 7.53 min<br>$C_{28}H_{35}clN_2O_5S$ (547.1) |
| I-41 | Z | H | O | 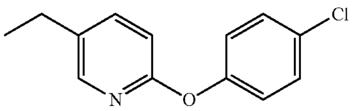 | —HC═CH— | H | 32.5 (C-10); 35.5 (C-8) (DMF-$d_7$).<br>633 ($M^+$, 100); 8.28 min<br>$C_{36}H_{41}ClN_2O_6$ (633.1) |

TABLE 3-continued
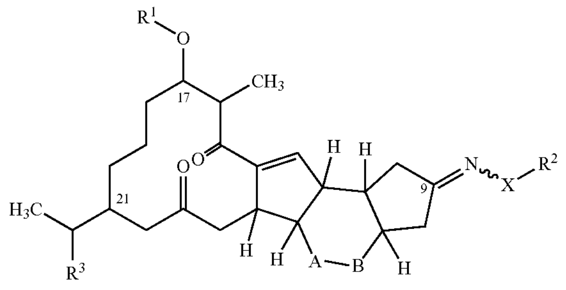
(I)
| Ex. No. | Isomer[a] | $R^1$ | X | $R^2$ | A-B | $R^3$ | Physical Data[b] |
|---|---|---|---|---|---|---|---|
| I-42 | Z | H | O | 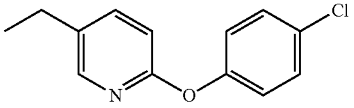 | —HC═CH— | H | 633 (Me, 100); 8.37 min $C_{36}H_{41}ClN_2O_6$ (633.1) |
| I-43 | Z | H | O | 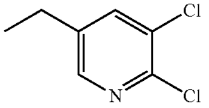 | —HC═CH— | H | 32.5 (C-10); 35.5 (C-8) (DMF-$d_7$). 575 ($M^+$, 100); 7.84 min $C_{30}H_{36}Cl_2N_2O_5$ (575.5) |
| I-44 | E | H | O | 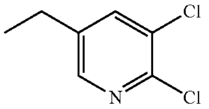 | —HC═CH— | H | 575 ($M^+$, 100); 7.99 min $C_{30}H_{36}Cl_2N_2O_5$ (575.5) |
| I-45 | Z | H | O | 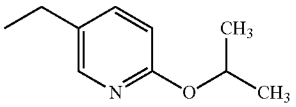 | —HC═CH— | H | 32.6 (C-10); 35.8 (C-8) ($CD_3CN$). 565 ($MH^+$, 100); 7.45 min $C_{33}H_{44}N_2O_6$ (564.7) |
| I-46 | E | H | O | 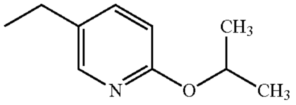 | —HC═CH— | H | 565 ($MH^+$, 100); 8.01 min $C_{33}H_{44}N_2O_6$ (564.7) |

TABLE 3-continued
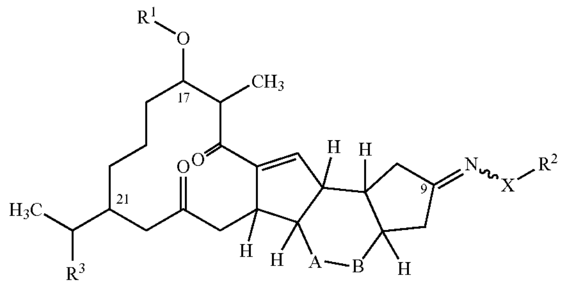
(I)
| Ex. No. | Isomer[a] | $R^1$ | X | $R^2$ | A-B | $R^3$ | Physical Data[b] |
|---|---|---|---|---|---|---|---|
| I-47 | Z | H | O | 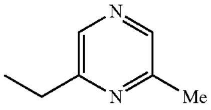 | —HC═CH— | H | 522 ($MH^+$, 100); 6.22 min $C_{30}H_{39}N_3O_5$ (521.6) |
| I-48 | E | H | O | 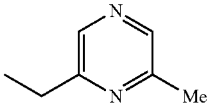 | —HC═CH— | H | 35.3 (C-10); 33.3 (C-8) ($CD_3CN$). 522 ($MH^+$, 100); 6.27 min $C_{30}H_{39}N_3O_5$ (521.6) |
| I-49 | Z | H | O | 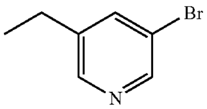 | —HC═CH— | H | 587 ($MH^+$, 100); 7.17 min $C_{30}H_{37}BrN_2O_5$ (585.5) |
| I-50 | E | H | O | 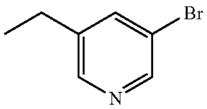 | —HC═CH— | H | 35.1 (C-10); 33.1 (C-8) ($CD_3CN$). 587 ($MH^+$, 100); 7.32 min $C_{30}H_{37}BrN_2O_5$ (585.5) |
| I-51 | Z | H | O | 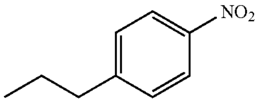 | —HC═CH— | H | 32.6 (C-10); 35.8 (C-8) ($CD_3CN$). 565 ($MH^+$, 100); 7.67 min $C_{32}H_{40}N_2O_7$ (564.6) |

TABLE 3-continued
(I)
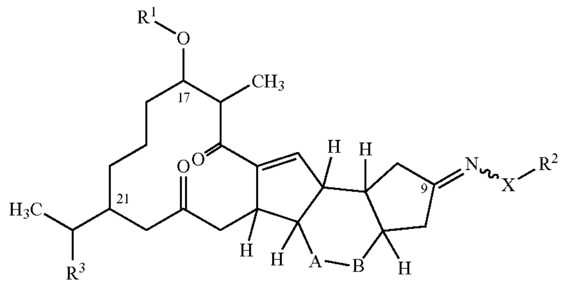
| Ex. No. | Isomer[a] | R[1] | X | R[2] | A-B | R[3] | Physical Data[b] |
|---|---|---|---|---|---|---|---|
| I-52 | Z | H | O | 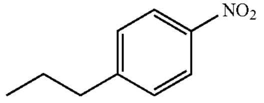 | —HC═CH— | H | 35.3 (C-10); 35.0 (C-8) ($CD_3CN$). 565 ($MH^+$, 100); 7.71 min $C_{32}H_{40}N_2O_7$ (564.6) |
| I-53 | Z | H | O | 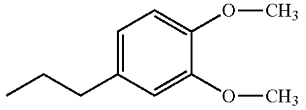 | —HC═CH— | H | 32.5 (C-10); 35.5 (C-8) (DMF-$d_7$). 580 ($MH^+$, 100); 7.36 min $C_{34}H_{45}NO_7$ (579.7) |
| I-54 | E | H | O | 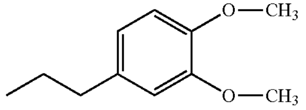 | —HC═CH— | H | 35.0 (C-10); 33.0 (C-8) (DMF-$d_7$). 580 ($MH^+$, 100); 7.36 min $C_{34}H_{45}NO_7$ (579.7) |
| I-55 | Z | H | O | 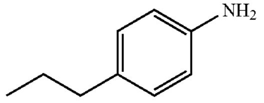 | —HC═CH— | H | 32.4 (C-10); 35.5 (C-8) (DMF-$d_7$). 535 ($MH^+$, 100); 5.33 min $C_{32}H_{42}N_2O_5$ (534.6) |
| I-56 | E | H | O | 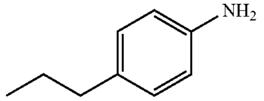 | —HC═CH— | H | 35.0 (C-10); 33.0 (C-8) (DMF-$d_7$). 535 ($MH^+$, 100); 5.23 min $C_{32}H_{42}N_2O_5$ (534.6) |

TABLE 3-continued
(I)
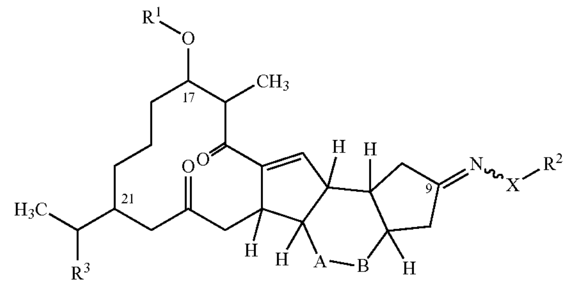
| Ex. No. | Isomer[a] | R1 | X | R2 | A-B | R3 | Physical Data[b] |
|---|---|---|---|---|---|---|---|
| I-57 | Z | H | O | 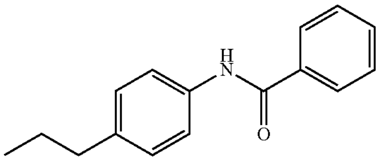 | —HC═CH— | H | 32.4 (C-10); 35.5 (C-8) (DMF-$d_7$). 621 ($M^+$); 7.53 min $C_{39}H_{45}N_2O_5$ (621.8) |
| I-58 | Z | H | O | 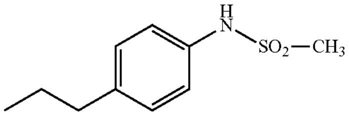 | —HC═CH— | H | 32.4 (C-10); 35.5 (C-8) (DMF-$d_7$). 613 ($MH^+$, 100); 6.77 min $C_{33}H_{44}N_2O_7S$ (612.7) |
| I-59 | E | H | O | 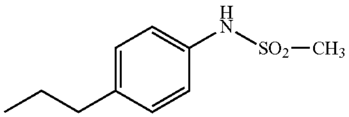 | —HC═CH— | H | 35.0 (C-10); 33.0 (C-8) (DMF-$d_7$). 613 ($MH^+$, 100)/6.63 min $C_{33}H_{44}N_2O_7S$ (612.7) |
| I-60 | Z | 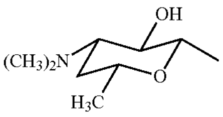 | O | 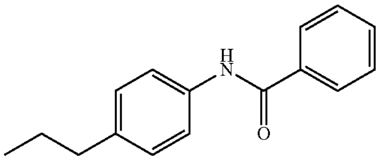 | —HC═CH— | H | 33.0 (C-10); 35.0 (C-8) (DMF-$d_7$). 796 ($M^+$, 100); 6.09 min $C_{47}H_{61}N_3O_8$ (796.0) |

TABLE 3-continued
(I)
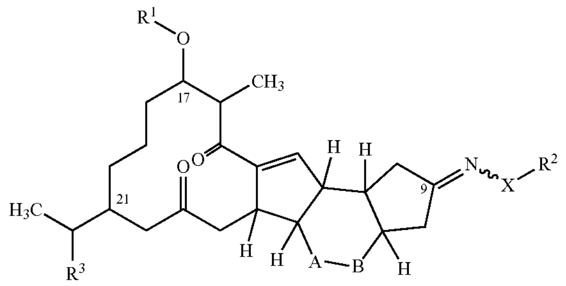
| Ex. No. | Isomer[a] | $R^1$ | X | $R^2$ | A-B | $R^3$ | Physical Data[b] |
|---|---|---|---|---|---|---|---|
| I-61 | E | 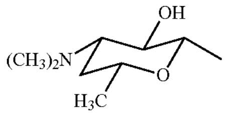 | O | 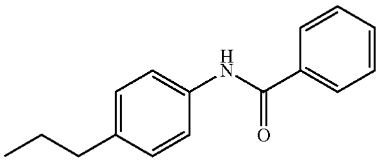 | —HC═CH— | H | 35.6 (C-10); 32.4 (C-8) (DMF-$d_7$). 796 ($M^+$, 100); 5.89 min $C_{47}H_{61}N_3O_8$ (796.0) |
| I-62 | Z | 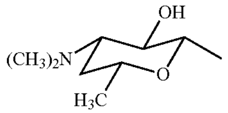 | O | 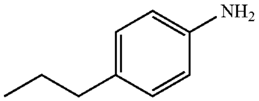 | —HC═CH— | H | 32.4 (C-10); 35.5 (C-8) (DMF-$d_7$). 692 ($MH^+$, 100); 4.48 min $C_{40}H_{57}N_3O_7$ (691.9) |
| I-63 | E | 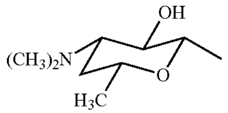 | O | 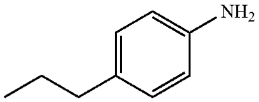 | —HC═CH— | H | 35.1 (C-10); 33.0 (C-8) (DMF-$d_7$). 692 ($MH^+$, 100); 4.48 min $C_{40}H_{57}N_3O_7$ (691.9) |
| I-64 | Z | H | O | 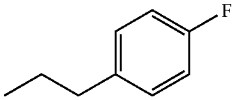 | —HC═CH— | H | 32.5 (C-10); 35.5 (C-8) (DMF-$d_7$). 538 ($M^+$, 100); 7.89 min $C_{32}H_{40}N_2FNO_5$ (537.6) |
| I-65 | E | H | O | 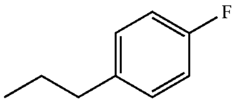 | —HC═CH— | H | 538 ($MH^+$, 100); 8.01 min $C_{32}H_{40}N_2FNO_5$ (537.6) |

TABLE 3-continued
(I)
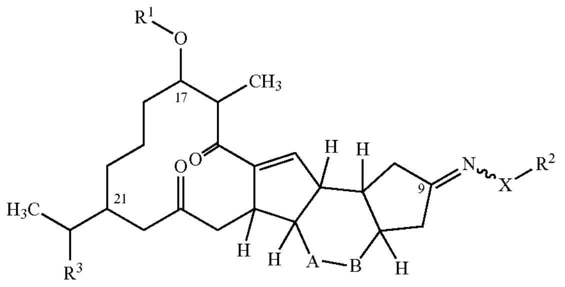
| Ex. No. | Isomer[a] | R1 | X | R2 | A-B | R3 | Physical Data[b] |
|---|---|---|---|---|---|---|---|
| I-66 | Z | H | O | 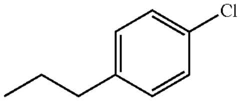 | —HC═CH— | H | 554 ($M^+$, 100); 8.28 min $C_{32}H_{40}ClNO_5$ (554.1) |
| I-67 | E | H | O | 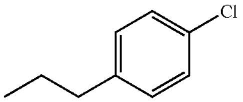 | —HC═CH— | H | 35.0 (C-10); 33.0 (C-8) (DMF-$d_7$). 554 ($MH^+$, 100); 8.48 min $C_{32}H_{40}ClNO_5$ (554.1) |
| I-68 | Z | 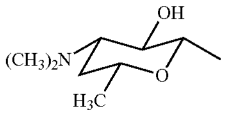 | O | 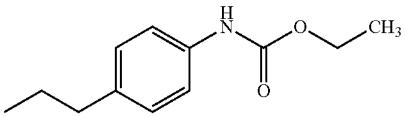 | —HC═CH— | H | 764 (MH, 100); 6.06 min $C_{43}H_{61}N_3O_9$ (763.9) |
| I-69 | E | 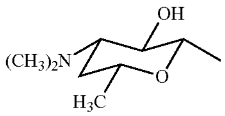 | O | 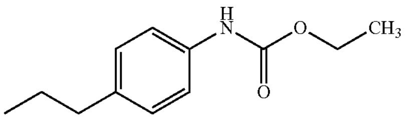 | —HC═CH— | H | 35.0 (C-10); 33.0 (C-8) (DMF-$d_7$). 764 ($MH^+$, 100); 6.08 min $C_{43}H_{61}N_3O_9$ (763.9) |
| I-70 | Z | 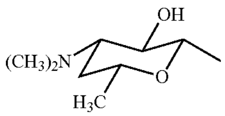 | O | 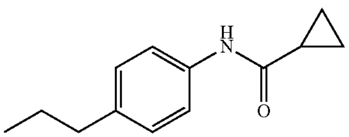 | —HC═CH— | H | 760 ($MH^+$, 100); 5.63 min $C_{44}H_{61}N_3O_8$ (759.9) |

TABLE 3-continued
(I)
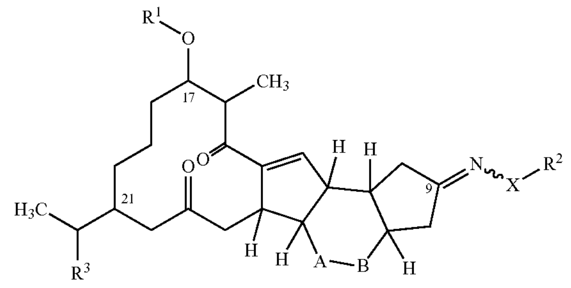
| Ex. No. | Isomer[a] | R[1] | X | R[2] | A-B | R[3] | Physical Data[b] |
|---|---|---|---|---|---|---|---|
| I-71 | E | 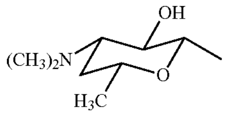 | O | 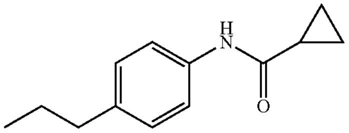 | —HC═CH— | H | 34.9 (C-10); 33.0 (C-8) (DMF-$d_7$). 760 ($MH^+$, 100); 5.76 min $C_{44}H_{61}N_3O_8$ (759.9) |
| I-72 | Z | 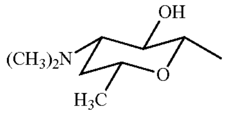 | O | 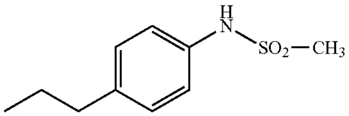 | —HC═CH— | H | 770 ($M^+$, 100)/5.66 min $C_{41}H_{59}N_3O_9S$ (770) |
| I-73 | E | 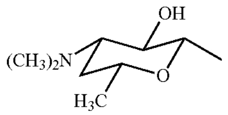 | O | 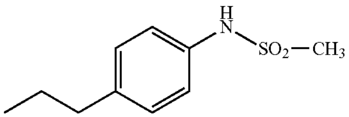 | —HC═CH— | H | 34.9 (C-10); 33.0 (C-8) (DMF-$d_7$). 770 ($M^+$, 100)/5.63 min $C_{41}H_{59}N_3O_9S$ (770) |
| I-74 | Z | H | O | 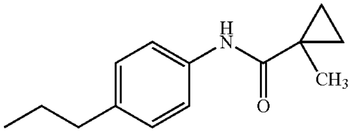 | —HC═CH— | H | 32.4 (C-10); 35.5 (C-8) (DMF-$d_7$). 617 ($MH^+$, 100); 7.34 min $C_{37}H_{48}N_2O_6$ (616.7) |
| I-75 | E | H | O | 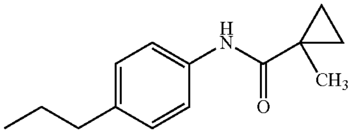 | —HC═CH— | H | 35.0 (C-10); 32.9 (C-8) (DMF-$d_7$). 617 ($MH^+$, 100); 7.36 min $C_{37}H_{48}N_2O_6$ (616.7) |

TABLE 3-continued
(I)
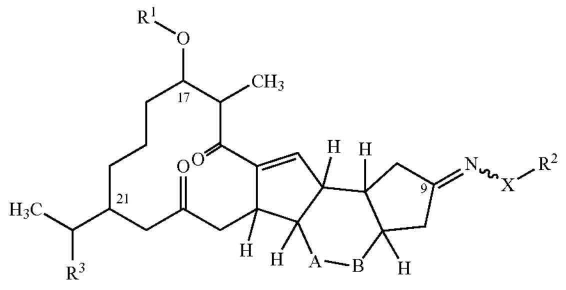
| Ex. No. | Isomer[a] | $R^1$ | X | $R^2$ | A-B | $R^3$ | Physical Data[b] |
|---|---|---|---|---|---|---|---|
| I-76 | Z | H | O | 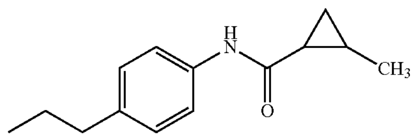 | —HC═CH— | H | 32.4 (C-10); 35.5 (C-8) (DMF-$d_7$). 617 ($MH^+$, 100); 7.16 min $C_{37}H_{48}N_2O_6$ (616.7) |
| I-77 | E | H | O | 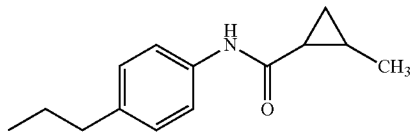 | —HC═CH— | H | 35.0 (C-10); 33.0 (C-8) (DMF-$d_7$). 617 ($MH^+$, 100); 7.30 min $C_{37}H_{48}N_2O_6$ (616.7) |
| I-78 | Z | H | O | 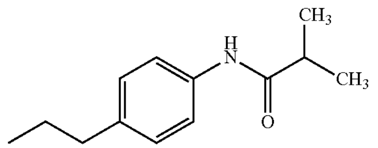 | —HC═CH— | H | 32.4 (C-10); 35.5 (C-8) (DMF-$d_7$). 605 ($MH^+$, 100); 7.16 min $C_{36}H_{48}N_2O_6$ (604.7) |
| I-79 | E | H | O | 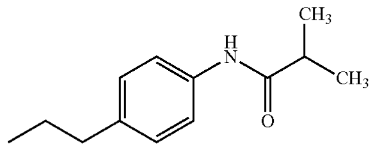 | —HC═CH— | H | 35.0 (C-10); 33.0 (C-8) (DMF-$d_7$). 605 ($MH^+$, 100); 7.11 min $C_{36}H_{48}N_2O_6$ (604.7) |

TABLE 3-continued
(I)
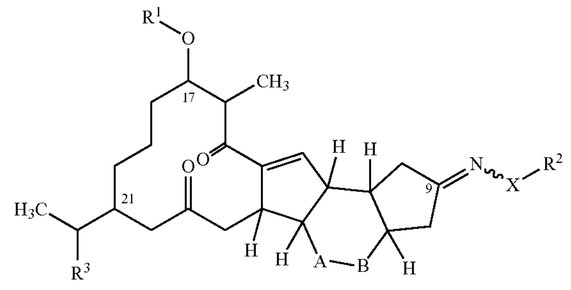
| Ex. No. | Isomer[a] | $R^1$ | X | $R^2$ | A-B | $R^3$ | Physical Data[b] |
|---|---|---|---|---|---|---|---|
| I-80 | Z | H | O | 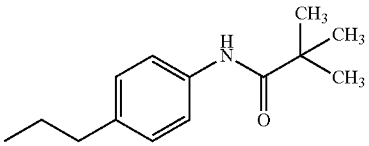 | —HC═CH— | H | 32.4 (C-10); 35.5 (C-8) (DMF-$d_7$). 619 ($MH^+$, 100); 7.49 min $C_{37}H_{50}N_2O_6$ (618.8) |
| I-81 | E | H | O | 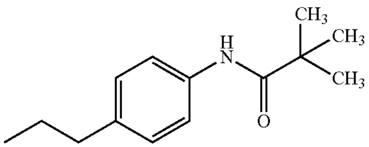 | —HC═CH— | H | 35.0 (C-10); 33.0 (C-8) (DMF-$d_7$). 619 ($MH^+$, 100); 7.54 min $C_{37}H_{50}N_2O_6$ (618.8) |
| I-82 | Z | H | O | 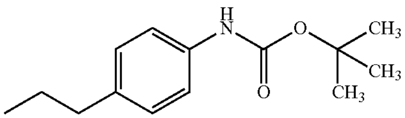 | —HC═CH— | H | 635 ($MH^+$, 100); 8.06 min $C_{37}H_{50}N_2O_7$ (634.8) |
| I-83 | E | H | O | 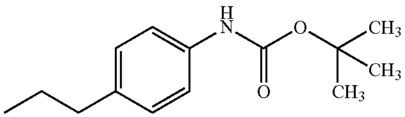 | —HC═CH— | H | 35.0 (C-10); 33.0 (C-8) (DMF-$d_7$). 635 ($MH^+$, 100); 8.08 min $C_{37}H_{50}N_2O_7$ (634.8) |
| I-84 | E | H | O | 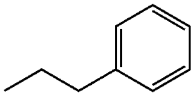 | —$H_2C$—$CH_2$— | H | 34.0 (C-8); 36.1 (C-10) ($CDCl_3$); 2.04 (t, 10-H) ($CDCl_3$); 522 ($MH^+$, 100)/7.79 min; 7.21 min; $C_{32}H_{43}NO_5$ (521.7) |

TABLE 3-continued

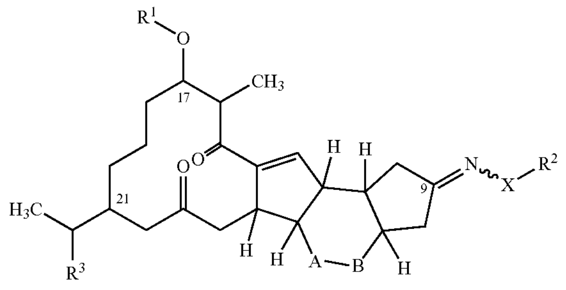

(I)

| Ex. No. | Isomer[a] | $R^1$ | X | $R^2$ | A-B | $R^3$ | Physical Data[b] |
|---|---|---|---|---|---|---|---|
| I-85 | Z | H | O | 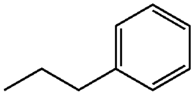 | $—H_2C—CH_2—$ | H | 33.3 (C-10); 36.8 (C-8) ($CDCl_3$); no triplet between 2.0–2.1 ($CDCl_3$); 522 ($MH^+$, 100)/7.61 min; 7.03 min; $C_{32}H_{43}NO_5$ (521.7) |
| I-86 | E | H | O | 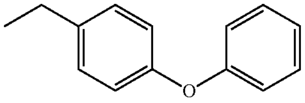 | $—H_2C—CH_2—$ | H | 2.03 (t; H-10) ($CDCl_3$); 600 ($MH^+$, 100)/8.47 min; 7.90 min; $C_{37}H_{45}NO_6$ (599.8) |
| I-87 | Z | H | O | 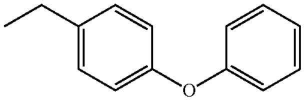 | $—H_2C—CH_2—$ | H | No triplet between 2.0–2.1 ($CDCl_3$); 600 ($MH^+$, 100)/8.22 min; 7.65 min; $C_{37}H_{45}NO_6$ (599.8) |
| I-88 | E | H | O | 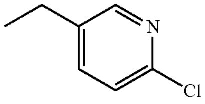 | $—H_2C—CH_2—$ | H | 2.03 (t, H-10) ($CDCl_3$); 543 ($MH^+$, 100)/6.97 min; 6.38 min; $C_{30}H_{39}ClN_2O_5$ (543.1) |
| I-89 | Z | H | O | 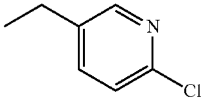 | $—H_2C—CH_2—$ | H | No triplet between 2.0–2.1 ($CDCl_3$); 543 ($MH^+$, 100)/6.89 min; 6.33 min; $C_{30}H_{30}ClN_2O_5$ (543.1) |
| I-90 | E | H | O | 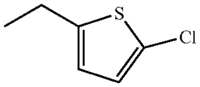 | $—H_2C—CH_2—$ | H | 2.05 (t, H-10) ($CDCl_3$); 548 ($MH^+$, 100)/8.10 min; 7.52 min; $C_{29}H_{38}ClNO_5S$ (548.1) |

TABLE 3-continued
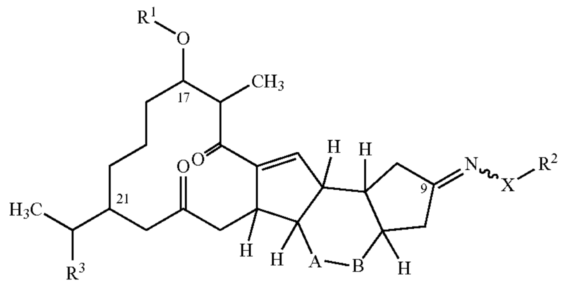
(I)
| Ex. No. | Isomer[a] | $R^1$ | X | $R^2$ | A-B | $R^3$ | Physical Data[b] |
|---|---|---|---|---|---|---|---|
| I-91 | Z | H | O | 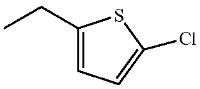 | $—H_2C—CH_2—$ | H | No triplet between 2.0–2.1 ($CDCl_3$); 548 ($MH^+$, 100)/7.95 min; 7.37 min; $C_{29}H_{38}ClNO_5S$ (548.1) |
| I-92 | E | H | O | 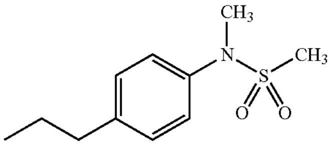 | $—H_2C—CH_2—$ | H | 2.04 (t, H-10) ($CDCl_3$); 629 ($MH^+$, 100)/6.71 min; 6.13 min; $C_{34}H_{48}N_2O_7S$ (628.8) |
| I-93 | Z | H | O | 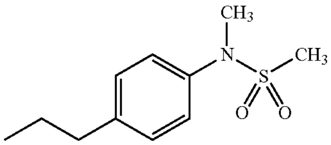 | $—H_2C—CH_2—$ | H | No triplet between 2.0–2.1 ($CDCl_3$); 629 ($MH^+$, 100)/6.77 min; 6.19 min; $C_{34}H_{48}N_2O_7S$ (628.8) |
| I-94 | E | H | O | 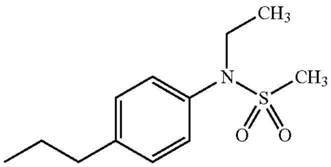 | $—H_2C—CH_2—$ | H | 2.05 (t, H-10) ($CDCl_3$); 643 ($MH^+$, 100)/6.96 min; 6.37 min; $C_{35}H_{50}N_2O_7S$ (642.9) |

TABLE 3-continued
(I)
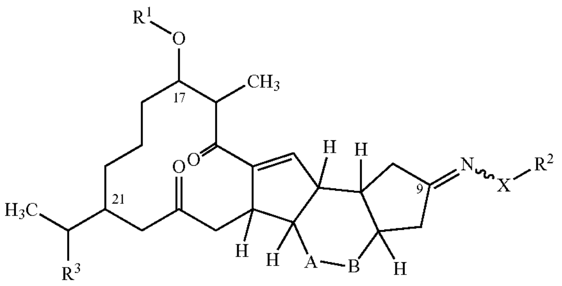
| Ex. No. | Isomer[a] | R[1] | X | R[2] | A-B | R[3] | Physical Data[b] |
|---|---|---|---|---|---|---|---|
| I-95 | Z | H | O | 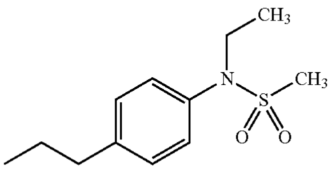 | —$H_2C$—$CH_2$— | H | No triplet between 2.0–2.1 ($CDCl_3$); 643 ($MH^+$, 100)/7.05 min; 6.50 min; $C_{35}H_{50}N_2O_7S$ (642.9) |
| I-96 | E | H | O | 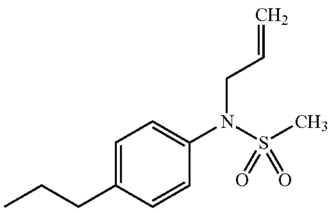 | —$H_2C$—$CH_2$— | H | 2.05 (t, H-10) ($CDCl_3$); 655 ($MH^+$, 100)/7.04 min; 6.45 min $C_{36}H_{50}N_2O_7S$ (654.9) |
| I-97 | Z | H | O | 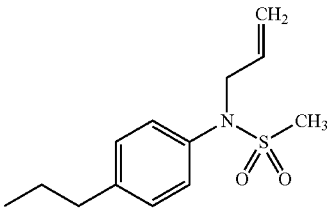 | —$H_2C$—$CH_2$— | H | No triplet between 2.0–2.1 ($CDCl_3$); 655 ($MH^+$, 100)/7.09 min; 6.51 min; $C_{36}H_{50}N_2O_7S$ (654.9) |

TABLE 3-continued
(I)
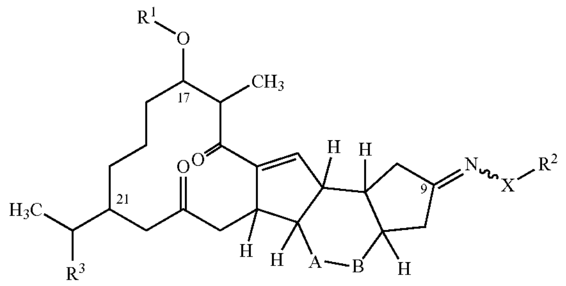
| Ex. No. | Isomer[a] | $R^1$ | X | $R^2$ | A-B | $R^3$ | Physical Data[b] |
|---|---|---|---|---|---|---|---|
| I-98 | E | H | O | 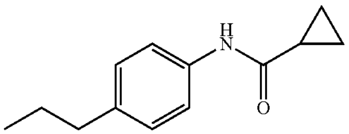 | $-H_2C-CH_2-$ | H | 2.04 (t, H-10) ($CDCl_3$); 605 ($MH^+$, 100)/6.71 min; 6.12 min; $C_{36}H_{48}N_2O_6$ (604.8) |
| I-99 | Z | H | O | 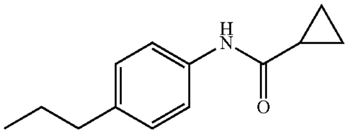 | $-H_2C-CH_2-$ | H | No triplet between 2.0–2.1 ($CDCl_3$); 605 ($MH^+$, 100)/6.72 min; 6.13 min; $C_{36}H_{48}N_2O_6$ (604.8) |
| I-100 | E | H | O | 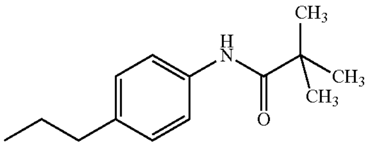 | $-H_2C-CH_2-$ | H | 2.04 (t, H-10) ($CDCl_3$); 537 (M-Boc + $H^+$, 100)/7.84 min; 726 min; $C_{37}H_{52}N_2O_7$ (636.8) |
| I-101 | Z | H | O | 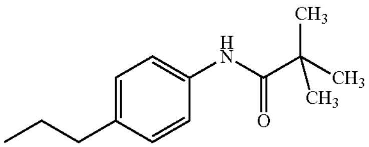 | $-H_2C-CH_2-$ | H | No triplet between 2.0–2.1 ($CDCl_3$): 537 (M-Boc + $H^+$, 100)/7.78 min; 7.21 min; $C_{37}H_{52}N_2O_7$ (636.8) |

TABLE 3-continued
(I)
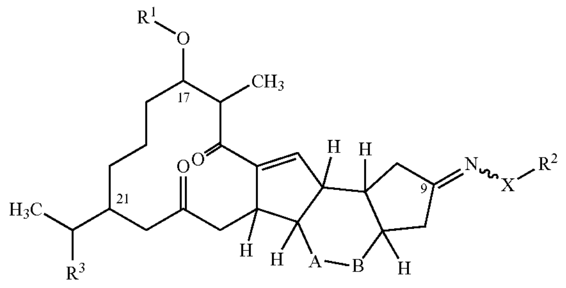
| Ex. No. | Isomer[a] | $R^1$ | X | $R^2$ | A-B | $R^3$ | Physical Data[b] |
|---|---|---|---|---|---|---|---|
| I-102 | E/Z | H | O | 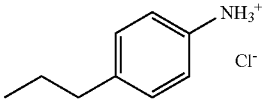 | —$H_2C$—$CH_2$— | H | 537 (M-HCl + $H^+$, 100)/5.02 and 5.11 min; 4.11 and 4.22 min; $C_{32}H_{45}N_2O_5Cl$ (573.2) |
| I-103 | E/Z | H | O | 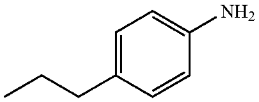 | —$H_2C$—$CH_2$— | H | 537 ($MH^+$, 100)/5.02 and 5.11 min; 4.11 and 4.22 min; $C_{32}H_{44}N_2O_5$ (536.7) |
| I-104 | E/Z | H | O | H | —$H_2C$—$CH_2$— | H | 418($MH^+$, 100)/4.89 and 5.01 min; 4.30 and 4.43 min; $C_{24}H_{35}NO_5$ (417.5) |
| I-105 | E/Z | 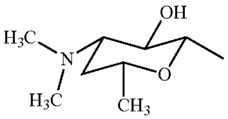 | O | 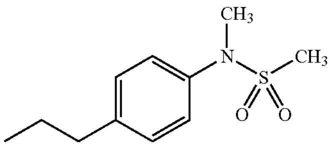 | —$H_2C$—$CH_2$— | H | 786 ($MH^+$, 100)/5.79 min; 5.33 min; $C_{42}H_{63}N_3O_9S$ (786.0) |
| I-106 | E/Z | 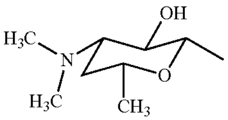 | O | 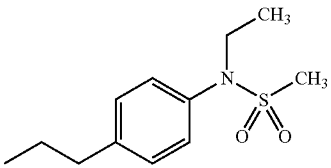 | —$H_2C$—$CH_2$— | H | 800 ($MH^+$, 100)/5.97 min; 5.52 min; $C_{43}H_{65}N_3O_9S$ (800.1) |

TABLE 3-continued
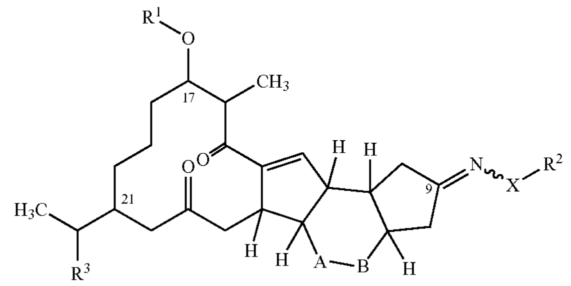
(I)
| Ex. No. | Isomer[a] | $R^1$ | X | $R^2$ | A-B | $R^3$ | Physical Data[b] |
|---|---|---|---|---|---|---|---|
| I-107 | E/Z | 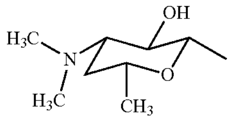 | O | 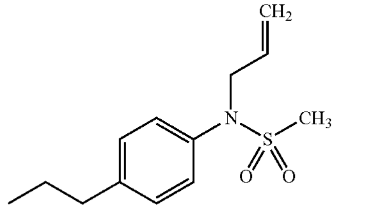 | —$H_2C$—$CH_2$— | H | 812 ($MH^+$, 100)/6.00 min; 5.59 min; $C_{44}H_{65}N_3O_9S$ (812.1) |
| I-108 | E | H | O | 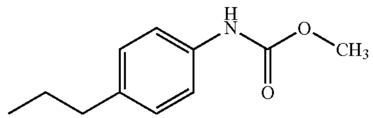 | —$H_2C$—$CH_2$— | H | 2.03 (t, H-10) ($CDCl_3$); 595 ($MH^+$, 100)/6.79 min; 6.28 min; $C_{34}H_{46}N_2O_7$ (594.7) |
| I-109 | Z | H | O | 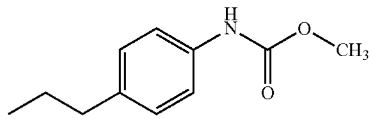 | —$H_2C$—$CH_2$— | H | No triplet between 2.0–2.1 ($CDCl_3$); 595 ($MH^+$, 100)/6.81 min; 6.30 min; $C_{34}H_{46}N_2O_7$ (594.7) |
| I-110 | E | H | O | 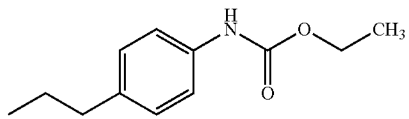 | —$H_2C$—$CH_2$— | H | 2.03 (t, H-10) ($CDCl_3$); 609 ($MH^+$, 100)/7.14 min; 6.64 min; $C_{35}H_{48}N_2O_7$ (608.8) |

TABLE 3-continued
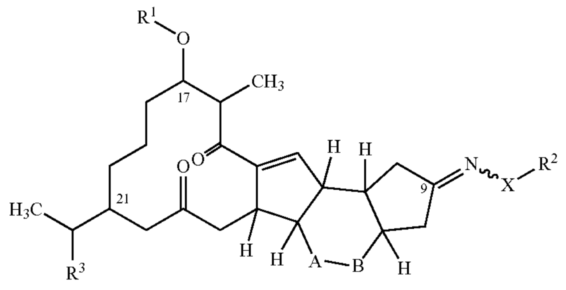
(I)
| Ex. No. | Isomer[a] | $R^1$ | X | $R^2$ | A-B | $R^3$ | Physical Data[b] |
|---|---|---|---|---|---|---|---|
| I-111 | Z | H | O | 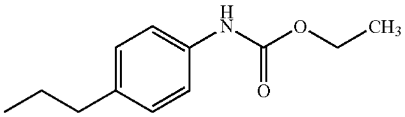 | $-H_2C-CH_2-$ | H | No triplet between 2.0–2.1 ($CDCl_3$); 609 ($MH^+$, 100)/7.13 min; 6.63 min; $C_{35}H_{48}N_2O_7$ (608.8) |
| I-112 | E | H | O | 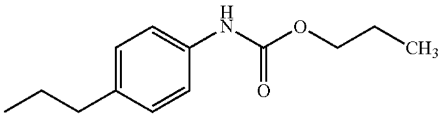 | $-H_2C-CH_2-$ | H | 2.03 (t, H-10) ($CDCl_3$); 623 ($MH^+$, 100)/7.51 min; 7.01 min; $C_{36}H_{50}N_2O_7$ (622.8) |
| I-113 | Z | H | O | 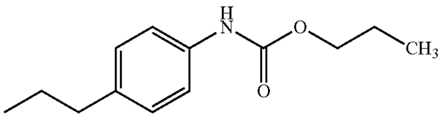 | $-H_2C-CH_2-$ | H | No triplet between 2.0–2.1 ($CDCl_3$); 623 ($MH^+$, 100)/7.49 min; 6.98 min; $C_{36}H_{50}N_2O_7$ (622.8) |
| I-114 | E | H | O | 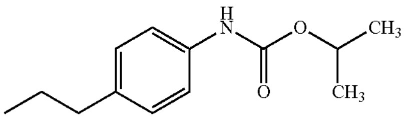 | $-H_2C-CH_2-$ | H | 2.03 (t, H-10) ($CDCl_3$); 623 ($MH^+$, 100)/7.48 min; 6.98 min; $C_{36}H_{50}N_2O_7$ (622.8) |
| I-115 | Z | H | O | 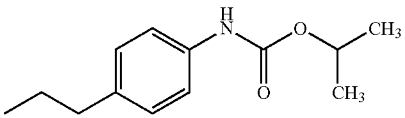 | $-H_2C-CH_2-$ | H | No triplet between 2.0–2.1 ($CDCl_3$); 623 ($MH^+$, 100)/7.45 min; 6.95 min; $C_{36}H_{50}N_2O_7$ (622.8) |

TABLE 3-continued
(I)
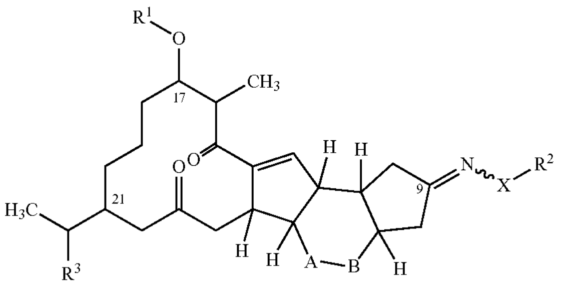
| Ex. No. | Isomer[a] | $R^1$ | X | $R^2$ | A-B | $R^3$ | Physical Data[b] |
|---|---|---|---|---|---|---|---|
| I-116 | E | H | O | 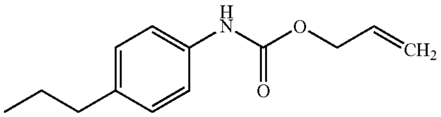 | $—H_2C—CH_2—$ | H | 2.03 (t, H-10) ($CDCl_3$); 621 ($MH^+$, 100)/7.30 min; 6.80 min; $C_{36}H_{48}N_2O_7$ (620.8) |
| I-117 | Z | H | O | 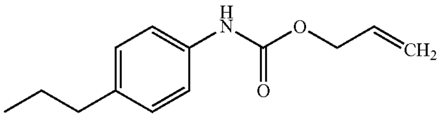 | $—H_2C—CH_2—$ | H | No triplet between 2.0–2.1 ($CDCl_3$); 621 ($MH^+$, 100)/7.31 min; 6.80 min; $C_{36}H_{48}N_2O_7$ (620.8) |
| I-118 | E | H | O | 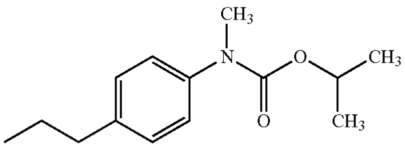 | $—H_2C—CH_2—$ | H | 2.03 (t, H-10) ($CDCl_3$); 637 ($MH^+$, 100)/7.80 min; 7.29 min; $C_{37}H_{52}N_2O_7$ (636.8) |
| I-119 | Z | H | O | 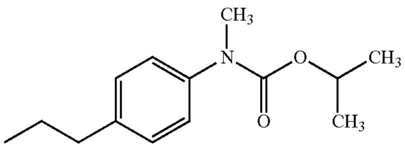 | $—H_2C—CH_2—$ | H | No triplet between 2.0–2.1 ($CDCl_3$); 637 ($MH^+$, 100)/7.75 min; 7.25 min; $C_{37}H_{52}N_2O_7$ (636.8) |

TABLE 3-continued
(I)
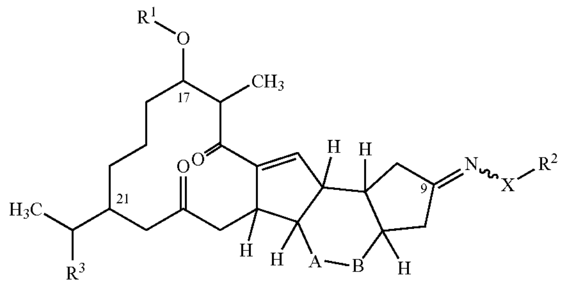
| Ex. No. | Isomer[a] | $R^1$ | X | $R^2$ | A-B | $R^3$ | Physical Data[b] |
|---|---|---|---|---|---|---|---|
| I-120 | E | H | O | 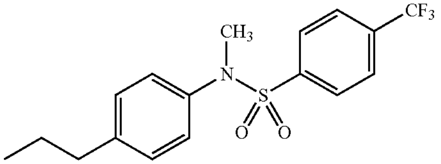 | $-H_2C-CH_2-$ | H | 2.03 (t, H-10) ($CDCl_3$); 759 ($MH^+$, 100)/8.20 min; 7.69 min; $C_{40}H_{49}F_3N_2O_2S$ (758.9) |
| I-121 | Z | H | O | 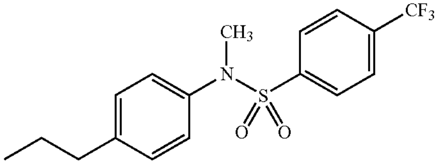 | $-H_2C-CH_2-$ | H | No triplet between 2.0–2.1 ($CDCl_3$); 759 ($MH^+$, 100)/8.21 min; 7.70 min; $C_{40}H_{49}F_3N_2O_7S$ (758.9) |
| I-122 | E | H | O | 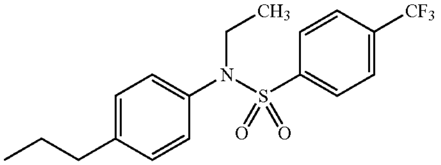 | $-H_2C-CH_2-$ | H | 2.03 (t, H-10) ($CDCl_3$); 773 ($MH^+$, 100)/8.36 min; 7.89 min; $C_{41}H_{51}F_3N_2O_7S$ (772.9) |
| I-123 | Z | H | O | 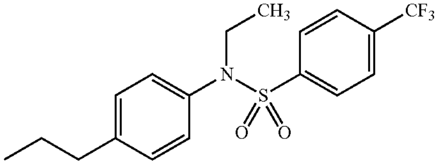 | $-H_2C-CH_2-$ | H | No triplet between 2.0–2.1 ($CDCl_3$); 773 ($MH^+$, 100)/8.39 min; 7.88 min; $C_{41}H_{51}F_3N_2O_2S$ (772.9) |

TABLE 3-continued
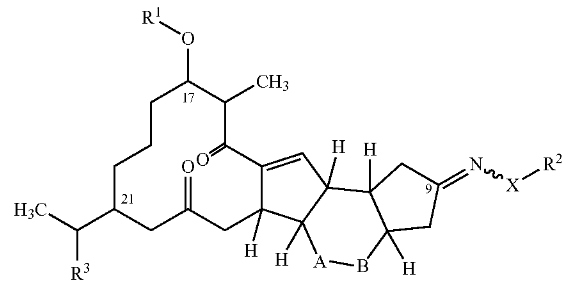
(I)
| Ex. No. | Isomer[a] | $R^1$ | X | $R^2$ | A-B | $R^3$ | Physical Data[b] |
|---|---|---|---|---|---|---|---|
| I-124 | E | H | O | 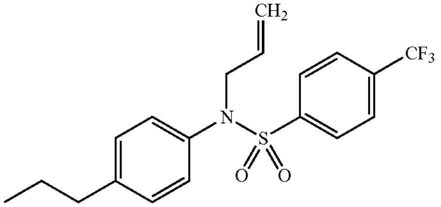 | $—H_2C—CH_2—$ | H | 2.03 (t, H-10) ($CDCl_3$);<br>785 ($MH^+$, 100)/8.39 min; 7.88 min;<br>$C_{42}H_{51}F_3N_2O_7S$ (784.9) |
| I-125 | Z | H | O | 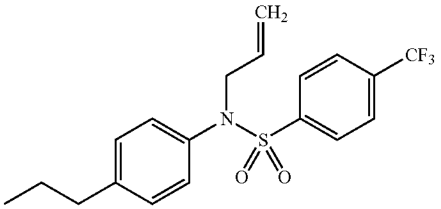 | $—H_2C—CH_2—$ | H | No triplet between 2.0–2.1 ($CDCl_3$);<br>785 ($MH^+$, 100)/8.40 min; 7.89 min;<br>$C_{42}H_{51}F_3N_2O_2S$ (784.9) |
| I-126 | E | H | O | 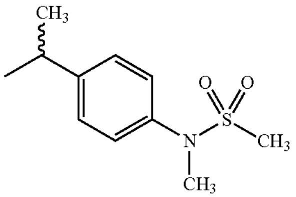 | $—H_2C—CH_2—$ | H | 629 ($MH^+$, 100)/6.99 and 7.06 min 6.48 and 6.55 min;<br>$C_{34}H_{48}N_2O_7S$ (628.8) |

TABLE 3-continued
(I)
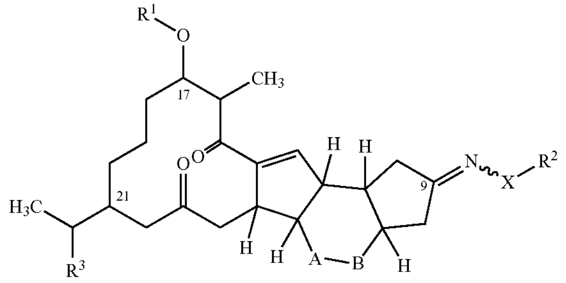
| Ex. No. | Isomer[a] | R1 | X | R2 | A-B | R3 | Physical Data[b] |
|---|---|---|---|---|---|---|---|
| I-127 | Z | H | O | 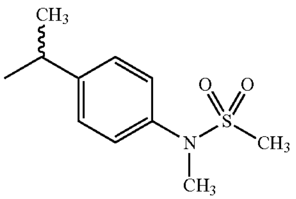 | —$H_2C$—$CH_2$— | H | 629 ($MH^+$, 100)/6.76 and 6.87 min; 6.25 and 6.36 min; $C_{34}H_{48}N_2O_7S$ (628.8) |
| I-128 | E | H | O | 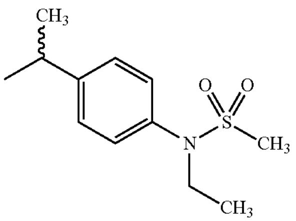 | —$H_2C$—$CH_2$— | H | 643 ($MH^+$, 100)/7.22 min; 6.71 and 6.75 min; $C_{35}H_{50}N_2O_7S$ (642.9) |
| I-129 | Z | H | O | 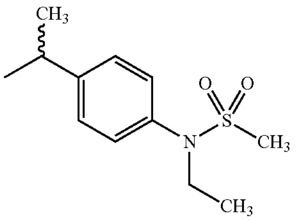 | —$H_2C$—$CH_2$— | H | 643 ($MH^+$, 100)/6.98 and 7.07 min; 6.48 and 6.57 min; $C_{35}H_{50}N_2O_2S$ (642.9) |

TABLE 3-continued
(I)
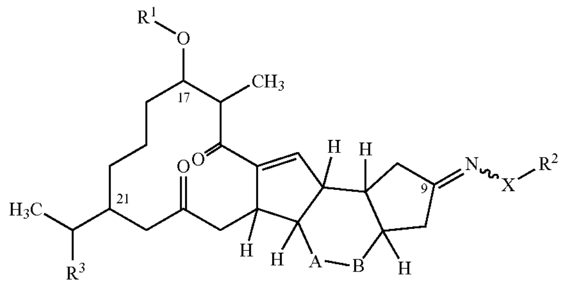
| Ex. No. | Isomer[a] | $R^1$ | X | $R^2$ | A-B | $R^3$ | Physical Data[b] |
|---|---|---|---|---|---|---|---|
| I-130 | E | H | O | 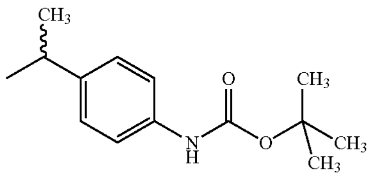 | $—H_2C—CH_2—$ | H | 637 ($MH^+$, 100)/8.05 and 8.10 min; 7.54 and 7.59 min; $C_{37}H_{52}N_2O_7$ (636.8) |
| I-131 | Z | H | O | 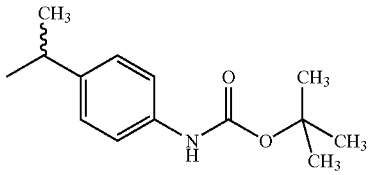 | $—H_2C—CH_2—$ | H | 637 ($MH^+$, 100)/7.79 and 7.86 min; 7.30 and 7.37 min; $C_{37}H_{52}N_2O_7$ (636.8) |
| I-132 | E | H | O | 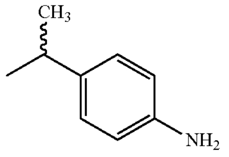 | $—H_2C—CH_2—$ | H | 537 ($MH^+$, 100)/5.76 and 5.88 min; 4.63 and 4.74 min; $C_{32}H_{44}N_2O_5$ (536.7) |
| I-133 | Z | H | O | 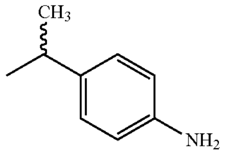 | $—H_2C—CH_2—$ | H | 537 ($MH^+$, 100)/5.54 and 5.70 min; 4.41 and 4.56 min; $C_{32}H_{44}N_2O_5$ (536.7) |

TABLE 3-continued
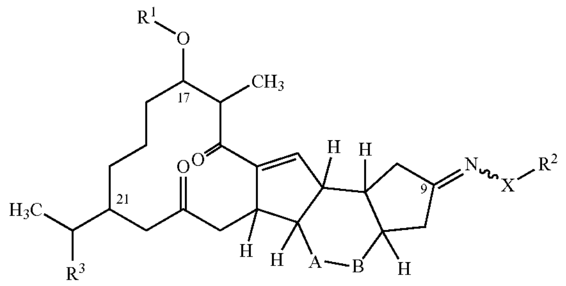
(I)
| Ex. No. | Isomer[a] | R1 | X | R2 | A-B | R3 | Physical Data[b] |
|---|---|---|---|---|---|---|---|
| I-134 | Z | H | O | 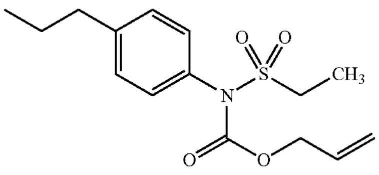 | —HC═CH— | H | 711 ($MH^+$, 100)/9.90 min; $C_{35}H_{50}N_2O_9S$ (710.8) |
| I-135 | E | H | O | 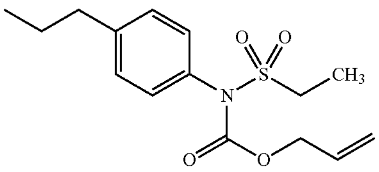 | —HC═CH— | H | 711 ($MH^+$, 100)/9.74 min; $C_{35}H_{50}N_2O_9S$ (710.8) |
| I-136 | E | H | O | 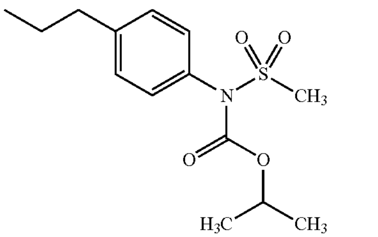 | —HC═CH— | H | 699 ($MH^+$, 100)/9.71 min; $C_{37}H_{50}N_2O_9S$ (698.8) |

TABLE 3-continued
(I)
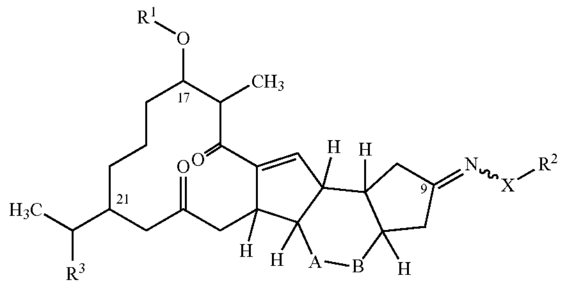
| Ex. No. | Isomer[a] | R1 | X | R2 | A-B | R3 | Physical Data[b] |
|---|---|---|---|---|---|---|---|
| I-137 | Z | H | O | 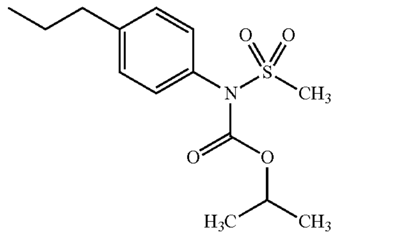 | —HC═CH— | H | 699 ($MH^+$, 100)/9.82 min; $C_{37}H_{50}N_2O_9S$ (698.8) |
| I-138 | E | H | O | 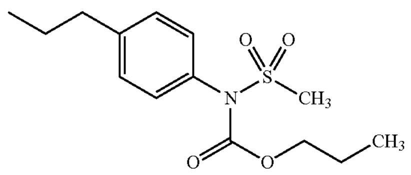 | —HC═CH— | H | 699 ($MH^+$, 100)/9.75 min; $C_{37}H_{50}N_2O_9S$ (698.8) |
| I-139 | Z | H | O | 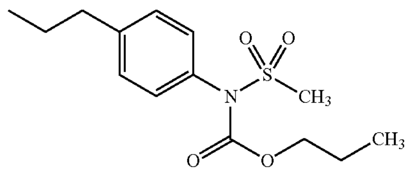 | —HC═CH— | H | 699 ($MH^+$, 100)/9.87 min; $C_{37}H_{50}N_2O_9S$ (698.8) |

TABLE 3-continued
(I)
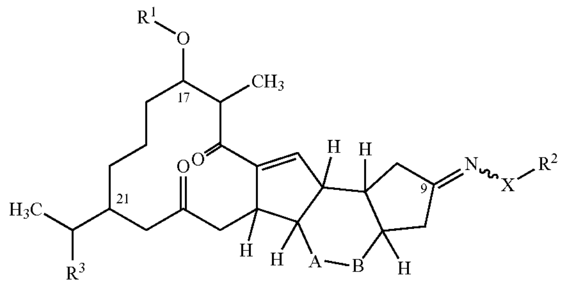
| Ex. No. | Isomer[a] | R1 | X | R2 | A-B | R3 | Physical Data[b] |
|---|---|---|---|---|---|---|---|
| I-140 | E | H | O | 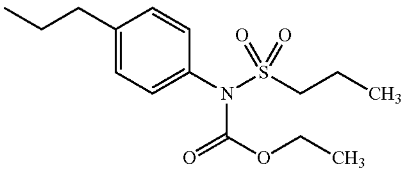 | —HC═CH— | H | 713 (MH+, 100)/10.01 min; $C_{38}H_{52}N_2O_9S$ (712.9) |
| I-141 | Z | H | O | 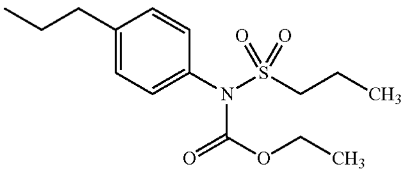 | —HC═CH— | H | 713 (MH+, 100)/10.11 min; $C_{38}H_{52}N_2O_9S$ (712.9) |
| I-142 | E | H | O | 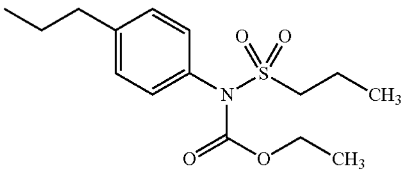 | —HC═CH— | H | 727 (MH+, 100)/10.34 min; $C_{39}H_{54}N_2O_9S$ (726.9) |

TABLE 3-continued
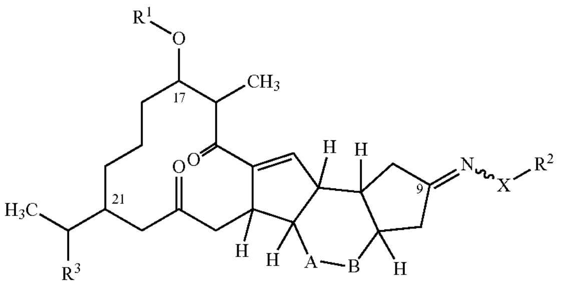
(I)
| Ex. No. | Isomer[a] | R1 | X | R2 | A-B | R3 | Physical Data[b] |
|---|---|---|---|---|---|---|---|
| I-143 | Z | H | O | 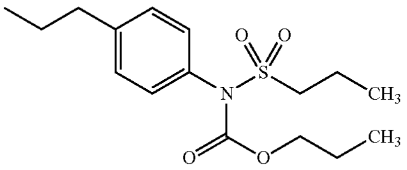 | —HC═CH— | H | 727 (MH+, 100)/10.42 min; $C_{39}H_{54}N_2O_9S$ (726.9) |
| I-144 | E | H | O | 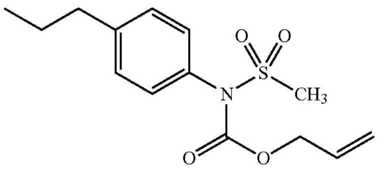 | —HC═CH— | H | 697 (MH+, 100)/9.48 min; $C_{37}H_{48}N_2O_9S$ (696.8) |
| I-145 | Z | H | O | 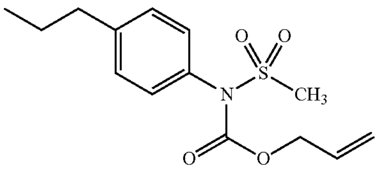 | —HC═CH— | H | 697 (MH+, 100)/9.67 min; $C_{37}H_{48}N_2O_9S$ (696.8) |
| I-146 | Z | H | O | 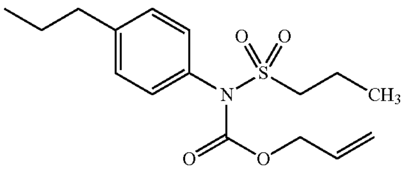 | —HC═CH— | H | 725 (MH+, 100)/10.24 min; $C_{39}H_{52}N_2O_9S$ (724.9) |

TABLE 3-continued
(I)
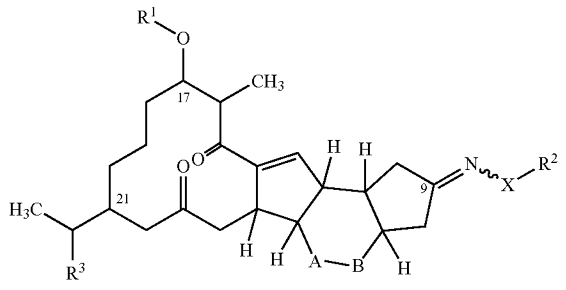
| Ex. No. | Isomer[a] | $R^1$ | X | $R^2$ | A-B | $R^3$ | Physical Data[b] |
|---|---|---|---|---|---|---|---|
| I-147 | E | H | O | 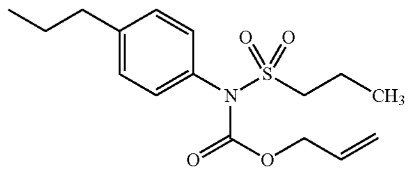 | —HC═CH— | H | 725 ($MH^+$, 100)/10.15 min; $C_{39}H_{52}N_2O_9S$ (724.9) |
| I-148 | E | H | O | 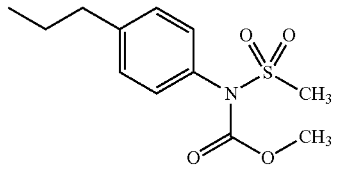 | —HC═CH— | H | 671 ($MH^+$, 100)/9.02 min; $C_{35}H_{46}N_2O_9S$ (670.8) |
| I-149 | Z | H | O | 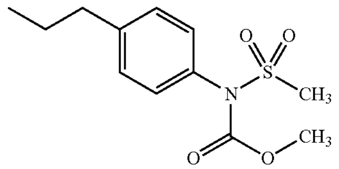 | —HC═CH— | H | 671 ($MH^+$, 100)/9.17 min; $C_{35}H_{46}N_2O_9S$ (670.8) |

TABLE 3-continued
(I)
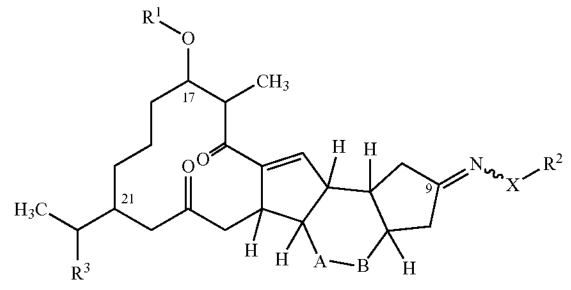
| Ex. No. | Isomer[a] | $R^1$ | X | $R^2$ | A-B | $R^3$ | Physical Data[b] |
|---|---|---|---|---|---|---|---|
| I-150 | E | H | O | 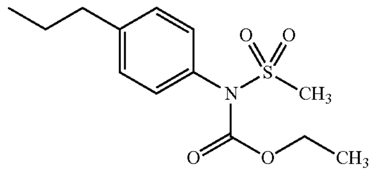 | —HC═CH— | H | 685 ($MH^+$, 100)/9.34 min; $C_{36}H_{48}N_2O_9S$ (684.8) |
| I-151 | Z | H | O | 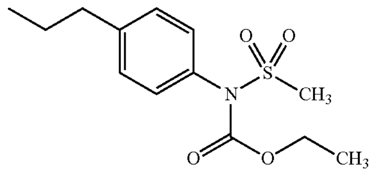 | —HC═CH— | H | 685 ($MH^+$, 100)/9.43 min; $C_{36}H_{48}N_2O_9S$ (684.8) |
| I-152 | E | H | O | 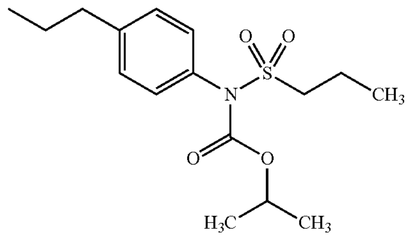 | —HC═CH— | H | 727 ($MH^+$, 100)/10.36 min; $C_{39}H_{54}N_2O_9S$ (726.9) |

TABLE 3-continued
(I)
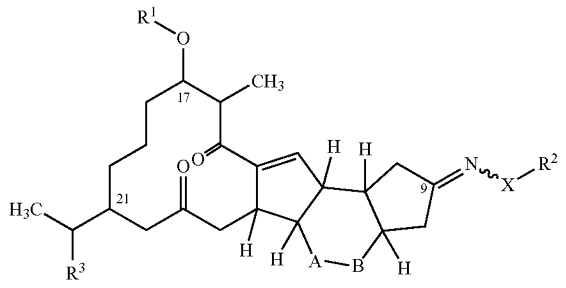
| Ex. No. | Isomer[a] | R1 | X | R2 | A-B | R3 | Physical Data[b] |
|---|---|---|---|---|---|---|---|
| I-153 | Z | H | O | 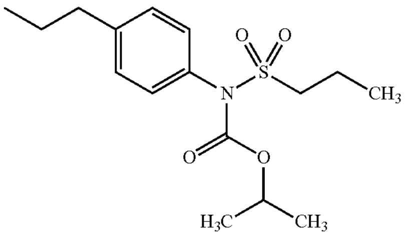 | —HC═CH— | H | 727 ($MH^+$, 100)/10.44 min; $C_{39}H_{54}N_2O_9S$ (726.9) |
| I-154 | E | H | O | 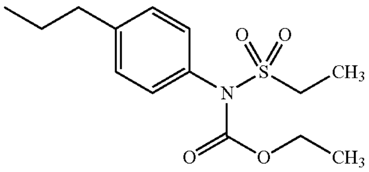 | —HC═CH— | H | 699 ($MH^+$, 100)/9.64 min; $C_{37}H_{50}N_2O_9S$ (698.8) |
| I-155 | Z | H | O | 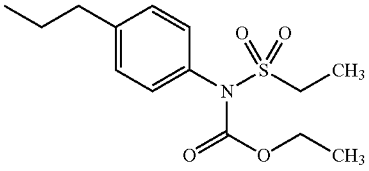 | —HC═CH— | H | 699 ($MH^+$, 100)/9.75 min; $C_{37}H_{50}N_2O_9S$ (698.8) |

TABLE 3-continued
(I)
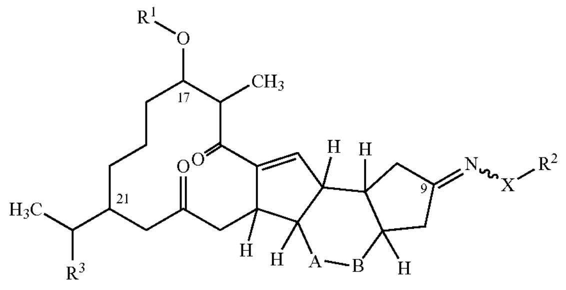
| Ex. No. | Isomer[a] | $R^1$ | X | $R^2$ | A-B | $R^3$ | Physical Data[b] |
|---|---|---|---|---|---|---|---|
| I-156 | E | H | O | 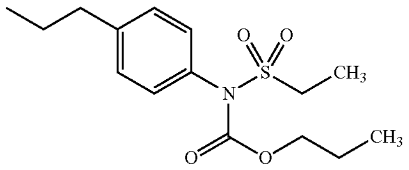 | —HC═CH— | H | 713 ($MH^+$, 100)/10.03 min; $C_{38}H_{52}N_2O_9S$ (712.9) |
| I-157 | Z | H | O | 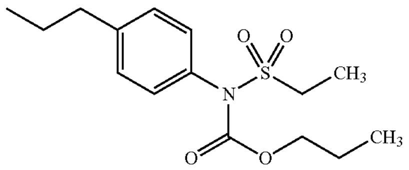 | —HC═CH— | H | 713 ($MH^+$, 100)/10.13 min; $C_{38}H_{52}N_2O_9S$ (712.9) |
| I-158 | E | H | O | 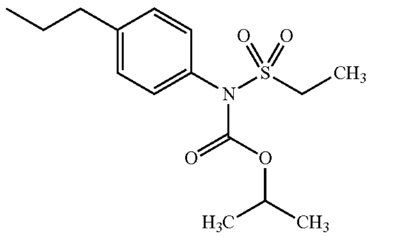 | —HC═CH— | H | 713 ($MH^+$, 100)/9.98 min; $C_{38}H_{52}N_2O_9S$ (712.9) |

TABLE 3-continued
(I)
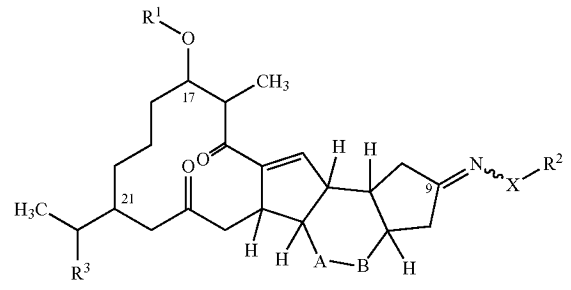
| Ex. No. | Isomer[a] | $R^1$ | X | $R^2$ | A-B | $R^3$ | Physical Data[b] |
|---|---|---|---|---|---|---|---|
| I-159 | Z | H | O | 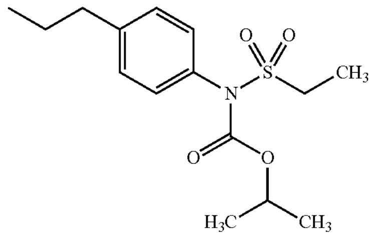 | —HC═CH— | H | 713 ($MH^+$, 100)/10.09 min; $C_{38}H_{52}N_2O_9S$ (712.9) |
| I-160 | E | H | O | 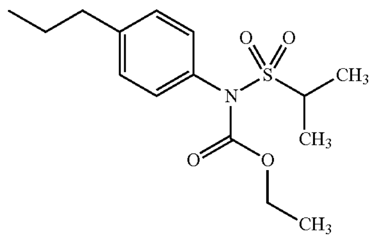 | —HC═CH— | H | 713 ($MH^+$, 100)/9.93 min; $C_{38}H_{52}N_2O_9S$ (712.9) |

TABLE 3-continued
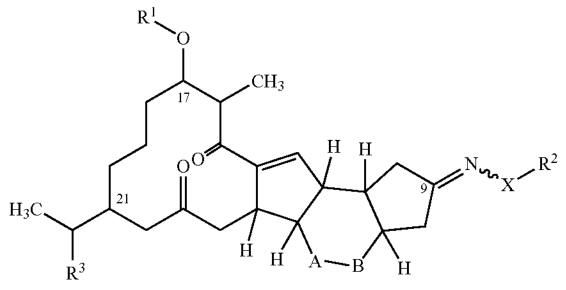
(I)
| Ex. No. | Isomer[a] | R[1] | X | R[2] | A-B | R[3] | Physical Data[b] |
|---|---|---|---|---|---|---|---|
| I-161 | Z | H | O | 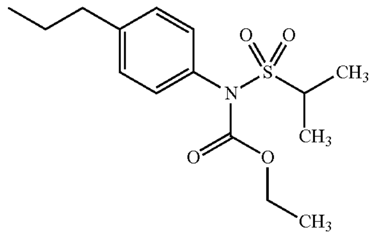 | —HC═CH— | H | 713 (MH$^+$, 100)/10.03 min; $C_{38}H_{52}N_2O_9S$ (712.9) |
| I-162 | E | H | O | 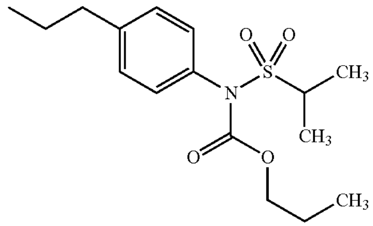 | —HC═CH— | H | 727 (MH$^+$, 100)/10.31 min; $C_{39}H_{54}N_2O_9S$ (726.9) |
| I-163 | E | H | O | 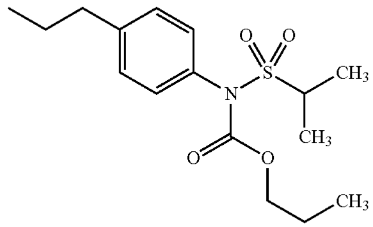 | —HC═CH— | H | 727 (MH$^+$, 100)/10.38 min; $C_{39}H_{54}N_2O_9S$ (726.9) |

TABLE 3-continued
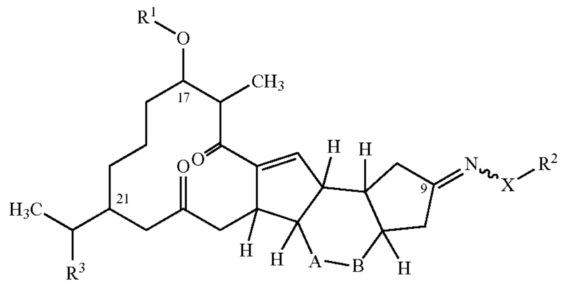
(I)
| Ex. No. | Isomer[a] | $R^1$ | X | $R^2$ | A-B | $R^3$ | Physical Data[b] |
|---|---|---|---|---|---|---|---|
| I-164 | E | H | O | 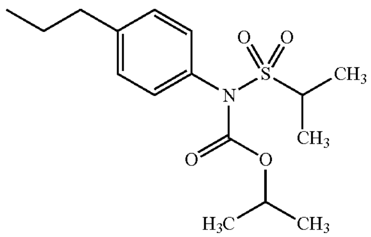 | —HC═CH— | H | 727 ($MH^+$, 100)/10.27 min; $C_{39}H_{54}N_2O_9S$ (726.9) |
| I-165 | Z | H | O | 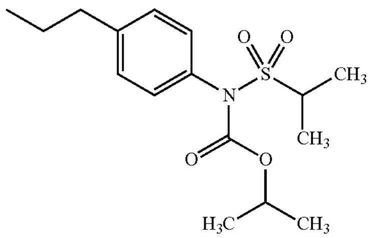 | —HC═CH— | H | 727 ($MH^+$, 100)/10.33 min; $C_{39}H_{54}N_2O_9S$ (726.9) |
| I-166 | E/Z | H | NH | 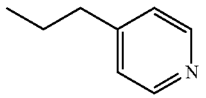 | —HC═CH— | H | 520 ($MH^+$)/5.14 min; 5.23 min $C_{31}H_{41}N_3O_4$ (519.6) |

TABLE 3-continued (I)

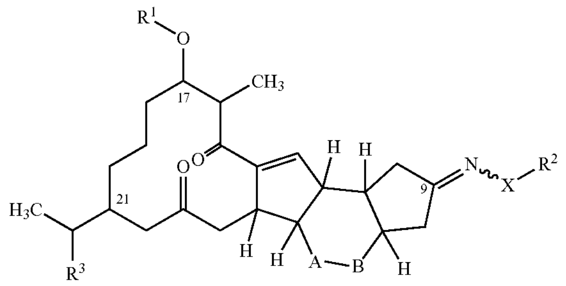

| Ex. No. | Isomer[a] | $R^1$ | X | $R^2$ | A-B | $R^3$ | Physical Data[b] |
|---|---|---|---|---|---|---|---|
| I-167 | E/Z | H | NH | 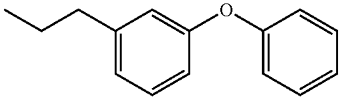 | —HC═CH— | H | 597 ($MH^+$)/10.77 min; 11.12 min $C_{37}H_{44}N_2O_5$ (596.7) |
| I-168 | E/Z | H | NZ | 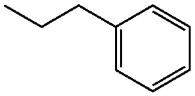 | —HC═CH— | H | 653 ($MH^+$)/10.26 min; 10.57 min $C_{40}H_{48}N_2O_6$ (652.8) |

Z = —CO—O—$CH_2$-Phenyl
[a]Z-isomer (syn); E-isomer (anti).
[b]2D-NMR: $^1H/^{13}C$ Correlation (HMQC)(600 MHz/150 MHz, δ, ppm); LC-MS (acidic) m/z (%)/$R_f$ (min); HPLC (Chromasil C18, 3.5 μm; pH 2.3) 0.1% $H_3PO_4$ - Acetonitrile /$R_t$ (min); $^1H$-NMR (400 MHz, δ, ppm): characteristic triplet of H-10 between 2.0.and 2.1 ppm for the E-isomer.

Initial Substances According to Formula (II)

Example (II-1)

9-keto spinosyn A-aglycone

The 9-keto spinosyn A-aglycone (IIa) [compound according to the general formula (II), where $R^1$ stands for hydrogen and A-B stands for the group —HC═CH—], can be produced as described in WO 02/079184 by way of pyridiniumdichromate oxidation from the spinosyn A-aglycone (see WO 01/16303).

46.55 g (115.6 mmol) spinosyn A-aglycone (II-1) was dissolved in an inert gas atmosphere 1100 ml abs. dichloromethane and mixed with 43.51 g (115.6 mmol) pyridiniumdichromate (PDC). After stirring for 4 hours at 25° C. and adding 900 ml diethyl ether, the precipitated chromium salts are siphoned off, and the filtrate is concentrated in vacuum. Column chromatography on silica gel follows (silica gel 60-Merck, grain size: 0.04 to 0.063 mm), first with cyclohexane/acetic acid ethyl ester (1:1) as mobile phases, then 100% acetic ethyl ester. The reaction yields 3.68 g 9,17-diketo-spinosyn-aglycone and 23.40 g of an approximate 9:1 mixture of spinosyn A-aglycone and 17-keto-spinosyn-aglycone (II-1) in addition to 11.74 g of recovered spinosyn A-aglycone. By crystallising the mixture in cyclohexane/acetic acid ethyl ester, the 9-keto spinosyn A-aglycone (II-1) is enriched to >98%. The reaction yields 20.78 g 9-keto spinosyn A-aglycone (II-1) as colourless crystal.

DC: $R_f$ ($SiO_2$, acetic acid ethyl ester)=0.44

$^1$H-NMR ($CDCl_3$, δ)=6.77 (s, 13-H); 5.97 (d, 6-H); 5.88 (m, 5-H); 4.72 (m, 21-H); 3.69 (m, 17-H) (among others)—LC/ESI-MS: m/z (%)=401 (25%) $[M]^+$, 289 (100). $^{13}$C-NMR (600 MHz, $CDCl_3$, δ)=9.3, 15.7 (2×$CH_3$); 21.5, 28.3, 30.0, 33.9, 34.8, 43.1, 43.8 (7×$CH_2$); 40.6, 41.1, 44.3, 47.7, 48.1, 49.2 (6×CH); 72.5 (CH—OH); 77.0 (CH); 128.1, 129.3 (—HC═CH—); 144.9, 146.1 (—HC═C—); 172.6 (—O—C═O); 202.6, 216.1 (2×C═O) ppm.

9,17-diketo spinosyn-A aglycone: DC: $R_f$ ($SiO_2$, acetic acid ethyl ester)=0.64.

$^1$H-NMR: $CDCl_3$, δ=6.92 (s, 13-H); 5.97 (d, 6-H); 5.87 (m, 5-H); 4.85 (m, 21-H); 4.25 (q, 16-H) (among others)—LC/ESI-MS: m/z (%)=399 ($MH^+$, 100).

Example (II-2)

5,6-dihydro-9-keto spinosyn A-aglycone

The 5,6-dihydro-9-keto spinosyn A-aglycone (IIa) [compound according to the general formula (II), where $R^1$ stands for hydrogen and A-B stands for the group —$H_2C$—$CH_2$—], can be produced in a similar manner to the method described in WO 02/079184 by way of a pyridiniumdichromate oxidation process from 5,6-dihydro-spinosyn A-aglycone (see WO 01/16303).

202 mg (0.5 mmol) 5,6-dihydro-spinosyn A-aglycone is dissolved in an inert gas atmosphere in 5 ml absolute dichloromethane and mixed with 188 mg (0.5 mmol) PDC. After stirring for 4 hours at 25° C. and adding 5 ml diethyl ether, the precipitated chromium salts are siphoned off, and the filtrate is concentrated in vacuum. Column chromatography on silica gel follows (silica gel 60-Merck, grain size: 0.04 to 0.063 mm), first with cyclohexane/acetic acid ethyl ester (1:1) as mobile phases, then 100% acetic ethyl ester. The reaction yields 24 mg 5,6-dihydro-9,17-diketo spinosyn-aglycone and 103 mg 5,6-dihydro-17-keto spinosyn-aglycone (II-1) in addition to 41 mg of recovered 5,6-dihydro-spinosyn A-aglycone.

DC: $R_f$ ($SiO_2$, acetic acid ethyl ester)=0.44

$^1$H-NMR ($CDCl_3$,δ)=6.83 (s, 13-H); 4.68 (m, 21-H); 3.69 (m, 17-H) (among others)—LC/ESI-MS: m/z (%)=403 ($MH^+$, 23), 291 (100).

5,6-dihydro-9,17-diketo spinosyn A-aglycone

DC: $R_f$($SiO_2$, acetic acid ethyl ester)=0.64.

$^1$H-NMR ($CDCl_3$, δ)=6.99 (s, 13-H); 4.82 (m, 21-H); 4.23 (q, 16-H) (among others)—LC/ESI-MS: m/z (%)=423 ($M+Na^+$, 100).

Example (II-3)

17-β-D-forosaminyl-9-keto spinosyn A 9-pseudoaglycone

The 17-β-D-forosaminyl-9-keto spinosyn A 9-pseudoaglycone (II-2) [compound according to formula (II), where $R^1$ stands for D-forosaminyl, $R^3$ stands for hydrogen and A-B stands for the group —HC═CH—] can be synthesised from 9-keto spinosyn A-aglycone (II-1) in two reaction steps:

a) Synthesis of trichloroacetimidate (also see Methode (Methods) by G. R. Duffin et al. (2000), J. Chem. Soc., Perkin Trans. 1: 2237-2242 and WO 02/079184).
b) Glycosidation of 9-keto spinosyn A-aglycone with trichloroacetimidate (also see Methode (Methods) by G. R. Duffin et al. (2000), J. Chem. Soc., Perkin Trans. 1: 2237-2242 and WO 02/079184).

Example (II-4)

17-β-D-desosaminyl-9-keto spinosyn A 9-pseudoaglycone

The 17-β-D-desosaminyl-9-keto spinosyn A 9-pseudoaglycone (II-2) [compound according to formula (II), where $R^1$stands for D-desosaminyl, $R^3$ stands for hydrogen and A-B stands for the group —HC═CH—] can be synthesised from 9-keto spinosyn A-aglycone (II-1) in two reaction steps:

a) Glycosidation: 2.0 g of molecular sieve 4A is first mixed with 2.7 g (7.34 mMol) bis(cyclopentadienyl)hafnium-dichloride, then with 1.5 g (7.31 mMol) silver perchlorate, then with 1.17 g (2.92 mMol) 9-keto spinosyn-aglycone (II-1) and finally with 41 ml absolute methylenechloride at room temperature in an inert gas atmosphere. After cooling to −20° C., 0.34 g (1.46 mMol) 1-fluoro-2-O-methoxycarbonyl-D-desosamine (see K. Suzuki et al., Tetrahedron Lett. 29 (29), 3571-3574, 1988) dissolved in 10.0 ml absolute methylenechloride, is added. After stirring for two hours at 0-5° C., the reaction preparation is mixed with saturated sodium hydrogen carbonate solution, filtered over Celite and concentrated in vacuum. The remaining raw product is chromatographed over a silica gel column (silica gel 60-Merck, grain size: 0.04 to 0.063 mm) using cyclohexane/acetone (2:1) as mobile phases. The reaction yields 927 mg (51.4% of the theoretical yield) 2-O-methoxycarbonyl-17-β-D-desosaminyl-9-keto spinosyn A 9-pseudoaglycone, of which O can be subsequently deblocked.
   $C_{34}H_{49}NO_9$ (615.7); LC-MS m/z (%)=616 ($MH^+$, 100).
b) O-Deblocking reaction: 203 mg (0.33 mMol) 2-O-methoxycarbonyl-17-β-D-desosaminyl-9-keto spinosyn A 9-pseudoaglycone is mixed with a mixture of 15 ml methanol, 1.5 ml triethylamine and 1.5 ml water, and it is stirred for 48 hours at room temperature. After concentrating in vacuum, it yields 180 mg (97.7% of the theoretical yield) 17-β-D-desosaminyl-9-keto spinosyn A 9-pseudoaglycone, which can be utilised for additional reactions.

$C_{32}H_{47}NO_7$ (557.7); LC-MS m/z (%)=558 ($MH^+$, 100); $R_t$=4.96 min.

Example (II-5)

17-β-D-O-acetyl-desosaminyl-9-keto spinosyn A 9-pseudoaglycone 200.0 mg (0.36 mmol) 17-β-D-desosaminyl-9-keto spinosyn A 9-pseudoaglycone (II-2) is stirred with 25 ml dichloromethane and is first mixed with 87.8 mg (102.09 mmol) acetic acid anhydride, then 94.3 mg ((0.93 mmol) triethylamine and finally 43.8 mg (0.36 mmol) 4-N,N-dimethylamino-pyridine (DMAP). After stirring for 18 hours at room temperature, the entire reaction preparation is concentrated in vacuum and chromatographed over a silica gel column (silica gel 60-Merck, grain size: 0.04 to 0.063 mm) with dichloromethane/methanol (15:1) as mobile phases. This, yields 148.1 mg (68.8% of the theoretical yield) 17-β-D-O-acetyl-desosaminyl-9-keto spinosyn A 9-pseudoaglycone, which can subsequently be used for additional reactions.

$C_{34}H_{49}NO_8$ (599.7); LC-MS m/z (%)=600 ($MH^+$, 100); $R_t$=5.13 min.

$^{13}$C-NMR (DMF-$d_7$): δ=21.3 ($CH_3$); 71.9 (—CH—O—); 170.1 (—O—C═O) ppm.

Example (III-1)

Preparation of 4-(N'-isopropyloxycarbonyl-N'-methylsulphonylamino-phenethoxy)-amine a) 2-(4-tert-butyloxycarbonylamino-phenyl)-ethanol:

24.7 g (180 mmol) 2-(4-aminophenyl)-ethanol is stirred in 200 ml tetrahydrofuran, and a solution of 49.1 g (225 mmol) di-tert-butyldicarbonate in 50 ml tetrahydrofuran is added one drop at a time at 0° C. over an hour. After two hours, 75% of the reaction has already taken place (HPLC verification). In order to complete the reaction, 0.1 equivalents of di-tert-butyldicarbonate is added once again after four hours, and this is stirred for approx. 18 hours at room temperature. Afterward, additional 0.1 equivalents of di-tert-butyldicarbonate are added, and this mixture is stirred until completion of the reaction at room temperature (total reaction time: 26.5 hours). The reaction preparation is concentrated in vacuum, the remaining colourless solid substance (43.2 g) is levigated in 300 ml n-hexane and stirred for approx. 18 hours at room temperature. Thereafter, the solid substance is separated, washed with 300 ml n-hexane and dried in a high vacuum. The reaction yields 41.7 g (97.6% of the theoretical yield) 2-(4-tert-butyloxycarbonylamino-phenyl)-ethanol, which can be used for the following reaction.

b) N-(4-amino-phenethoxy)-phthalimide hydrochloride:

1.7 g (7.25 mmol) 2-(4-tert-butyloxycarbonylamino-phenyl)-ethanol, 1.3 g (7.97 mmol) N-hydroxy-phthalimide and 2.1 g (7.97 mmol) triphenylphosphine are mixed in 45 ml tetrahydrofuran, and 1.5 g (8.7 mmol) diethylazodicarboxylate (DEAD) is added one drop at a time to the mixture at 0° C. Subsequently, the reaction mixture is stirred for another ten hours at 25° C. The solvent is then siphoned off in vacuum, the remaining residue is absorbed in chloroform, and the organic phase is washed four times with sodium hydrogen carbonate solution and water. The organic phase is separated and dried over sodium sulphate. After siphoning off the solvent, raw N-(4-tert-butyloxycarbonylamino-phenethoxy)-phthalimide remains, which is not purified further. In order to separate the protective group (Boc), the raw product is dissolved in 7 ml dioxane, mixed with a total of seven equivalents of 4N hydrochloric acid in dioxane a little at a time (HPLC verification), and the mixture is stirred for approximately 18 hours at room temperature. Thereafter, the precipitated solid substance is separated, washed with dioxane and dried in the high vacuum. The reaction yields 2.3 g (100% of the theoretical yield) N-(4-amino-phenethoxy)-phthalimide hydrochloride, which can be employed in the following reaction.

c) N-[4-(N'-methylsulphonylamino-phenethoxy)]-phthalimide:

24.0 g (60.2 mmol) N-(4-amino-phenethoxy)-phthalimide hydrochloride is prepared in 400 ml dichloromethane and mixed with 14.6 ml pyridine. After dripping 6.9 g (60.2 mmol) methanesulphonylchloride into the mixture at 0° C., the reaction preparation is stirred for approximately 18 hours at room temperature. The reaction solution is then shaken once with 5% aqueous hydrochloric acid solution and twice with distilled water. The organic phase is separated, dried and concentrated in vacuum. The remaining residue is mixed in hot ethanol, and the solution is filtered after cooling. After concentrating the filtrate, the remaining solid substance is re-crystallised from chloroform/cyclohexane. The reaction yields 8.6 g (39.6% of the theoretical yield) crystalline N-[4-(N'-methylsulphonylamino-phenethoxy)]-phthalimide. Another 2.7 g N-[4-(N'-methylsulphonylamino-phenethoxy)]-phthalimide can be obtained from the filter residue.

$C_{17}H_{16}N_2O_5S$ (360.3); LC-MS m/z (%)=361 ($MH^+$, 100); $R_t$=6.59 min.

d) N-[4-(N'-isopropyloxycarbonyl-N'-methylsulphonylamino-phenethoxy)]-phthalimide:

2.0 g (5.55 mmol) N-[4-(N'-methylsulphonylamino-phenethoxy)]-phthalimide is stirred in 75 ml absolute pyridine and mixed with 2.7 g (22.2 mmol) chloroformic acid isopropyl ester at 0° C. in a protective gas atmosphere (argon). After stirring for an hour at room temperature, the entire reaction preparation is concentrated in vacuum. The remaining residue is absorbed in acetic acid ethyl ester and shaken once with 5% aqueous hydrochloric acid. Afterward, the organic phase is shaken twice with water, separated and concentrated in vacuum. The remaining residue is chromatographed over a silica gel column (silica gel 60-Merck, grain size: 0.04 to 0.063 mm) using cyclohexane/acetone (2:1) as mobile phases. The reaction yields 2.4 g (99.2% of the theoretical yield) N-[4-(N'-isopropyloxycarbonyl-N'-methylsulphonylamino-phenethoxy)]-phthalimide.

$C_{21}H_{22}N_2O_7S$ (446.4); LC-MS m/z (%)=447 ($MH^+$); $R_t$=8.00 min.

e) 4-(N'-isopropyloxycarbonyl-N'-methylsulphonylamino-phenethoxy)-amine:

2.3 g (5.55 mmol) N-[4-(N'-isopropyloxycarbonyl-N'-methylsulphonylamino-phenethoxy)]-phthalimide is stirred in 20 ml dichloromethane and mixed with 1.0 ml methanol and 0.52 g (10.44 mmol) hydrazine hydrate at room temperature. The reaction mixture is stirred for 18 hours at room temperature. Afterward, the entire reaction preparation is filtered, and the filtrate is shaken once with 5N ammonia solution. The organic phase is separated, dried and concentrated in vacuum. The reaction yields 1.1 g (64.8% of the theoretical yield) 4-(N'-isopropyloxycarbonyl-N'-methylsulphonylamino-phenethoxy)-amine.

$C_{13}H_{20}N_2O_5S$ (316.3); LC-MS m/z (%)=317 ($MH^+$, 25); $R_t$=4.05 min.

Example (III-2)

Preparation of 4-(N'-ethyl-N'-methylsulphonylamino-phenethoxy)-amine a) N-[4-(N'-ethyl-N'-methylsulphonylamino-phenethoxy)]-phthalimide:

5.0 g (13.8 mmol) 4-(N'-methylsulphonylamino-phenethoxy)-phthalimide is prepared in 100 ml N,N-dimethylformamide and mixed with 0.52 g (20.8 mmol) sodium hydride. After stirring for approximately 15 minutes at room temperature, 3.2 g (20.8 mmol) ethyl iodide is added, and the mixture is stirred for another 18 hours at room temperature. Afterward, the reaction solution is carefully mixed with 1 ml water and stirred for 30 minutes at room temperature. Subsequently, the entire reaction preparation is concentrated in vacuum, and the remaining residue is chromatographed over a silica gel column (silica gel 60-Merck, grain size: 0.04 to 0.063 mm) using cyclohexane/acetone (3:1) as mobile phases. The reaction yields 4.25 g (78.8% of the theoretical yield) N-[4-(N'-allyl-N'-methylsulphonylamino-phenethoxy)]-phthalimide.

$C_{19}H_{20}N_2O_5S$ (388.4); LC-MS m/z (%)=389 ($MH^+$, 100); $R_t$=5.54 min.

b) 4-(N'-ethyl-N'-methylsulphonylamino-phenethoxy)-amine:

4.0 g (10.3 mmol) N-[4-(N'-ethyl-N'-methylsulphonylamino-phenethoxy)]-phthalimide is stirred in 40 ml dichloromethane and mixed with 2.0 ml methanol and 1.0 g (20.6 mmol) hydrazine hydrate at room temperature. The reaction mixture is stirred for 18 hours at room temperature. The reaction preparation is subsequently filtered, and the filtrate is shaken once with 5N ammonia solution. The organic phase is separated, dried and concentrated in vacuum. The reaction yields 2.4 g (92.4% of the theoretical yield) 4-(N'-ethyl-N'-methylsulphonylamino-phenethoxy)-amine.

$C_{11}H_{18}N_2O_3S$ (258.3); LC-MS m/z (%)=259 ($MH^+$, 25); $R_t$=2.25 min.

The aminoxy compounds according to the general formula (III) listed below in Table 4 can be produced in a similar manner to the previous examples III-1 and III-2.

TABLE 4

$$R^2—X—NH_2 \quad (III)$$

| Example No. | X | $R^2$ | Physical Data |
|---|---|---|---|
| III-3 | O | 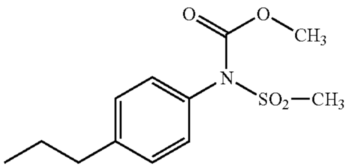 | 289 ($MH^+$, 100); 2.55 min $C_{11}H_{16}N_2O_5S$ (288.3) |
| III-4 | O | 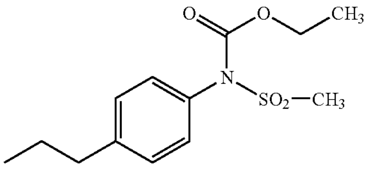 | 303 ($MH^+$, 100); 3.42 min $C_{12}H_{18}N_2O_5S$ (302.3) |
| III-5 | O | 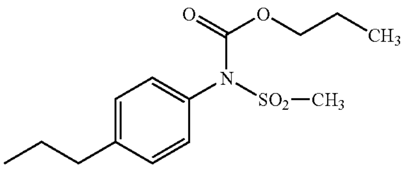 | 317 ($MH^+$, 100); 4.16 min $C_{13}H_{20}N_2O_5S$ (316.3) |
| III-6 | O | 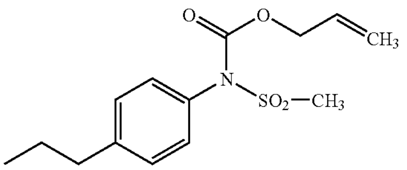 | 315 ($MH^+$, 100); 3.87 min $C_{13}H_{18}N_2O_5S$ (314.3) |

TABLE 4-continued
$$R^2—X—NH_2 \quad (III)$$
| Example No. | X | $R^2$ | Physical Data |
|---|---|---|---|
| III-7 | O | 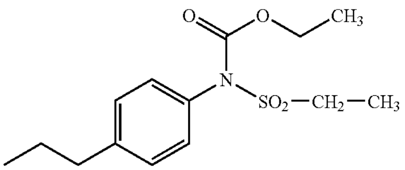 | 317 ($MH^+$, 100); 3.83 min $C_{13}H_{20}N_2O_5S$ (316.4) |
| III-8 | O | 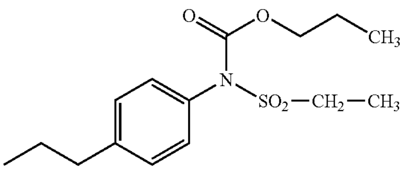 | 331 ($MH^+$, 100); 4.54 min $C_{14}H_{22}N_2O_5S$ (330.4) |
| III-9 | O | 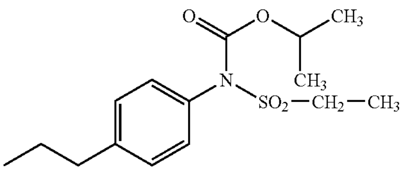 | 331 ($MH^+$, 100); 4.43 min $C_{14}H_{22}N_2O_5S$ (330.4) |
| III-10 | O | 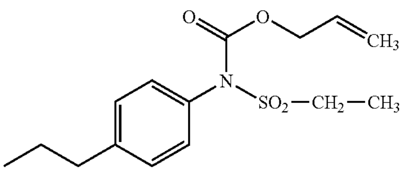 | 329 ($MH^+$, 100); 4.26 min $C_{14}H_{20}N_2O_5S$ (328.4) |
| III-11 | O | 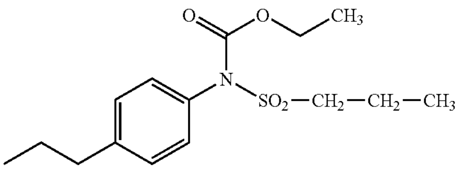 | 331 ($MH^+$, 100); 4.53 min $C_{14}H_{22}N_2O_5S$ (330.4) |
| III-12 | O | 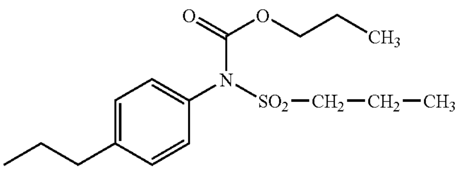 | 345 ($MH^+$, 100); 5.20 min $C_{15}H_{24}N_2O_5S$ (344.4) |
| III-13 | O | 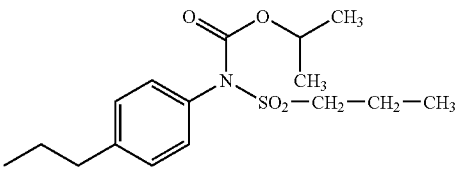 | 345 ($MH^+$, 100); 5.13 min $C_{15}H_{24}N_2O_5S$ (344.4) |
| III-14 | O | 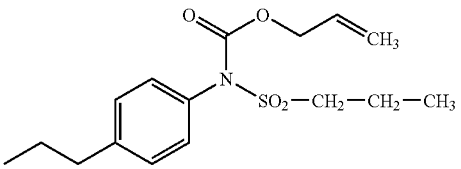 | 343 ($MH^+$, 100); 4.93 min $C_{15}H_{22}N_2O_5S$ (342.4) |

TABLE 4-continued
$$R^2—X—NH_2 \quad (III)$$
| Example No. | X | $R^2$ | Physical Data |
|---|---|---|---|
| III-15 | O | 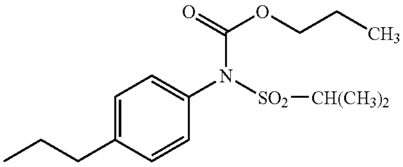 | 345 ($MH^+$, 100); 4.97 min $C_{15}H_{24}N_2O_5S$ (344.4) |
| III-16 | O | 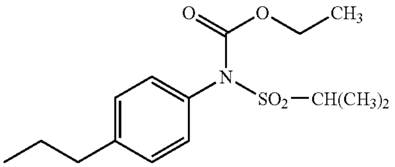 | 331 ($MH^+$, 100); 4.31 min $C_{14}H_{22}N_2O_5S$ (330.4) |
| III-17 | O | 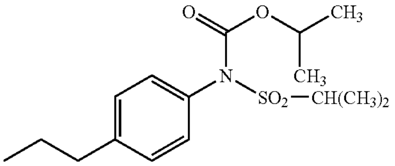 | 345 ($MH^+$, 100); 4.86 min $C_{15}H_{24}N_2O_5S$ (344.4) |
| III-18 | O | 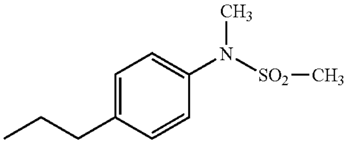 | 245 ($MH^+$, 100); 1.69 min $C_{10}H_{16}N_2O_3S$ (244.3) |
| III-19 | O | 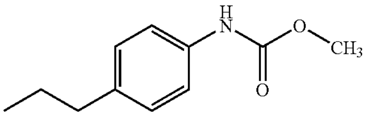 | 1.51 ($MH^+$, 100)/211 min $C_{10}H_{14}N_2O_3$ (210.2) |
| III-20 | O | 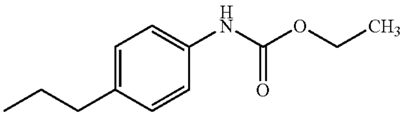 | 225 ($MH^+$, 100)/2.19 min $C_{11}H_{16}N_2O_3$ (224.3) |
| III-21 | O | 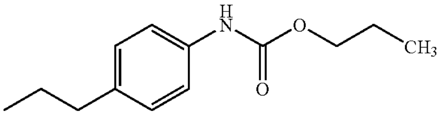 | 239 ($MH^+$, 100)/ 2.84 min $C_{12}H_{18}N_2O_3$ (238.3) |
| III-22 | O | 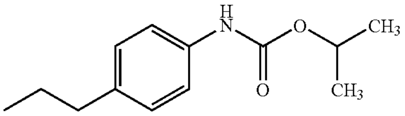 | 239 ($MH^+$, 75)/2.74 min $C_{12}H_{18}N_2O_3$ (238.3) |
| III-23 | O | 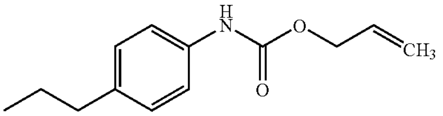 | 237 ($MH^+$, 100)/2.55 min $C_{12}H_{16}N_2O_3$ (236.3) |

TABLE 4-continued
(III)
$R^2$—X—$NH_2$
| Example No. | X | $R^2$ | Physical Data |
|---|---|---|---|
| III-24 | O | 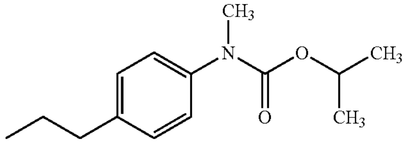 | 253 ($MH^+$, 85)/3.10 min $C_{13}H_{20}N_2O_3$ (252.3) |
| III-25 | O | 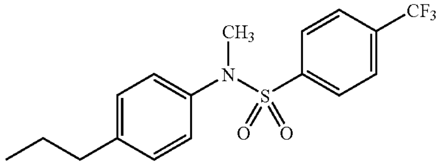 | 375 ($MH^+$, 100)/4.46 min $C_{16}H_{17}F_3N_2O_3S$ (374.4) |
| III-26 | O | 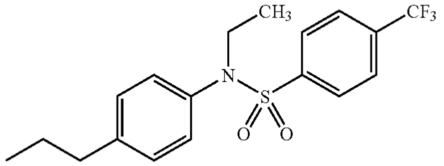 | 389 ($MH^+$, 100)/4.77 min $C_{17}H_{19}F_3N_2O_3S$ (388.4) |
| III-27 | O | 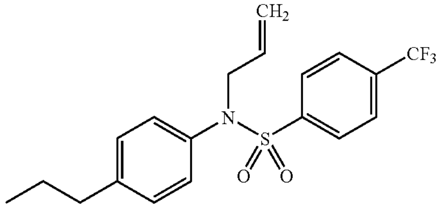 | 401 ($MH^+$, 100)/4.95 min $C_{18}H_{19}F_3N_2O_3S$ (400.4) |
| III-28 | O | 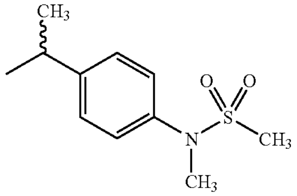 | 245 ($MH^+$, 100)/1.93 min $C_{10}H_{16}N_2O_3S$ (244.3) |
| III-29 | O | 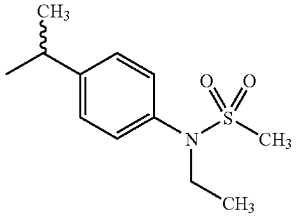 | 259 ($MH^+$, 100)/2.42 min $C_{11}H_{18}N_2O_3S$ (258.3) |

TABLE 4-continued $$R^2—X—NH_2 \quad (III)$$

| Example No. | X | $R^2$ | Physical Data |
|---|---|---|---|
| III-30 | O | 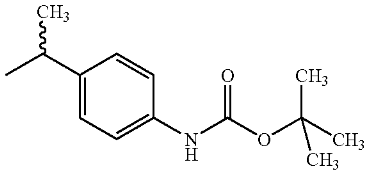 | 253 ($MH^+$, 8)/3.48 min $C_{13}H_{20}N_2O_3$ (252.3) |
| III-31 | N—Z | 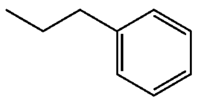 | 271 ($MH^+$, 8)/7.22 min $C_{16}H_{18}N_2O_2$ (270.3) |

Z = —CO—O—$CH_2$-phenyl
LC-MS (acidic) m/z (%)/$R_t$ (min)

The invention claimed is:

1. A compound according to formula (I)

(I)

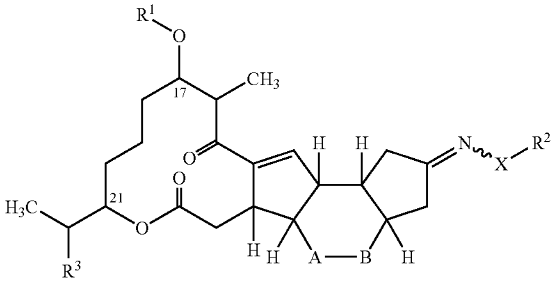

and salts thereof, in which

X represents O, NH, or NMe, $R^1$ represents hydrogen or an amino sugar according to one of the formulas 1a to 1g 1a

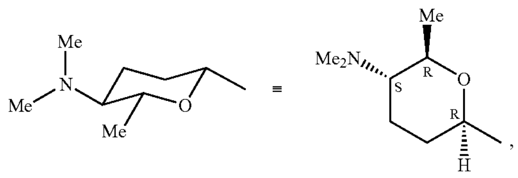

1b

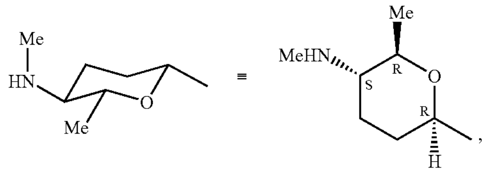

-continued

1c

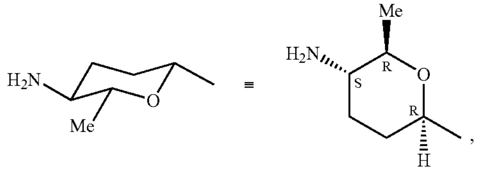

1d

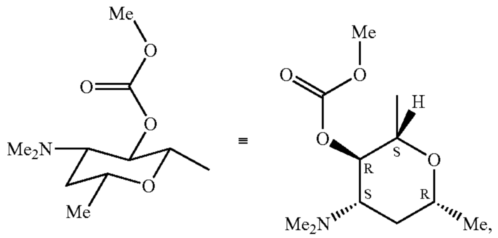

1e

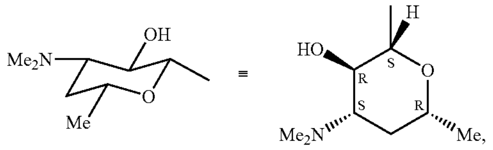

1f

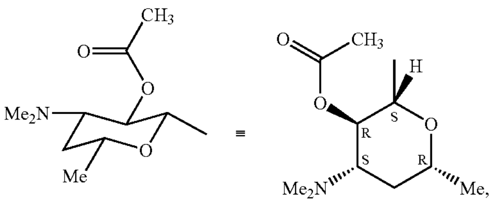

or

-continued

1g

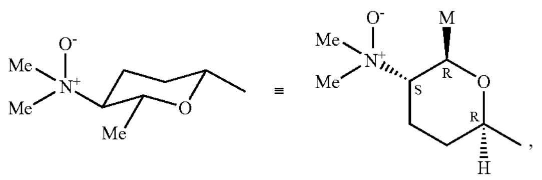

$R^2$ represents optionally substituted aryl-$C_1$-$C_3$-alkyl or hetaryl-$C_1$-$C_3$-alkyl, wherein the substituents are selected from the group consisting of hydrogen, straight-chained or branched alkyl with up to 4 carbon atoms, halogenalkyl with up to 2 carbon atoms, alkenyl with up to 3 carbon atoms, cyclic alkyl with up to 6 carbon atoms, hydroxy, halogen, alkoxy, cycloalkoxy, alkenyloxy, dioxoalkylene, halogenalkoxy, alkylthio, halogenalkylthio, alkylsulphonyl, halogenalkylsulphonyl, hetarylsulphonyl, nitro, amino, a cyclic amino group, alkylamino, alkyleneamino, dialkylamino, carboxyl, carbamoyl, cyano, alkoxycarbonyl, alkyleneoxycarbonyl, N-alkoxycarbonyl-amino, cyanoalkylenecarbonylamino, N-alkyleneoxycarbonylamino, N-alkylsulphonylamino, N-alkylenesulphonylamino, optionally substituted arylsulphonylamino, N-alkoxycarbonyl-N-alkyl-amino, N-alkyleneoxycarbonyl-N-alkylamino, N-alkylcarbonyl-N-alkylamino, N-cycloalkylcarbonylamino, N-cyclobutylamino, N-alkoxycarbonyl-N-alkylsulphonylamino, N-alkyleneoxycarbonyl-N-alkylsulphonylamino, N-alkylcarbonyl-N-alkylsulphonylamino, N-cycloalkylcarbonyl-N-alkylsulphonylamino, alkylamino-carbonylamino, N,N-dialkylaminocarbonylamino, N-alkylaminosulphonylamino, and N,N-dialkylaminosulphonylamino, or if X represents NH or NMe, represents CO—R' or CS—R', where R' represents amino or optionally substituted $C_1$-$C_4$-alkyl, $C_1$-$C_4$-alkylamino, di-$C_1$-$C_4$-alkylamino, aryl, arylamino, hetarylamino, aryl-$C_1$-$C_3$-alkyl, hetaryl, or hetaryl-$C_1$-$C_3$-alkyl, $R^3$ represents hydrogen or hydroxy, and A-B represents —HC═CH—, —HC═C($CH_3$)—, —$H_2C$—$CH_2$—, or —$H_2C$—CH($CH_3$)—.

2. A compound according to claim 1 wherein $R^2$ represents benzyl, 1-phenyl-ethyl, 2-phenyl-ethyl, 3-phenyl-propyl, 2-phenyl-propyl, 2-phenyl-isopropyl, 1-methyl-2-phenyl-ethyl, hetarylmethyl, 1-hetaryl-ethyl, 2-hetaryl-ethyl, 3-hetaryl-propyl, 2-hetaryl-propyl, 2-hetaryl-isopropyl, or 1-methyl-2-hetaryl-ethyl, wherein the substituents are selected from the group consisting of hydrogen, methyl, ethyl, propyl, isopropyl, butyl, isobutyl, sec-butyl, tert-butyl, trifluoromethyl, difluorochloromethyl, pentafluoroethyl, cyclopropyl, cyclobutyl, cyclopentyl, cyclohexyl, hydroxy, bromine, chlorine, fluorine, iodine, methoxy, ethoxy, propoxy, isopropoxy, butoxy, isobutoxy, sec-butoxy, tert-butoxy, cyclopropyloxy, allyloxy, dioxomethylene, trifluoromethoxy, methylthio, trifluoromethylthio, methylsulphonyl, trifluoromethylsulphonyl, N-morpholinosulphonyl, N-pyrazolylsulphonyl, nitro, amino, N-pyrrolidino, N-piperidino, N-morpholino, N-(2,6-dimethyl-morpholino), N-methyl-piperazino, N-thiomorpholino, N-dioxothiomorpholino, methylamino, ethylamino, propylamino, isopropylamino, butylamino, sec-butylamino, isobutylamino, tert-butylamino, propyleneamino, dimethylamino, diethylamino, carboxyl, carbamoyl, cyano, methoxycarbonyl, ethoxycarbonyl, propyloxy-carbonyl, isopropyloxycarbonyl, butyloxycarbonyl, sec-butyloxycarbonyl, isobutyloxycarbonyl, tert-butyloxycarbonyl, propyleneoxycarbonyl, N-methoxycarbonylamino, N-ethoxycarbonylamino, N-propyloxycarbonylamino, N-isopropyloxycarbonylamino, N-butyloxycarbonylamino, N-sec-butyloxycarbonylamino, N-isobutyloxycarbonylamino, N-tert-butyloxycarbonylamino, cyanomethylenecarbonylamino, cyanoethylenecarbonylamino, N-propyleneoxycarbonylamino, N-methylsulphonylamino, N-ethylsulphonylamino, N-propylsulphonylamino, N-isopropylsulphonyl-amino, N-butylsulphonylamino, N-sec-butylsulphonylamino, N-isobutylsulphonylamino, N-tert-butylsulphonylamino, N-propylenesulphonylamino, 4-trifluoromethyl-phenylsulphonylamino, N-methoxycarbonyl-N-methylamino, N-methoxy-carbonyl-N-ethylamino, N-ethoxycarbonyl-N-methylamino, N-ethoxycarbonyl-N-ethylamino, N-propyloxycarbonyl-N-methylamino, N-propyloxycarbonyl-N-ethylamino, N-isopropyloxycarbonyl-N-methylamino, N-isopropyloxycarbonyl-N-ethylamino, N-butyloxycarbonyl-N-methylamino, N-butyloxycarbonyl-N-ethyl-amino, N-sec-butyloxycarbonyl-N-methylamino, N-sec-butyloxycarbonyl-N-ethylamino, N-isobutyloxycarbonyl-N-methyl-amino, N-isobutyloxycarbonyl-N-ethylamino, N-tert-butyloxycarbonyl-N-methylamino, N-tert-butyloxycarbonyl-N-methylamino, N-propyleneoxycarbonyl-N-methylamino, N-propyleneoxycarbonyl-N-methylamino, N-methylcarbonyl-N-methylamino, N-methyl-carbonyl-N-ethylamino, N-ethyl-carbonyl-N-methylamino, N-ethylcarbonyl-N-ethylamino, N-cyclopropylcarbonylamino, N-1-methylcycloprop-1-yl-carbonyl-N-amino, N-cyclobutylamino, N-methoxy-carbonyl-N-methylsulphonylamino, N-methoxycarbonyl-N-ethylsulphonylamino, N-ethoxycarbonyl-N-methylsulphonylamino, N-ethoxycarbonyl-N-ethylsulphonylamino, N-propyloxycarbonyl-N-methylsulphonylamino, N-propyloxycarbonyl-N-ethylsulphonylamino, N-isopropyloxycarbonyl-N-methylsulphonylamino, N-isopropyloxycarbonyl-N-ethylsulphonylamino, N-butyloxycarbonyl-N-methylsulphonylamino, N-butyloxycarbonyl-N-ethylsulphonylamino, N-sec-butyloxycarbonyl-N-methylsulphonylamino, N-sec-butyloxycarbonyl-N-ethylsulphonylamino, N-isobutyloxycarbonyl-N-methylsulphonylamino, N-isobutyloxycarbonyl-N-ethylsulphonylamino, N-tert-butyloxycarbonyl-N-methylsulphonylamino, N-tert-butyloxycarbonyl-N-methylsulphonylamino, N-propyleneoxycarbonyl-N-methylsulphonylamino, N-propyleneoxycarbonyl-N-methylsulphonyl-amino, N-methylcarbonyl-N-methylsulphonylamino, N-methylcarbonyl-N-ethylsulphonylamino, N-ethylcarbonyl-N-methylsulphonylamino, N-ethylcarbonyl-N-ethylsulphonylamino, N-cyclopropylcarbonyl-N-methylsulphonylamino, N-1-methylcycloprop-1-yl-carbonyl-N-methylsulphonylamino, N-cyclobutyl-N-methylsulphonylamino, N-methylaminocarbonylamino, N-ethylaminocarbonylamino, N,N-dimethylaminocarbonylamino, N-methylaminosulphonylamino, and N,N-dimethylaminosulphonylamino, or if X represents NH or NMe, represents CO—R' or CS—R', where R' represents amino or optionally substituted $C_1$-$C_4$-alkyl, $C_1$-$C_4$-alkylamino, di-$C_1$-$C_4$-alkylamino, aryl, arylamino, hetarylamino, aryl-$C_1$-$C_3$-alkyl, hetaryl, or hetaryl-$C_1$-$C_3$-alkyl.

3. A compound according to claim 1 wherein

X represents O or NH, $R^1$ represents hydrogen or an amino sugar according to formulas 1a, 1d, or 1e 1a

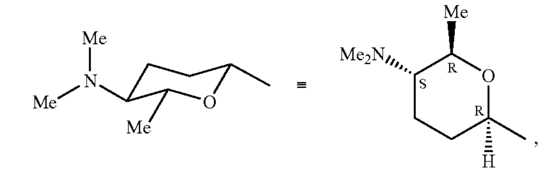

,

1d

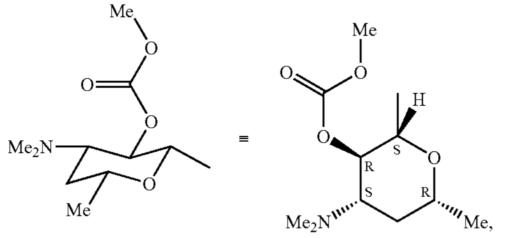

or

1e

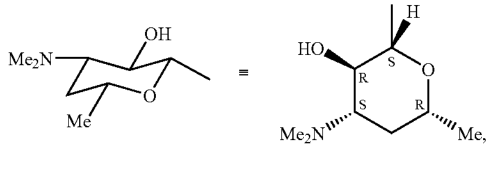

, $R^2$ represents aryl-$C_1$-$C_3$-alkyl or hetaryl-$C_1$-$C_3$-alkyl that are optionally substituted by moieties selected from the group consisting of hydrogen, straight-chained or branched alkyl with up to 4 carbon atoms, halogenalkyl, hydroxy, halogen, alkoxy, halogenalkoxy, alkylthio, halogenalkylthio, alkylsulphonyl, halogenalkylsulphonyl, nitro, amino, alkylamino, N-alkoxycarbonylamino, N-alkyleneoxycarbonylamino, N-alkylsulphonylamino, N,N-alkoxycarbonyl-N-alkylamino, N-alkyleneoxycarbonyl-N-alkylamino, N-alkylcarbonyl-N-alkylamino, N-cycloalkylcarbonylamino, N-alkoxycarbonyl-N-alkylsulphonylamino, N-alkyleneoxycarbonyl-N-alkylsulphonyl-amino, N-alkylcarbonyl-N-alkylsulphonylamino, N-cycloalkylcarbonyl-N-alkylsulphonylamino, alkylaminocarbonylamino, N,N-dialkylaminocarbonylamino, N-alkylaminosulphonylamino, and N,N-dialkylaminosulphonylamino, or if X represents NH or NMe, represents CO—R' or CS—R', where R' represents amino, arylamino, or hetarylamino.

4. A compound according to claim 1 wherein

X represents O or NH, $R^1$ represents hydrogen or an amino sugar according to formulas 1a, 1d, or 1e 1a

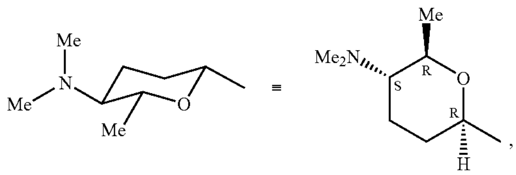

,

1d

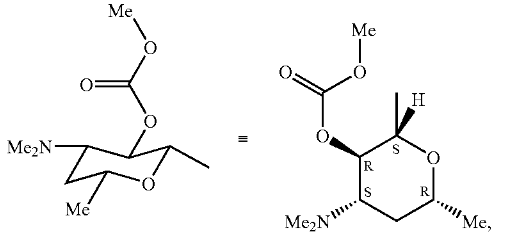

or

1e

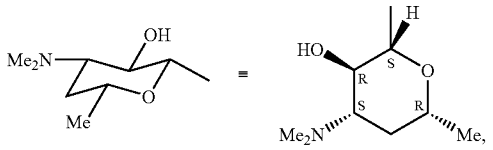

, $R^2$ represents benzyl, 1-phenylethyl, pyridylmethyl, pyrimidylmethyl, pyridazinylmethyl, pyrazylmethyl, furylmethyl, thiazolylmethyl, pyrazolylmethyl, oxazolylmethyl, isoxazolylmethyl, thiazolylmethyl, imidazolylmethyl, triazolylmethyl, tetrazolylmethyl, dihydrodioxazinylmethyl, 1-pyridylethyl, 1-pyrimidylethyl, 1-pyridazinylethyl, 1-pyrazylethyl, 1-furylethyl, 1-thiazolylethyl, 1-pyrazolylethyl, 1-oxazolylethyl, 1-isoxazolylethyl, 1-thiazolylethyl, 1-imidazolylethyl, 1-triazolylethyl, 1-tetrazolylethyl, or 1-dihydrodioxazinylethyl, each of which is optionally substituted by moieties selected from the group consisting of hydrogen, methyl, ethyl, propyl, tert-butyl, trifluoromethyl, hydroxy, bromine, chlorine, fluorine, iodine, methoxy, ethoxy, tert-butoxy, trifluoromethoxy, methylthio, trifluoromethylthio, methylsulphonyl, trifluoromethylsulphonyl, nitro, amino, methylamino, ethylamino, N-methoxycarbonylamino, N-ethoxycarbonylamino, N-propyloxycarbonylamino, N-isopropyloxycarbonylamino, N-butyloxycarbonylamino, N-sec-butyloxycarbonylamino, N-isobutyloxycarbonylamino, N-tert-butyloxycarbonylamino, N-propyleneoxycarbonylamino, N-methylsulphonylamino, N-ethylsulphonylamino, N-propylsulphonylamino, N-isopropylsulphonylamino, N-butylsulphonylamino, N-sec-butylsulphonylamino, N-isobutylsulphonylamino, N-tert-butylsulphonylamino, N-methoxycarbonyl-N-methylamino, N-methoxy-carbonyl-N-ethylamino, N-ethoxycarbonyl-N-methylamino, N-ethoxycarbonyl-N-ethylamino, N-propyloxycarbonyl-N-methylamino, N-propyloxycarbonyl-N-ethylamino, N-isopropyloxycarbonyl-N-methylamino, N-isopropyloxycarbonyl-N-ethylamino, N-butyloxycarbonyl-N-methylamino, N-butyloxycarbonyl-N-ethylamino, N-sec-butyloxycarbonyl-N-methylamino, N-sec-butyloxycarbonyl-N-ethyl-amino, N-isobutyloxycarbonyl-N-methylamino, N-isobutyloxycarbonyl-N-ethylamino, N-tert-butyloxycarbonyl-N-methylamino, N-tert-butyloxycarbonyl-N-methylamino, N-propyleneoxycarbonyl-N-methylamino, N-propyleneoxycarbonyl-N-methylamino, N-methylcarbonyl-N-methyl-amino, N-methylcarbonyl-N-ethylamino, N-ethylcarbonyl-N-methyl-amino, N-ethylcarbonyl-N-ethylamino, N-cyclopropylcarbonylamino, N-1-methylcycloprop-1-yl-carbonyl-N-amino, N-cyclobutylamino, N-methoxycarbonyl-N-methylsulphonylamino, N-methoxycarbonyl-N-ethylsulphonylamino, N-ethoxycarbonyl-N-methylsulphonylamino, N-ethoxycarbonyl-N-ethylsulphonylamino, N-propyloxycarbonyl-N-methylsulphonyl-amino, N-propyloxycarbonyl-N-ethylsulphonylamino, N-isopropyloxycarbonyl-N-methylsulphonylamino, N-isopropyloxycarbonyl-N-ethylsulphonylamino, N-butyloxycarbonyl-N-methyl-sulphonylamino, N-butyloxycarbonyl-N-ethylsulphonylamino, N-sec-butyloxycarbonyl-N-methylsulphonylamino, N-sec-butyloxycarbonyl-N-ethylsulphonylamino, N-isobutyloxycarbonyl-N-methylsulphonyl-amino, N-isobutyloxy-carbonyl-N-ethylsulphonylamino, N-tert-butyloxycarbonyl-N-methylsulphonylamino, N-tert-butyloxycarbonyl-N-methylsulphonylamino, N-propyleneoxycarbonyl-N-methylsulphonylamino, N-propyleneoxycarbonyl-N-methylsulphonylamino, N-methylcarbonyl-N-methylsulphonyl-amino, N-methylcarbonyl-N-ethylsulphonyl-amino, N-ethylcarbonyl-N-methylsulphonylamino, N-ethylcarbonyl-N-ethylsulphonylamino, N-cyclopropylcarbonyl-N-methylsulphonylamino, N-1-methylcycloprop-1-yl-carbonyl-N-methylsulphonylamino, N-cyclobutyl-N-methylsulphonylamino, N-methylaminocarbonylamino, N-ethyl-aminocarbonylamino, N,N-dimethylaminocarbonylamino, N-methylaminosulphonylamino, and N,N-dimethylamino-sulphonylamino, or if X represents NH or NMe, represents CO—R' or CS—R', where R' represents amino, trifluoromethoxyphenylamino, trifluoromethylphenylamino, chlorophenylamino, bromopyridylamino, or trifluoromethylpyridylamino.

5. A compound according to claim 1 wherein

X represents O, $R^1$ represents hydrogen or an amino sugar according to formulas 1a or 1e 1a

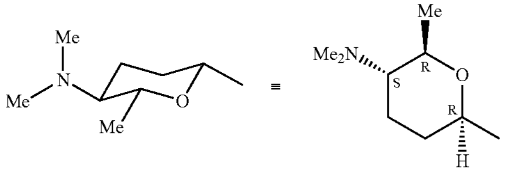

or

1e

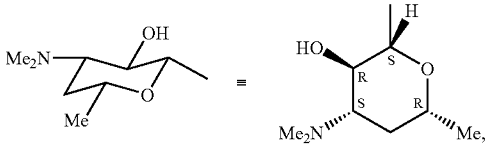

$R^2$ represents benzyl, 1-phenylethyl, or hetarylmethyl, each of which is optionally substituted by moieties selected from the group consisting of hydrogen, methyl, tert-butyl, trifluoromethyl, bromine, chlorine, fluorine, methoxy, trifluoromethoxy, nitro, amino, methylamino, ethylamino, N-methoxycarbonylamino, N-ethoxycarbonylamino, N-propyloxycarbonylamino, N-isopropyloxycarbonylamino, N-tert-butyloxycarbonylamino, N-propyleneoxycarbonylamino, N-methylsulphonylamino, N-ethylsulphonylamino, N-methoxycarbonyl-N-methylamino, N-ethoxycarbonyl-N-methylamino, N-isopropyloxycarbonyl-N-methyl-amino, N-tert-butyloxycarbonyl-N-methylamino, N-propyleneoxycarbonyl-N-methylamino, N-cyclopropylcarbonylamino, N-1-methylcycloprop-1-yl-carbonyl-N-amino, N-methoxycarbonyl-N-methylsulphonylamino, N-methoxycarbonyl-N-ethylsulphonylamino, N-isobutyloxycarbonyl-N-methylsulphonylamino, N-tert-butyloxycarbonyl-N-methylsulphonylamino, N-tert-butyloxycarbonyl-N-methylsulphonylamino, N-propyleneoxycarbonyl-N-methylsulphonylamino, N-cyclopropylcarbonyl-N-methylsulphonyl-amino, N-1-methylcycloprop-1-yl-carbonyl-N-methylsulphonyl-amino, N,N-dialkylaminocarbonylamino, N-methylaminosulphonylamino, and N,N-dialkylaminosulphonylamino.

6. A compound according to claim 1 wherein

X represents O, $R^1$ represents hydrogen or an amino sugar according to formulas 1a or 1e 1a

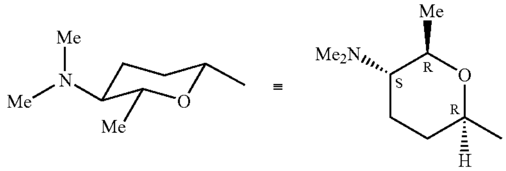

or

1e

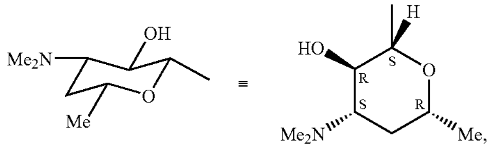

$R^2$ represents benzyl, 1-phenylethyl, pyridylmethyl, pyridazinylmethyl, thiazolylmethyl, pyrazolylmethyl, isoxazolylmethyl, imidazolylmethyl, dihydrodioxazinylmethyl, 1-pyridylethyl, 1-thiazolylethyl, or 1-dihydrodioxazinylethyl, each of which is optionally substituted by moieties selected from the group consisting of hydrogen, methyl, tert-butyl, trifluoromethyl, bromine, chlorine, fluorine, methoxy, trifluoromethoxy, nitro, amino, methylamino, ethylamino, N-methoxycarbonylamino, N-ethoxycarbonylamino, N-propyloxycarbonylamino, N-isopropyloxycarbonylamino, N-tert-butyloxycarbonylamino, N-propyleneoxycarbonylamino, N-methylsulphonylamino, N-ethylsulphonylamino, N-methoxycarbonyl-N-methylamino, N-ethoxycarbonyl-N-methylamino, N-isopropyloxycarbonyl-N-methyl-amino, N-tert-butyloxycarbonyl-N-methylamino, N-propyleneoxy-carbonyl-N-methylamino, N-cyclopropylcarbonylamino, N-1-methylcycloprop-1-yl-carbonyl-N-amino, N-methoxycarbonyl-N-methylsulphonylamino, N-methoxycarbonyl-N-ethylsulphonylamino, N-isobutyloxycarbonyl-N-methylsulphonylamino, N-tert-butyloxycarbonyl-N-methylsulphonylamino, N-tert-butyloxycarbonyl-N- methylsulphonylamino, N-propyleneoxycarbonyl-N-methylsulphonylamino, N-cyclopropylcarbonyl-N-methylsulphonyl-amino, N-1-methylcycloprop-1-yl-carbonyl-N-methylsulphonyl-amino, N,N-dialkylaminocarbonylamino, N-methylaminosulphonylamino, and N,N-dialkylaminosulphonylamino.

7. A compound according to claim 1 wherein A-B represents —HC═CH— or —$H_2C$—$CH_2$—.

8. A process for the manufacture of a compound of formula (I) according to claim 1

(I)

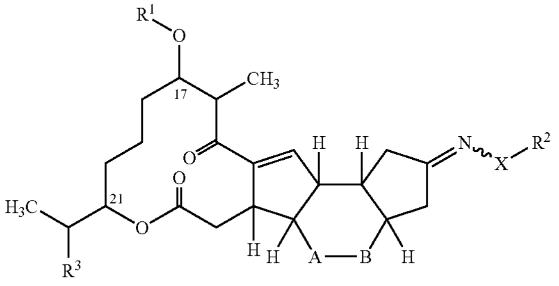

and derived salts thereof, in which $R^1$, $R^2$, $R^3$, X, and A-B have the meanings specified in claim 1, comprising reacting a compound of formula (II)

(II)

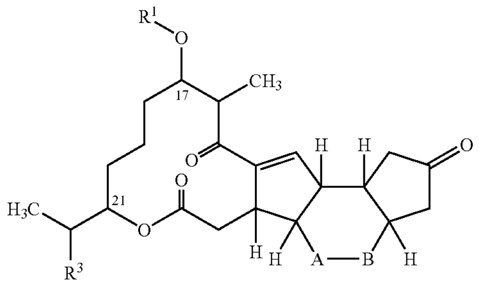

in which $R^1$, $R^3$, and A-B have the meanings specified for formula (I), with an amino compound of formula (III)

$$H_2N—X—R^2 \quad \text{(III)}$$

in which $R^2$ and X have the meanings specified for formula (I), in the presence of a basic catalyst and, if applicable, in the presence of a diluent.

9. An agent for controlling animal pests comprising one or more compounds according to formula (I) of claim 1 and one or more extenders and/or surfactants.

10. A method for controlling animal pests comprising applying an effective amount of one or more compounds according to formula (I) of claim 1 to the animal pests and/or their habitat.

11. A process for the manufacture of agents for controlling pests comprising mixing one or more compounds according to claim 1 with one or more extenders and/or surfactants.

* * * * *